US010738333B2

(12) United States Patent
Elmore et al.

(10) Patent No.: US 10,738,333 B2
(45) Date of Patent: Aug. 11, 2020

(54) PRODUCTION OF ITACONIC ACID AND RELATED MOLECULES FROM AROMATIC COMPOUNDS

(71) Applicants: UT-Battelle, LLC, Oak Ridge, TN (US); Alliance for Sustainable Energy, LLC, Golden, CO (US)

(72) Inventors: Joshua R. Elmore, Richland, WA (US); Jay Huenemann, Knoxville, TN (US); Davinia Salvachua, Golden, CO (US); Gregg T. Beckham, Golden, CO (US); Adam M. Guss, Knoxville, TN (US)

(73) Assignees: UT-BATTELLE, LLC, Oak Ridge, TN (US); ALLIANCE FOR SUSTAINABLE ENERGY, LLC, Golden, CO (US)

( * ) Notice: Subject to any disclaimer, the term of this patent is extended or adjusted under 35 U.S.C. 154(b) by 0 days.

(21) Appl. No.: 16/397,256

(22) Filed: Apr. 29, 2019

(65) Prior Publication Data

US 2019/0330665 A1 Oct. 31, 2019

Related U.S. Application Data

(60) Provisional application No. 62/664,570, filed on Apr. 30, 2018.

(51) Int. Cl.

| | |
|---|---|
| ***C12P 7/44*** | (2006.01) |
| ***C12N 1/20*** | (2006.01) |
| ***C12R 1/38*** | (2006.01) |
| ***C12N 15/74*** | (2006.01) |
| ***C12N 9/90*** | (2006.01) |
| ***C12N 9/10*** | (2006.01) |
| ***C12N 9/88*** | (2006.01) |

(52) U.S. Cl.

CPC .................. *C12P 7/44* (2013.01); *C12N 1/20* (2013.01); *C12N 9/1025* (2013.01); *C12N 9/88* (2013.01); *C12N 9/90* (2013.01); *C12N 15/74* (2013.01); *C12R 1/38* (2013.01); *C12Y 203/03001* (2013.01); *C12Y 401/01006* (2013.01); *C12Y 503/03007* (2013.01)

(58) Field of Classification Search

CPC ........... C12P 7/44; C12N 9/88; C12N 9/1025; C12N 9/90; C12N 15/74; C12N 1/20; C12R 1/38; C12Y 503/03007; C12Y 401/01006; C12Y 203/03001; C07K 14/32; C07K 14/375

See application file for complete search history.

(56) References Cited

U.S. PATENT DOCUMENTS

| | | | | |
|---|---|---|---|---|
| 8,143,036 | B2 | 3/2012 | Liao et al. | |
| 8,192,965 | B2 | 6/2012 | Wang et al. | |
| 2010/0285546 | A1 * | 11/2010 | Liao | C12N 1/20 435/145 |
| 2010/0311132 | A1 | 12/2010 | Van Der Werf et al. | |
| 2011/0124066 | A1 | 5/2011 | Jore et al. | |
| 2015/0291986 | A1 | 10/2015 | Zhao et al. | |
| 2017/0096690 | A1 | 4/2017 | Boelker et al. | |

FOREIGN PATENT DOCUMENTS

| | | | |
|---|---|---|---|
| WO | 2014/161988 | A1 | 10/2014 |
| WO | WO 2015/140314 | * | 9/2015 |
| WO | 2016/069849 | A1 | 5/2016 |

OTHER PUBLICATIONS

Sousa et al., Microbiology 148(Pt5):1291-1303, 2002.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Rodriguez et al., ACS Sustainable Chemistry and Engineering 5:8171-8180, Aug. 1, 2017.*
Saha, B., J Ind Microbiol Biotechnol 44:303-315, published on-line Dec. 8, 2016.*
Harder et al., Metabolic Engineering 38:29-37, 2016.*
Du et al., Journal of Biological Chemistry 292(8):3517-3530, Feb. 24, 2017.*
Kobayashi et al., ChemistrySelect 1(7): 1467-1471, May 25, 2016.*
Zhou et al., Cell Mol Life Sci 63(19-20):2260-2290, 2006.*
Kozak, M., Gene 234:187-208, 1999.*
Linger, J.G. et al., "Lignin valorization through integrated biological funneling and chemical catalysis", Proc Natl Acad Sci U S A., Aug. 19, 2014; 111(33):12013-8, pp. 1-6.

* cited by examiner

*Primary Examiner* — Delia M Ramirez
(74) *Attorney, Agent, or Firm* — Scully Scott Murphy & Presser

(57) ABSTRACT

This disclosure provides a genetically-modified bacterium from the genus *Pseudomonas* that produces itaconate or trans-aconitate. The disclosure further provides methods for producing itaconate or trans-aconitate using a genetically-modified bacterium from the genus *Pseudomonas*.

52 Claims, 11 Drawing Sheets
(11 of 11 Drawing Sheet(s) Filed in Color)
Specification includes a Sequence Listing.

PRODUCTION OF ITACONIC ACID AND RELATED MOLECULES FROM AROMATIC COMPOUNDS

CROSS REFERENCE TO RELATED APPLICATION

This application claims the benefit of priority from U.S. Provisional Application No. 62/664,570, filed Apr. 30, 2018, the contents of which are incorporated herein by reference.

STATEMENT REGARDING FEDERALLY SPONSORED RESEARCH OR DEVELOPMENT

This disclosure was made with government support under a research project supported by Prime Contract Nos. DE-AC05-00OR22725 and DE-AC36-08GO28308 awarded by the U.S. Department of Energy. The government has certain rights in this invention.

INCORPORATION BY REFERENCE OF SEQUENCE LISTING

The Sequence Listing in the ASCII text file, named as 37129_SEQLISTING_ST25.txt of 187 KB, created on Apr. 23, 2019, and submitted to the United States Patent and Trademark Office via EFS-Web, is incorporated herein by reference.

BACKGROUND

Lignin is one of the most abundant polymers on earth, second only to cellulose. Its complex structure makes it highly resistant to microbial degradation. Consequently, lignin is the primary cause of recalcitrance of lignocellulosic feedstock, and the primary constituent of waste effluent from second-generation biofuel fermentation. The United States can generate 1.3 billion dry tons of lignocellulosic biomass annually without competing with food crops for land use, and hence potentially deliver an equivalent supply of 3.8 billion barrels of oils that can replace more than 50% of liquid transportation derived from fossil fuels. However, one major limitation is that lignocellulosic residuals (i.e., lignins) constituting about 30% of the total biomass content cannot be currently used for fermentation and are underused as a low-value heating source by biorefinery processes. Therefore, it is significant to develop enabling technologies for transformation of this underused biomass source into high-value chemicals, biofuels, and biomaterials.

Utilization of the effluent lignocellulose waste stream would improve the overall process efficiency of second-generation biofuel production because the additional product would offset operating costs. This would effectively decrease the cost of the ethanol or butanol products, making them more competitive with traditional fossil fuels. Valorization of this waste stream will decrease the cost of treatment for any producing industries. So research paradigms or commercial ventures need not retool their foundational goals or core business models to incorporate this process.

Second-generation biofuels are a renewable energy source produced from lignocellulosic biomass, and they are fully compatible with existing infrastructure. Biofuels are produced in large bioreactors using single-celled microorganisms to convert the biomass into ethanol, butanol, or other hydrocarbons via fermentation processes. These single-celled organisms are incapable of degrading lignin, and consequently, the lignocellulosic biomass is never fully converted into desired products. In addition, the lignin present in the biomass feedstock shields the cellulose and hemicellulose that the microorganisms utilize effectively preventing optimum yields even when lignin degradation is not considered. Thus, up to 30% dry weight of the feedstock remain as lignin-containing residuals and wastes after biofuel production. Beside biofuel productions, other industrial activities that use lignocellulosic feedstock (e.g., production of pulp or paper) produce important amounts of lignocellulosic wastes. The resulting lignin-enriched waste stream is toxic to many microbes and plants, which leads to complications in its disposal since it is considered as hazardous waste. For twenty years, main treatment of lignocellulosic waste consisted of burning such wastes or burying, both of which have huge impacts on the environment. Then interest for valorizing these wastes rapidly expended over the recent years, using them as combustible heating source, for conversion by pyrolysis into char, gas and oil and used in building composite material. However, all these treatments convert only up to 3% of the remaining lignin.

The current slate of demonstrated lignin-derived products is very small and limited to native carbon storage compounds and intermediates of aromatic catabolism. To increase the portfolio of products that can be made from lignin, other parts of metabolism will need to be targeted.

The TCA cycle is a source of many value-added chemicals including succinate and citrate, but it has not yet been harnessed for lignin valorization. Itaconic acid (and its salt, itaconate, which are used interchangeably herein) and trans-aconitic acid (and its salt, trans-aconitate, which are used interchangeably herein) are unsaturated dicarboxylic acids derived from the TCA cycle with industrial uses including as an acrylate alternative and for the production of plastics, latex and other polymers (da Cruz et al., 3 *Biotech* 8.3 (2018): 138). Itaconate has been produced from simple sugars since the 1950s (Kuenz, A. et al., *Applied Microbiology, and Biotech.* 102.9 (2018): 3901-3914), and its potential to functionally replace several petroleum-derived commodity chemicals was highlighted by its selection as one of the top bio-based platform chemicals in several reports, including a 2004 United States Department of Energy report (Werpy, T. et al, No. DOE/GO-102004-1992. National Renewable Energy Lab, Golden, Colo. (US), 2004). However, the high cost of sugars makes itaconate production expensive, limiting it to use as a specialty chemical. Using lignin, a cheap and abundant feedstock, for production would enable much broader industrial use of itaconate.

The saprophytic bacterium *Pseudomonas putida* KT2440 is a microbe of industrial interest due to its robust metabolism (Ebert, Birgitta E., et al., *Appl. Environ. Microbiol.* 77.18 (2011): 6597-6605) and tolerance to xenobiotics (Kieboom, J. et al., *Journal of Biological Chemistry* 273.1 (1998), 85-91; Fernández, M. et al., *Microbial biotechnology* 2.2 (2009): 287-294.; Inoue, A. et al., *Nature* 338.6212 (1989): 264). *P. putida* also has the ability to tolerate and catabolize a wide-range of aromatic compounds (Jiménez, J I. et al., *Environmental microbiology* 4.12 (2002): 824-841) which led to its recent use in upgrading depolymerized lignin into PHAs (Gong, T. et al., *Microbial biotechnology* 9.6 (2016): 792-800; Linger, Jeffrey G., et al., *Metabolic engineering communications* 3 (2016): 24-29) and cis, cis-muconic acid (Kohlstedt, M. et al., *Metabolic engineering* 47 (2018): 279-293; Linger, J G., et al., *PNAS* 111.33 (2014): 12013-12018). In *P. putida*, lignin-derived aromatics are funneled into the β-ketoadipate pathway, producing acetyl-CoA and succinate (FIG. 1A). This direct route to key TCA cycle intermediates suggests that high yields of TCA cycle-derived products such as itaconate should be possible from lignin.

Growth phase production of itaconate may be challenging because itaconate can disrupt bacterial growth via inhibition of enzymes in the glyoxylate shunt and citramalate cycle. An alternate approach is to use a two-stage process to decouple growth of the microbial catalyst from conversion of feedstocks to chemicals, which provides solutions to many problems present in growth-associated processes (e.g. product toxicity, slow catalyst growth) (Burg, Jonathan M., et al., *Curr. Op. in Chem. Eng.,* 14 (2016): 121-136). Such processes often take advantage of the natural responses of microbes to various nutrient limitations (e.g., nitrogen, sulfur, phosphate) and environmental shifts (e.g., $O_2$ limitation, temperature shifts) that prevent microbial growth while maintaining the metabolic reactions of interest and can be coupled with dynamic metabolic control tools to entirely reroute metabolism.

While itaconate is a valuable biologically-derived platform chemical, it inhibits the growth of many bacteria—particularly during growth on C1-C3 compounds—by inhibiting isocitrate lysate (Michelucci, Alessandro, et al., *PNAS,* 110.19 (2013): 7820-7825), which has limited industrial production to a few fungal species with narrow substrate ranges (Kuenz, A. et al., *App. Microbio. & Biotech.,* 102.9 (2018): 3901-3914; da Cruz, Juliana Cunha et al., *Biotech* 8.3 (2018): 138). The use of *Pseudomonas putida* as a platform for itaconate production would broaden the range of industrially-relevant feedstocks that could be upgraded to include lignocellulosic hydrolysates, lignin streams (Rodriguez et al. *Acs Sustain Chem Eng* 5, 8171-8180 (2017); Linger, J G., et al., *PNAS,* 111.33 (2014): 12013-12018), pyrolysis oil (Jayakody, L N., et al., *Energy & Environ. Sci.,* 11.6 (2018): 1625-1638.), and more.

BRIEF SUMMARY OF THE DISCLOSURE

In one aspect, the disclosure provides a genetically-modified bacterium from the genus *Pseudomonas* that utilizes TCA cycle intermediates to produce itaconate and trans-aconitate.

In some embodiments, the genetically-modified bacterium from the genus *Pseudomonas* comprises an exogenous nucleic acid encoding an enzyme that uses cis-aconitate as a substrate.

In some embodiments, the enzyme that uses cis-aconitate as a substrate is a cis-aconitate decarboxylase enzyme. In some embodiments, the cis-aconitate decarboxylase enzyme is encoded by a codon-optimized variant of the cadA gene from *Aspergillus terreus*. In some embodiments, the expression of the cis-aconitate decarboxylase enzyme is dynamically regulated. In a specific embodiment, the dynamic regulation of the cis-aconitate decarboxylase enzyme is achieved by a nitrogen-responsive promoter.

In some embodiments, the enzyme that uses cis-aconitate as a substrate is a cis-aconitate isomerase. In some embodiments, the genetically-engineered bacterium further expresses a trans-aconitate decarboxylase. In some embodiments, the cis-aconitate isomerase is encoded by a codon-optimized variant of the adi1 gene, and the trans-aconitate decarboxylase is encoded by a codon-optimized variant of the tad1 gene.

In some embodiments, the endogenous phaC1 and phaC2 genes, which encode polyhydroxyalkanoates (PHA) synthases, are inactivated in the bacterium to prevent formation of a competing product (PHA).

In some embodiments, the genetically-engineered bacterium further expresses a heterologous citrate synthase enzyme. In a specific embodiment, the citrate synthase enzyme is encoded by a codon-optimized, mutant variant of the *Escherichia coli* gltA gene. Citrate synthase catalyzes the formation of citrate from oxaloacetate and acetyl-CoA (FIG. 1B). Many of these enzymes are allosterically inhibited by intermediates expected to accumulate during production of itaconate, such as citrate. In some embodiments, the mutant variant of gltA is immune to allosteric inhibition.

In some embodiments, the genetically-modified bacterium further expresses an itaconic acid efflux pump. In some embodiments, the itaconic acid efflux pump is encoded by the itp1 gene. In a specific embodiment, the itp1 gene is a codon-optimized variant of the gene.

In some embodiments, the levels of the isocitrate dehydrogenase enzymes in the bacterium is reduced compared to a non-genetically-modified bacterium. Without committing to one particular theory, this reduction in levels of isocitrate dehydrogenases is thought to allow accumulation of the itaconate precursor cis-aconitate. In some embodiments, the genetically-modified bacterium has reduced expression of icd and idh genes, which encode for isocitrate dehydrogenases.

In some embodiments, the genetically-modified bacterium expresses a heterologous cis-aconitate isomerase enzyme but does not express a trans-aconitate decarboxylase enzyme, thereby allowing trans-aconitate to accumulate.

In some embodiments, the genetically-modified bacterium further expresses a trans-aconitate efflux pump. In some embodiments, the aconitate efflux pump is encoded by a codon-optimized variant of the tbrB gene.

In some embodiments, the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. proegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina, P. taiwanensis.*

Another aspect of the disclosure is directed to methods of producing itaconic acid or trans-aconitate from organic compounds in an aqueous solution using a genetically-modified bacterium from the genus *Pseudomonas* described above.

In some embodiments, the organic compound is selected from aromatic compounds, saccharides, organic acids, and alcohols. In some embodiments, the organic compound is a breakdown product of lignin produced during a lignin depolymerization process. In some embodiments, the organic compound is selected from the group consisting of aromatic compounds, glycerol, diacids, fatty acids, and benzoic acid. In some embodiments, the aqueous solution is a lignin depolymerization stream or derived from a lignin depolymerization stream. In some embodiments, the lignin depolymerization stream contains p-coumaric acid, ferulic acid, and saccharides.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Definitions

Figures 1A, 1B:
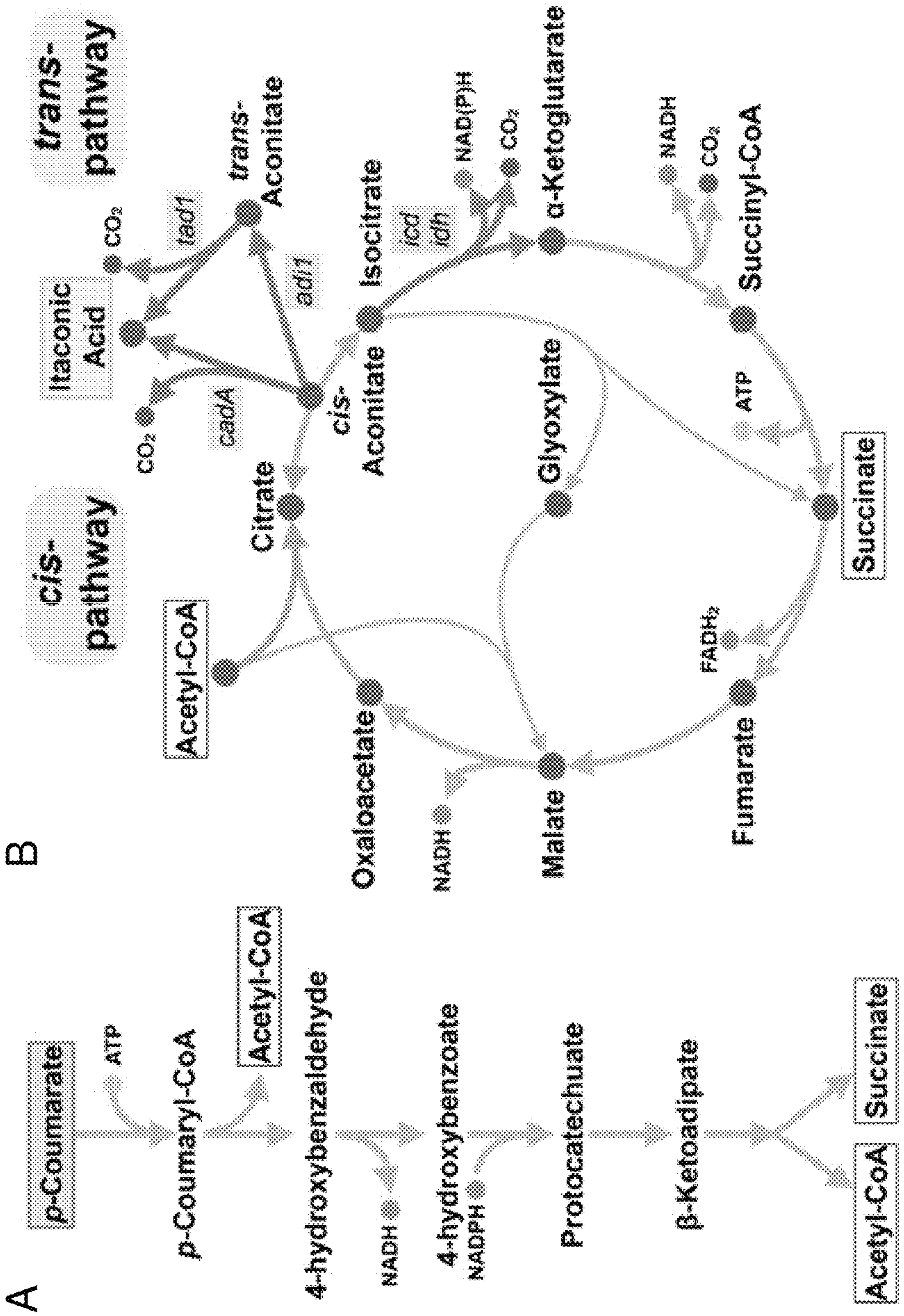
FIGS. 1A-1E. Two-stage production of itaconic acid from the lignin-derived aromatic p-coumaric acid. (A) Simplified p-coumaric acid assimilation and β-ketoadipate pathway in *Pseudomonas putida* KT2440. (B) Simplified tricarboxylic acid (TCA) cycle in *Pseudomonas putida* KT2440 with modified or heterologous steps indicated by colored arrows, and connecting metabolites outlined. For simplicity some steps are not included. The cis (red arrow) and trans (green arrow) pathways for itaconate acid are indicated with involved genes, cadA (cis) & tad1/adi1 (trans) adjacent to the reaction their gene products perform. Isocitrate dehydrogenase activity, provided by the icd & idh gene products, is indicated by a purple arrow. (C) Simplified PHA (polyhydroxyalkanoate) production pathway in *P. putida* KT2440. The PHA pathway, via fatty acid biosynthesis, competes with the TCA cycle for acetyl-CoA during nitrogen-limited conditions. (D) Production of itaconic acid from p-coumarate in shake flasks by *P. putida* strains constitutively expressing cadA under nitrogen-limited conditions. Strain name and their unique modifications are indicated above the charts. Cell density ($OD_{600}$, gray diamonds), residual p-coumaric acid (mM, blue circles), and produced itaconic acid (mM, yellow triangles) are indicated. Error bars indicate the standard deviation in three replicates. (E) Growth rates of *P. putida* strains containing icd & idh start codon mutations with or without constitutive cadA expression using p-coumarate as sole carbon source. Rates were determined by 48-well microtiter plate cultivation. Error bars indicate the standard deviation in three replicates.
Figure 1C:
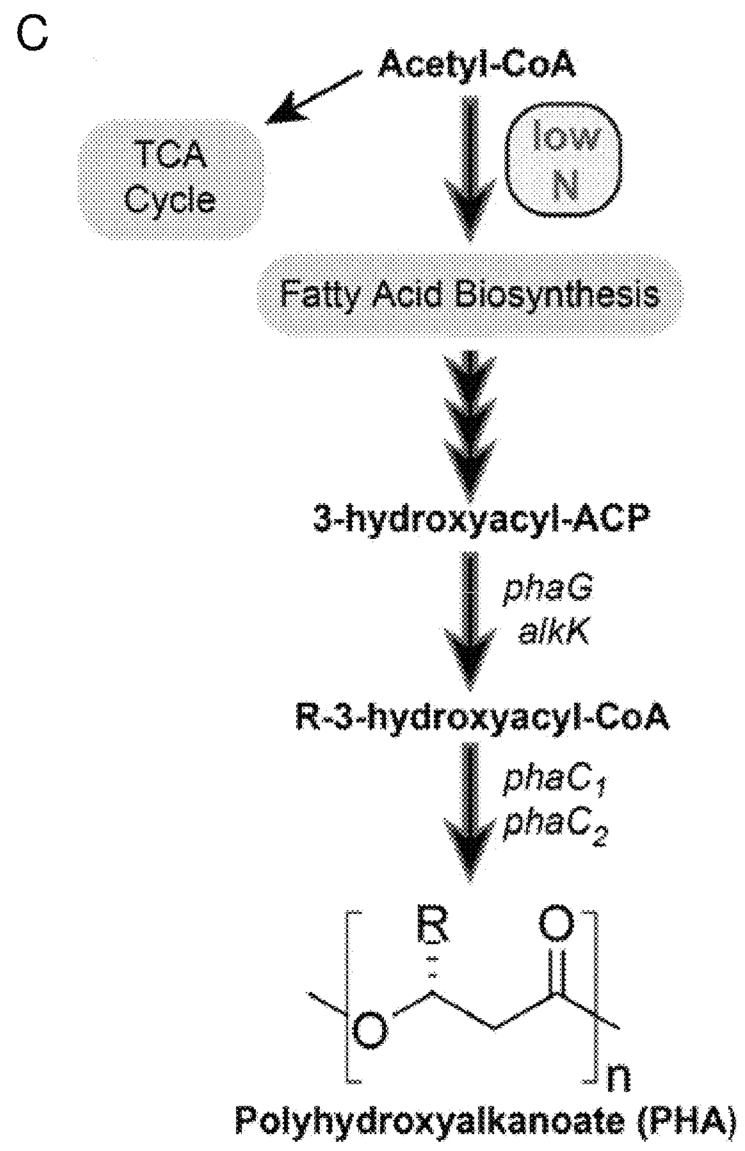

As used herein, the term "about" refers to an approximately +/−10% variation from a given value.

The term "homolog" means a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95°, 97% or 99%). A "homolog" of a protein furthermore means that the function is equivalent to the function of the original protein.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

As used herein, the term "fermentation" refers to the enzymatic and/or anaerobic breakdown of organic substances by microorganisms to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "genetically engineered" (or "genetically modified") refers to a microorganism comprising a manipulated genome or nucleic acids.

"Lignin", as used herein, refers to a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

General Description

Disclosed herein are a genetically-modified bacterium from the genus *Pseudomonas* that can produce itaconic acid or trans-aconitate and methods of producing itaconic acid or trans-aconitate using the disclosed genetically-modified bacterium.

Genetically-Modified Bacterium

In some embodiments, the present disclosure is directed to a genetically-modified bacterium from the genus *Pseudomonas* comprising an exogenous nucleic acid encoding an enzyme that uses cis-aconitate as a substrate. In some embodiments, the genetically-modified bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila. P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina, P. taiwanensis*. In a specific embodiment, the bacterium is of the species *P. putida.*

In some embodiments, the exogenous nucleic acid sequence is codon optimized for the specific *Pseudomonas* strain used. The term "codon-optimized" refers to nucleic acid molecules that are modified based on the codon usage of the host species (herein the specific *Pseudomonas* strain used), but without altering the polypeptide sequence encoded by the nucleic acid.

In some embodiments, the genetically-modified bacterium comprises an exogenous nucleic acid encoding a cis-aconitate decarboxylase (cad) enzyme. In a specific embodiment, the cad enzyme is encoded by the cad1 gene from *Aspergillus terreus* having a protein sequence as shown by SEQ ID NO: 108, or a homolog thereof. In some embodiments, the expression of the cad1 gene is dynamically regulated. In some embodiments, the dynamic regulation of cad expression comprises limiting the expression to production phase. In some embodiments, the dynamic regulation of cad1 expression is achieved by an orthogonal RNA polymerase intermediary. In a specific embodiment, the orthogonal RNA polymerase intermediary is T7pol with a nitrogen-sensitive promoter. In a specific embodiment, the nitrogen-sensitive promoter comprises a sequence selected from SEQ ID NOs: 85-89.

In some embodiments, the genetically-modified bacterium comprises an exogenous nucleic acid encoding an aconitate isomerase enzyme. In a specific embodiment, the aconitate isomerase enzyme is encoded by the adi1 gene from *Ustilago maydis* having a protein sequence as shown by SEQ ID NO: 110, or a homolog thereof. In some embodiments, the exogenous nucleic acid further encodes a trans-aconitate decarboxylase enzyme. In a specific embodiment, the aconitate isomerase enzyme is encoded by the tad gene from *Ustilago maydis* having a protein sequence as shown by SEQ ID NO: 109, or a homolog thereof.

In some embodiments, the genetically-modified bacterium comprises an exogenous nucleic acid encoding a cis-aconitate decarboxylase (cad) enzyme, an exogenous nucleic acid encoding an aconitate isomerase, and an exogenous nucleic acid encoding a trans-aconitate decarboxylase as described above.

In some embodiments, a gene encoding for a poly-hydroxyalkonate synthase enzyme, or homolog thereof, is inactivated in the bacterium. In some embodiments, all poly-hydroxyalkonate synthase enzymes, or homologs thereof are inactivated in the bacterium. In a specific embodiment, the endogenous phaC1 gene and the endogenous phaC2 gene are inactivated in the bacterium.

In some embodiments, the inactivation of the poly-hydroxyalkonate synthase gene includes a deletion of the whole or a part of the gene such that no functional protein product is expressed (also known as gene knock out). The inactivation of a gene may include a deletion of the promoter or the coding region, in whole or in part, such that no functional protein product is expressed. In other embodiments, the inactivation of poly-hydroxyalkonate synthase includes introducing an inactivating mutation to the gene, such as an early STOP codon in the coding sequence of the gene, such that no functional protein product is expressed.

In some embodiments, gene inactivation is achieved using available gene targeting technologies in the art. Examples of gene targeting technologies include the Cre/Lox system (described in Kühn, R., & M. Torres, R., *Transgenesis Techniques: Principles and Protocols*, (2002), 175-204.), homologous recombination (described in Capecchi, Mario R., *Science* (1989), 244: 1288-1292), and TALENs (described in Sommer et al., Chromosome Research (2015), 23: 43-55, and Cermak et al., *Nucleic Acids Research* (2011): gkr218.).

In one embodiment, poly-hydroxyalkonate synthase inactivation is achieved by a CRISPR/Cas system. CRISPR-Cas and similar gene targeting systems are well known in the art with reagents and protocols readily available. Exemplary genome editing protocols are described in Jennifer Doudna, and Prashant Mali, "CRISPR-Cas: A Laboratory Manual" (2016) (CSHL Press, ISBN: 978-1-621821-30-4) and Ran, F. Ann, et al. *Nature Protocols* (2013), 8 (11): 2281-2308.

In some embodiments, the genetically-modified bacterium further comprises an exogenous nucleic acid encoding a citrate synthase. In a specific embodiment, the citrate synthase enzyme is encoded by the gltA gene from *E. coli*, or a homolog thereof. In some embodiments, the exogenously-expressed citrate synthase enzyme is a mutant enzyme that is immune to allosteric inhibition by intermediates expected to accumulate during production of itaconate, such as citrate.

In some embodiments, the level of endogenous isocitrate dehydrogenase in the genetically-modified bacterium is reduced compared to a non-genetically modified bacterium. In some embodiments, the level of endogenous isocitrate dehydrogenase is reduced because transcription or translation efficiency, or stability of the isocitrate dehydrogenase mRNA is decreased. In a specific embodiment, the start codon of the endogenous isocitrate dehydrogenase gene is either "GTG" or "TTG" instead of "ATG." In some embodiments, the isocitrate dehydrogenase gene promoter comprises a mutation that decreases transcription efficiency. In some embodiments, the ribosome binding site of the isocitrate dehydrogenase gene transcript comprises a mutation that decreases the translation efficiency of the mRNA. In some embodiments, the level of endogenous isocitrate dehydrogenase is reduced because of a reduction in isocitrate dehydrogenase protein stability. In some embodiments, the isocitrate dehydrogenase protein encoded by the isocitrate dehydrogenase gene comprises a protease recognition sequence which renders it more likely to be degraded by cellular proteases.

In some embodiments, the genetically-modified bacterium is grown on an organic compound. In some embodiments, the organic compound is lignin, or a breakdown product of lignin (e.g., p-coumaric acid, ferulic acid, and saccharides). In some embodiments, the organic compound is selected from aromatic compounds, saccharides, organic acids, and alcohols. In some embodiments, the organic compound is a saccharide, not limited to a saccharide that *Pseudomonas* species can natively consume (e.g., glucose) but also one that the *Pseudomonas* species have been engineered to consume (e.g., xylose and arabinose). In some embodiments, the organic compound is an aromatic compound, and the aromatic compound comprises coumarate, ferulate, or benzoate. In some embodiments, the organic compound is an organic acid, and the organic compound comprises diacids (e.g., succinic acid), or fatty acids (e.g., acetic acid and octanoic acid). In some embodiments, the organic compound is a waste product from the production of biodiesel. In a specific embodiment, the waste product from the production of biodiesel is glycerol.

In some embodiments, the genetically-engineered bacterium further comprises an exogenous nucleic acid encoding an itaconic acid efflux pump. In some embodiments, the itaconic acid efflux pump is encoded by an itp1 gene. In a specific embodiment, the exogenous nucleic acid encodes an itp1 protein from *Ustilago maydis* having the sequence as shown in SEQ) ID NO: 111, or a homolog thereof. In some embodiments, the nucleic acid is codon optimized.

In some embodiments, the genetically-engineered bacterium further comprises an exogenous nucleic acid encoding a trans-aconitate efflux pump. In some embodiments, the itaconic acid efflux pump is encoded by a tbrB gene. In a specific embodiment, the exogenous nucleic acid encodes a TbrB protein from *Bacillus thuringiensus* CT-43 having the sequence as shown in SEQ ID NO: 112, or a homolog thereof. In some embodiments, the nucleic acid is codon optimized.

Methods for Converting an Organic Compound to Itaconic Acid or Trans-Aconitate

Another aspect of the disclosure is directed to a method for converting an organic compound to itaconic acid or trans-aconitate, the method comprising inoculating an aqueous solution containing said organic compound with a genetically-modified bacterium from the genus *Pseudomonas*, wherein the bacterium comprises an exogenous nucleic acid encoding an enzyme that uses cis-aconitate as a substrate.

In some embodiments, the genetically-modified bacterium of the claimed method is grown on an organic compound. In some embodiments, the organic compound is lignin, or a breakdown product of lignin (e.g., p-coumaric acid, ferulic acid, and saccharides). In some embodiments, the organic compound is selected from aromatic compounds, saccharides, organic acids, and alcohols. In some embodiments, the organic compound is a saccharide, not limited to a saccharide that *Pseudomonas* species can natively consume (e.g., glucose) but also one that the *Pseudomonas* species have been engineered to consume (e.g., xylose and arabinose). In some embodiments, the organic compound is an aromatic compound, and the aromatic compound comprises coumarate, ferulate, or benzoate. In some embodiments, the organic compound is an organic acid, and the organic compound comprises diacids (e.g., succinic acid), or fatty acids (e.g., acetic acid and octanoic acid). In some embodiments, the organic compound is a waste product from the production of biodiesel. In a specific embodiment, the waste product from the production of biodiesel is glycerol.

In some embodiments, the genetically-modified bacterium of the claimed method is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila. P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina, P. taiwanensis*. In a specific embodiment, the bacterium is of the species *P. putida.*

In some embodiments, the exogenous nucleic acid sequence is codon optimized for the specific *Pseudomonas* strain used. The term "codon-optimized" refers to nucleic acid molecules that are modified based on the codon usage of the host species (herein the specific *Pseudomonas* strain used), but without altering the polypeptide sequence encoded by the nucleic acid.

In some embodiments, the genetically-modified bacterium of the claimed method comprises an exogenous nucleic acid encoding a cis-aconitate decarboxylase (cad) enzyme. In a specific embodiment, the cad enzyme is encoded by the cad1 gene from *Aspergillus terreus* having a protein sequence as shown by SEQ ID NO: 108, or a homolog thereof. In some embodiments, the expression of the cad/ gene is dynamically regulated. In some embodiments, the dynamic regulation of cad1 expression comprises limiting the expression to production phase. In some embodiments, the dynamic regulation of cad1 expression is achieved by an orthogonal RNA polymerase intermediary. In a specific embodiment, the orthogonal RNA polymerase intermediary is T7pol with a nitrogen-sensitive promoter. In a specific embodiment, the nitrogen-sensitive promoter comprises a sequence selected from SEQ ID NOs: 85-89.

In some embodiments, the genetically-modified bacterium of the claimed method comprises an exogenous nucleic acid encoding an aconitate isomerase enzyme. In a specific embodiment, the aconitate isomerase enzyme is encoded by the adi1 gene from *Ustilago maydis* having a protein sequence as shown by SEQ ID NO: 110, or a homolog thereof. In some embodiments, the exogenous nucleic acid further encodes a trans-aconitate decarboxylase enzyme. In a specific embodiment, the aconitate isomerase enzyme is encoded by the tad1 gene from *Ustilago maydis* having a protein sequence as shown by SEQ ID NO: 109, or a homolog thereof.

In some embodiments, the genetically-modified bacterium of the claimed method comprises an exogenous nucleic acid encoding a cis-aconitate decarboxylase (cad) enzyme, an exogenous nucleic acid encoding an aconitate isomerase, and an exogenous nucleic acid encoding a trans-aconitate decarboxylase as described above.

In some embodiments, a gene encoding for a poly-hydroxyalkonate synthase enzyme, or homolog thereof, is inactivated in the bacterium. In some embodiments, all poly-hydroxyalkonate synthase enzymes, or homologs thereof, are inactivated in the bacterium. In a specific embodiment, the endogenous phaC1 gene and the endogenous phaC2 gene are inactivated in the bacterium.

In some embodiments, the inactivation of the poly-hydroxyalkonate synthase gene includes a deletion of the whole or a part of the gene such that no functional protein product is expressed (also known as gene knock out). The inactivation of a gene may include a deletion of the promoter or the coding region, in whole or in part, such that no functional protein product is expressed. In other embodiments, the inactivation of poly-hydroxyalkonate synthase includes introducing an inactivating mutation to the gene, such as an early STOP codon in the coding sequence of the gene, such that no functional protein product is expressed.

In some embodiments, gene inactivation is achieved using available gene targeting technologies in the art. Examples of gene targeting technologies include the Cre/Lox system (described in Kühn, R., & M. Torres, R., *Transgenesis Techniques: Principles and Protocols*, (2002), 175-204.), homologous recombination (described in Capecchi, Mario R., *Science* (1989), 244: 1288-1292), and TALENs (described in Sommer et al., Chromosome Research (2015), 23: 43-55, and Cermak et al., *Nucleic Acids Research* (2011): gkr218.).

In one embodiment, poly-hydroxyalkonate synthase inactivation is achieved by a CRISPR/Cas system. CRISPR-Cas and similar gene targeting systems are well known in the art with reagents and protocols readily available. Exemplary genome editing protocols are described in Jennifer Doudna, and Prashant Mali, "CRISPR-Cas: A Laboratory Manual" (2016) (CSHL Press, ISBN: 978-1-621821-30-4) and Ran, F. Ann, et al. *Nature Protocols* (2013), 8 (1): 2281-2308, which are incorporated in their entireties.

In some embodiments, the genetically-modified bacterium further comprises an exogenous nucleic acid encoding an exogenous nucleic acid encoding a citrate synthase. In a specific embodiment, the citrate synthase enzyme is encoded by the gltA gene from *E. coli*, or a homolog thereof. In some embodiments, the exogenously-expressed citrate synthase enzyme is a mutant enzyme that is immune to allosteric inhibition by intermediates expected to accumulate during production of itaconate, such as citrate.

In some embodiments, the level of endogenous isocitrate dehydrogenase in the genetically-modified bacterium is reduced compared to a non-genetically modified bacterium. In some embodiments, the level of endogenous isocitrate dehydrogenase is reduced because transcription or translation efficiency, or stability of the isocitrate dehydrogenase mRNA is decreased. In a specific embodiment, the start codon of the endogenous isocitrate dehydrogenase gene is either "GTG" or "TTG" instead of "ATG." In some embodiments, the isocitrate dehydrogenase gene promoter comprises a mutation that decreases transcription efficiency. In some embodiments, the ribosome binding site of the isocitrate dehydrogenase gene transcript comprises a mutation that decreases the translation efficiency of the mRNA. In some embodiments, the level of endogenous isocitrate dehydrogenase is reduced because of a reduction in isocitrate dehydrogenase protein stability. In some embodiments, the isocitrate dehydrogenase protein encoded by the isocitrate dehydrogenase gene comprises a protease recognition sequence which renders it more likely to be degraded by cellular proteases.

In some embodiments, the genetically-engineered bacterium further comprises an exogenous nucleic acid encoding an itaconic acid efflux pump. In some embodiments, the itaconic acid efflux pump is encoded by an itp1 gene. In a specific embodiment, the exogenous nucleic acid encodes an itp1 protein from *Ustilago maydis* having the sequence as shown in SEQ ID NO: 111, or a homolog thereof. In some embodiments, the nucleic acid is codon optimized.

In some embodiments, the genetically-engineered bacterium further comprises an exogenous nucleic acid encoding a trans-aconitate efflux pump. In some embodiments, the itaconic acid efflux pump is encoded by a ThrB gene. In a specific embodiment, the exogenous nucleic acid encodes a TbrB protein from *Bacillus thuringiensus* CT-43 having the sequence as shown in SEQ ID NO: 112, or a homolog thereof. In some embodiments, the nucleic acid is codon optimized.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

General Culture Conditions and Media

TABLE 1

The bacterial strains used in this study:

| Strains | Relevant Genotype |
|---|---|
| NEB 5-alpha F'Iq | *Escherichia coli* F' proA$^+$B$^+$ lacI$^q$ Δ(lacZ)M15 zzf::Tn10 (Tet$^R$)/ fhuA2Δ(argF-lacZ)U169 phoA glnV44 ΦP80Δ 'lacZ)M15 gyrA96 recA1 relA1 endA1 thi-1 hsdR17 |
| Epi400 | *Escherichia coli* F$^-$ mcrA Δ(mrr-hsdRMS-mcrBC) Φ80dlacZΔM15 ΔlacX74 recA1 endA1 araD139 Δ(ara, leu)7697 galU galK λ$^-$ rpsL (Str$^R$) nupG trfA tonA pcnB4 dhfr |
| QP15 | *Escherichia coli* F' proA$^+$B$^+$ lacI$^q$ Δ(lacZ)M15 zzf::Tn10 (Tet$^R$)/ mcrA Δ(mrr-hsdRMS-mcrBC) Φ80dlacZΔM15 ΔlacX74 recA1 endA1 araD139 Δ(ara, leu)7697 galU galK λ$^-$ rpsL (Str$^R$) nupG trfA tonA pcnB4 dhfr |
| BL21 (DE3) pLysS | *Escherichia coli* F−, ompT, hsdS$_B$ (r$_{B-}$, m$_{B-}$), dcm, gal, λ(DE3), pLysS, Cm$^r$. |
| JE90 | *Pseudomonas putida* KT2440 ΔhsdR::Bxb1int-attB |
| JE2113 | *P. putida* KT2440 ΔhsdR::Bxb1int-attB ΔampC::lysY:PurtA:T7__RNAP |
| JE3128 | *P. putida* KT2440 ΔhsdR::Bxb1int-attL:nptII:PT7:cadA:attR ΔampC::lysY:PurtA:T7__RNAP |
| JE3215 | *P. putida* KT2440 ΔhsdR::Bxb1int-attB ΔampC::lysY:PurtA:T7__RNAP ΔphaC1ZC2 |
| JE3219 | *P. putida* KT2440 ΔhsdR::Bxb1int-attL:nptII:PT7:mNeonGreen:attR ΔampC::lysY:PurtA:T7__RNAP ΔphaC1ZC2 |
| JE1622 | *P. putida* KT2440 ΔhsdR::Bxb1int-attB ΔampC::P$_{PP2685}$:T7pol |
| JE1626 | *P. putida* KT2440 ΔhsdR::Bxb1int-attB ΔampC::P$_{PP2688}$:T7pol |
| JE1629 | *P. putida* KT2440 ΔhsdR::Bxb1int-attB ΔampC::P$_{urtA}$:T7pol |
| JE1633 | *P. putida* KT2440 ΔhsdR::Bxb1int-attB ΔampC::P$_{glnK}$:T7pol |
| JE1651 | *P. putida* KT2440 ΔhsdR::Bxb1int-attL:nptII:P$_{T7}$:mNeonGreen:attR ΔampC::P$_{PP2685}$:T7pol |
| JE1652 | *P. putida* KT2440 ΔhsdR::Bxb1int-attL:nptII:P$_{T7}$:mNeonGreen:attR ΔampC::P$_{PP2688}$:T7pol |
| JE1653 | *P. putida* KT2440 ΔhsdR::Bxb1int-attL:nptII:P$_{T7}$:mNeonGreen:attR ΔampC::P$_{urtA}$:T7pol |

TABLE 1-continued

| The bacterial strains used in this study: | |
|---|---|
| Strains | Relevant Genotype |
| JE1654 | *P. putida* KT2440 ΔhsdR::Bxb1int-attL:nptII:$P_{T7}$:mNeonGreen:attR ΔampC::$P_{glnK}$:T7pol |
| JE1655 | *P. putida* KT2440 ΔhsdR:Bxb1int-attL:nptII:mNeonGreen(promoterless):attR |
| JE1657 | *P. putida* KT2440 ΔhsdR::Bxb1int-attL:nptII:$P_{T7}$:mNeonGreen:attR |
| JE2113 | *P. putida* KT2440 ΔhsdR::Bxb1int-attB ΔampC::lysY:$P_{urtA}$:T7_RNAP |
| JE2211 | *P. putida* KT2440 ΔhsdR::Bxb1int-attL:nptII:$P_{tac}$:mNeonGreen:attR ΔampC::lysY:$P_{urtA}$:T7pol |
| JE2212 | *P. putida* KT2440 ΔhsdR::Bxb1int-attL:nptII:$P_{T7}$:mNeonGreen:attR ΔampC::lysY:$P_{urtA}$:T7pol |
| JE3215 | *P. putida* KT2440 ΔhsdR::Bxb1int-attB ΔampC::lysY:$P_{urtA}$:T7pol Δ$phaC_1ZC_2$ |
| JE3221 | *P. putida* KT2440 ΔhsdR::Bxb1int-attL:nptII:PT7:cadA:attR ΔampC::lysY:PurtA:T7_RNAP ΔphaC1ZC2 |
| JE3659 | *P. putida* KT2440 ΔhsdR::Bxb1int-attL:nptII:PT7:tad1:adi1:attR ΔampC::lysY:PurtA:T7_RNAP ΔphaC1ZC2 |
| JE3674 | *P. putida* KT2440 ΔhsdR::Bxb1int-attB ΔampC::lysY:PurtA:T7_RNAP ΔphaC1ZC2 icdGTG:idhGTG |
| JE3681 | *P. putida* KT2440 ΔhsdR::Bxb1int-attB ΔampC::lysY:PurtA:T7_RNAP ΔphaC1ZC2 icdTTG:idhTTG |
| JE3712 | *P. putida* KT2440 ΔhsdR::Bxb1int-attL:nptII:PT7:mNeonGreen:attR ΔampC::lysY:PurtA:T7_RNAP ΔphaC1ZC2 icdGYG:idhGYG |
| JE3713 | *P. putida* KT2440 ΔhsdR::Bxb1int-attL:nptII:PT7:cadA:attR ΔampC::lysY:PurtA:T7_RNAP ΔphaC1ZC2 icdGTG:idhGTG |
| JE3715 | *P. putida* KT2440 ΔhsdR::Bxb1int-attL:nptII:PT7:tad1:adi1:attR ΔampC::lysY:PurtA:T7_RNAP ΔphaC1ZC2 icdGTG:idhGYG |
| JE3716 | *P. putida* KT2440 ΔhsdR::Bxb1int-attL:nptII:PT7:mNeonGreen:attR ΔampC::lysY:PurtA:T7_RNAP ΔphaC1ZC2 icdTTG:idhTTG |
| JE3717 | *P. putida* KT2440 ΔhsdR::Bxb1int-attL:nptII:PT7:cadA:attR ΔampC::lysY:PurtA:T7_RNAP ΔphaC1ZC2 icdTTG:idhTTG |
| JE3719 | *P. putida* KT2440 ΔhsdR::Bxb1int-attL:nptII:PT7:tad1:adi1:attR ΔampC::lysY:PurtA:T7_RNAP ΔphaC1ZC2 icdTTG:idhTTG |
| JE3899 | *P. putida* KT2440 ΔhsdR::Bxb1int-attL:nptII:PT7:adi1:attR ΔampC::lysY:PurtA:T7_RNAP ΑphaC1ZC2 icdTTG:idhTTG |
| JE3729 | *P. putida* KT2440 ΔhsdR::Bxb1int-attL:nptII:$P_{T7}$:mKate2:attR ΔampC::lysY:$P_{urtA}$:T7pol |
| JE3730 | *P. putida* KT2440 ΔhsdR::Bxb1int-attL:nptII:$P_{T7\_C4}$:mKate2:attR ΔampC::lysY:$P_{urtA}$:T7pol |
| JE3732 | *P. putida* KT2440 ΔhsdR::Bxb1int-attL:nptII:$P_{T7\_H10}$:mKate2:attR ΔampC::lysY:$P_{urtA}$:T7pol |
| JE3734 | *P. putida* KT2440 ΔhsdR::Bxb1int-attL:nptII:$P_{T7\_H9}$:mKate:attR ΔampC::lysY:$P_{urtA}$:T7pol |
| JE3736 | *P. putida* KT2440 ΔhsdR:Bxb1int-attL:nptII:$P_{T7\_G6}$:mKate2:attR ΔampC::lysY:$P_{urtA}$:T7pol |
| JE3738 | *P. putida* KT2440 ΔhsdR::Bxb1int-attL:nptII:$P_{tac}$:mKate2:attR ΔampC::lysY:$P_{urtA}$:T7pol |
| JE669 | *P. putida* KT2440 ΔhsdR::Bxb1int-attB Δ$phaC_1ZC_2$ |
| JE4296 | *P. putida* KT2440 ΔhsdR::Bxb1int-attB Δ$phaC_1ZC_2$ $icd^{GTG}$:$idh^{GTG}$ |
| JE4273 | *P. putida* KT2440 ΔhsdR::Bxb1int-attB Δ$phaC_1ZC_2icd^{TTG}$:$idh^{TTG}$ |
| JE4305 | *P. putida* KT2440 ΔhsdR::Bxb1int-attL:nptII:$P_{tac}$:cadA:attR |
| JE4306 | *P. putida* KT2440 ΔhsdR::Bxb1int-attL:nptII:$P_{tac}$:cadA:attR Δ$phaC_1ZC_2$ |
| JE4307 | *P. putida* KT2440 ΔhsdR::Bxb1int-attL:nptH:$P_{rac}$.cafiM.att7? Δ$phaC_1ZC_2icd^{TTG}$:$idh^{TTG}$ |

TABLE 2

| Plasmids used in this study: | |
|---|---|
| Plasmids | |
| pJE382 | pUC origin, nptII, sacB, mcs-lacZa |
| pK18mobsacB | pUC origin, nptII, sacB, Plac:mcs-lacZa |
| pLysS | p15A origin, cat, lysS |
| pJE990 | pUC origin, nptII, mNeonGreen (promoterless) |
| pJE387 | pK18mobsacB ΔampC |
| pJE473 | pJE382 ΔphaC1ZC2 |
| pJE1031 | pJE382 ΔampC |

TABLE 2-continued

| Plasmids used in this study: | |
|---|---|
| Plasmids | |
| pJE1037 | pJE382 ΔampC::PurtA:T7_RNAP |
| pJE1040 | pJE990 PT7:mNeonGreen |
| pJE1180 | pJE382 ΔampC::lysY:PglnK:T7_RNAP |
| pJE1380 | pJE990 PT7:cadA |
| pJE1443 | pJE990 PT7:tad1:adi1 |
| pJE1444 | pJE382 icdGTG:idhGTG |

TABLE 2-continued

| Plasmids used in this study: | |
|---|---|
| Plasmids | |
| pJE1445 | pJE382 icdTTG.idhTTG |
| pJE1383 | pJE990 PT7:adi1 |

Routine cultivation of *Escherichia coli* for plasmid construction and maintenance was performed at 37° C. using LB (Miller) medium supplemented with 50 μg/mL kanamycin sulfate and 15 g/L agar (for solid medium). All *Pseudomonas putida* cultures were incubated at 30° C., with shaking at 250 rpm for liquid cultures. LB (Miller) was used for routine *Pseudomonas putida* strain maintenance, competent cell preparations, and starter cultures. For itaconate production assay starter cultures, the media was supplemented with 50 μg/mL kanamycin sulfate.

Modified M9 medium (M9*) with variable amounts of $NH_4Cl$ was utilized for shake flask experiments, growth rate assays, and fluorescent reporter assays (47.8 mM Na2HPO4, 22 mM KH2PO4, 8.6 mM NaCl, 1 mM MgCl2, 0.1 mM $CaCl_2$, 18 μM FeSO4, 1×MME trace minerals, pH adjusted to 7 with KOH). 1000×MME trace mineral stock solution contains per liter, 1 mL concentrated 1-HCl, 0.5 g $Na_4EDTA$, 2 g $FeCl_3$, 0.05 g each $H_3BO_3$, ZnClz, $CuCl_2.2H_2O$, $MnCl_2.4H_2O$, $(NH_4)_2MoO_4$, $CoCl_2.6H_2O$, $NiCl_2.6H_2O$. Unless otherwise noted, all M9* medium was supplemented with 20 mM p-coumarate (neutralized with NaOH) as a sole carbon source.

Production of Base-Catalyzed Depolymerized (BCD) Lignin (BCDL) and Depolymerized Lignin Media Preparation In brief, dry solid material remaining from the enzymatic hydrolysis of pretreated corn stover (which follows the biorefinery process designed at NREL) was added as 10% (w/v) solids to a 2% NaOH solution and loaded into 200 mL stainless steel reactors. The reaction was carried out at 120° C. for 30 min. The sterile and solubilized material was neutralized with 4N $H_2SO_4$ and centrifuged at 8,000 rpm for 20 min in aseptic conditions. Then, the supernatant (90% v/v) was mixed with 10×M9* salts (without any nitrogen source) and $NH_4Cl$ to generate M9*-BCDL medium supplemented with either 2 mM or 3 mM $NH_4Cl$.

Plasmid & *Pseudomonas* Strain Construction

Phusion® HF Polymerase (Thermo Scientific) and primers synthesized by Eurofins

Genomics were used in all PCR amplifications for plasmid construction. OneTaq® (New England Biolabs—NEB) was used for colony PCR. Plasmids were constructed by Gibson Assembly using NEBuilder® HiFi DNA Assembly Master Mix (NEB) or ligation using T4 DNA ligase (NEB). Plasmids were transformed into either competent NEB 5-alpha F'I$^q$ (NEB), Epi400 (Lucigen), or QP15 (Epi400 mated with NEB 5-alpha F'I$^q$ to transfer the mini F' plasmid to Epi400). Standard chemically competent *Escherichia coli* transformation protocols were used to construct plasmid host strains. Transformants were selected on LB (Miller) agar plates containing 50 pig/mL kanamycin sulfate for selection and incubated at 37° C., Template DNA was either synthesized by IDT or isolated from *E. coli* or *P. putida* KT2440 using Zymo Quick gDNA miniprep kit (Zymo Research). Zymoclean Gel DNA recovery kit (Zymo Research) was used for all DNA gel purifications. Plasmid DNA was purified from *E. coli* using GeneJet plasmid miniprep kit (ThermoScientific) or ZymoPURE plasmid midiprep kit (Zymo Research). Sequences of all plasmids were confirmed using Sanger sequencing performed by Eurofins Genomics. Plasmids used in this work are listed in Table 2.

*P. putida* JE90, a derivative of *P. putida* KT2440 where the restriction endonuclease hsdR has been replaced with the Bxb1-phage integrase and respective attB sequence (Elmore, J R., et al., *Metabolic Eng. Comm.,* 5 (2017): 1-8), was used as a parent for all *P. putida* strains used in this study (Table 1). All genome modifications were performed using either the homologous recombination-based pK18mobsacB kanamycin resistance/sucrose sensitivity selection/counter-selection system (Marx, C J., *BMC research notes* 1.1 (2008): 1) as described in detail previously (Johnson, C W. et al., *Metabolic Eng.,* 28 (2015): 240-247) or with the Bxb1-phage integrase system (Elmore, J R., et al., *Metabolic Eng. Comm.,* 5 (2017): 1-8) with minor modifications to competent cell preparation procedures. These modifications cultivation overnight to stationary phase, rather than harvesting during exponential growth and all wash steps were performed at room temperature rather than at 4° C. Gene deletions and replacements were performed by homologous recombination, while integration of reporter and itaconate production pathway cassettes was performed with the Bxb1-phage integrase system. Primers used for screening *P. putida* strains for phaC1ZC2 deletion, ampC::T7_RNAP replacements, and icd/idh start codon swaps can be found below. Integration of pJE990-derivatives using the phage integrase system was confirmed by colony PCR using oligos oJE66 & oJE535.

Plasmid Construction Details

All enzymes used for plasmid construction were purchased from NEB.

For construction of pJE473 (SEQ ID NO: 91), homology arms to target deletion of phaC1ZC2 (PP_5003-5005) were amplified by PCR from wild-type *P. putida* genomic DNA using primer combinations oJE331/332 and oJE333/334, assembled into gel purified EcoRI/HindIII-linearized pJE382, and transformed into NEB 5-alpha F'I$^Q$. Resulting *E. coli* colonies were screened by colony for the presence of homology arms using primers oJE255/256. Candidates for pJE473 were purified from *E. coli* and sequenced using primers oJE255/256.

For construction of pJE1031 (SEQ ID) NO: 93), homology arms for the deletion of ampC (PP_2876) were amplified from pJE387 (SEQ ID NO: 90) using primer combination oJE92/608, assembled into gel purified EcoRI/HindIII-linearized pJE382, and transformed into NEB 5-alpha F'I$^Q$. Resulting *E. coli* colonies were screened by colony for the presence of homology arms using primers oJE255/256. Candidates for pJE1031 were purified from *E. coli* and sequenced using primers oJE255/256.

For construction of pJE1032 (SEQ ID NO: 94), pJE1033 (SEQ ID NO: 95), pJE1037 (SEQ ID NO: 96), and pJE1039 (SEQ ID NO: 97), promoter sequences containing ~200-300 bp upstream of PP_2685, PP_2688, urtA (PP_4841), and glnK (PP_5234), respectively, were amplified from *P. putida* and assembled with T7 RNAP and a synthetic terminator sequence. The T7 RNA P polymerase and a downstream terminator was amplified from BL21(DE3) pLysS genomic DNA using oligos oJE625/626. A double terminator sequence for insulation of the construct was amplified from the T7_dbl_term gBlock using oJE627/628. Parts were assembled into BamHI/XbaI-linearized pJE1031, and transformed into NEB 5-alpha F'I$^Q$. Resulting *E. coli* colonies were screened by colony PCR using primers oJE177/178.

Candidates for the plasmids were purified from *E. coli* and sequenced using oJE177/178/631/632/633.

For construction of the reporter plasmids the inventors annealed oligos containing desired promoter sequences and ligated the promoters into a promoterless mNeonGreen reporter plasmid, pJE990 (SEQ ID NO: 92). Plasmid pJE990 was linearized with BbsI. Promoter oligos pairs were phosphorylated with PNK (NEB) in T4 DNA ligase buffer, annealed by heating to 95° C. and cooling at 1° C./minute to room temperature. Annealed oligo sets oJE634/635, oJE97/98/133/134, oJE826/827, oJE828/829, oJE830/831, and oJE832/833 were ligated to BbsI-linearized pJE990 to construct plasmids pJE1040 (SEQ ID NO: 98), pJE1045, pJE1118, pJE1119, pJE1120, and pJE1121 respectively. Ligated DNA was transformed into NEB 5-alpha F'IQ. Plasmids were isolated from transformant colonies and confirmed by sequencing with oJE535. For construction of mKate2 variant plasmids, mKate2 was amplified from the mKate2 gBlock using oligos oJE1724/1725 and digested with NdeII/XbaI. Plasmids pJE1040 and pJE1118-1121 were digested with NdeI/XbaI and ligated with NdeI/XbaI digested mKate2 gBlock to generate plasmids pJE1454-1458. Ligations were transformed into NEB 5-alpha F'IQ, and candidates confirmed by sequencing of isolated plasmid DNA using oligos oJE535/536.

For construction of pJE1180 (SEQ ID NO: 99), the inventors amplified the cat and lysS genes from pLysS as two parts with primers designed to introduce the lysY mutation, assembled the resulting parts into SpeI-linearized pJE1040. Primers oJE817/818 and oJE819/820 were used to amplify the two parts. The resulting lysY/cat fragment was digested with SpeI and ligated into XbaI-linearized pJE1037, generating plasmid pJE1180.

For construction of pJE1380 (SEQ ID NO: 100), codon-optimized cadA from *Aspergillus terreus* was assembled into NdeI/XbaI-linearized pJE1040—replacing mNeonGreen. The cadA gene was synthesized as gBlocks "cadA_gBlock_1" & "cadA_gBlock_2", gBlocks 1 & 2 were amplified using oligos oJE1408/1409 and oJE1410/1411, respectively. The assembly was transformed into NEB 5-alpha F'I$^{Q}$, and transformants were screened using oJE535/536. Plasmid DNA was isolated from PCR positive candidates, and sequenced using oJE535/536/1412.

For pJE1390, the cadA gene (encoding the cadA protein shown as SEQ ID NO: 108) from pJE1380 was excised using NdeI/XbaI, and ligated into NdeI/XbaI linearized pJE1045. The ligation was transformed into QP15, and transformants were screened by colony PCR using oligos oJE535/536. The assembly was transformed into NEB 5-alpha F'I$^{Q}$, and transformants were screened using oJE535/536. Plasmid DNA was isolated from PCR positive candidates, and sequenced using oJE535/536/1412.

For pJE1443 (SEQ ID) NO: 101), codon-optimized tad1 and adi1 genes from *Ustilago maydis* were assembled into AflIII/XbaI-linearized pJE1040—replacing mNeonGreen and its RBS sequence. The tad1 and adi1 (SEQ ID NO: 107) genes were synthesized as gBlocks "tad1" and "adi1", which were amplified using primer combinations oJE1554/1547 and oJE1555/1548, respectively. The assembly was transformed into NEB 5-alpha F'I$^{Q}$, and transformants were screened using oJE535/536. Plasmid DNA was isolated from PCR positive candidates, and sequenced using oJE535/536/1559/1560/1561.

For pJE1483 (SEQ ID NO: 104), codon-optimized adi1 gene (SEQ ID NO: 107) used for pJE1443 was assembled into AflIII/XbaI-linearized pJE1040—replacing mNeonGreen and its RIBS sequence. The adi1 sequence and its RIBS was amplified from pJE1443 using oligos oJE1760/1761. The assembly was transformed into NEB 5-alpha F'I$^{Q}$, and transformants were screened using oJE535/536. Plasmid DNA was isolated from PCR positive candidates, and sequenced using oJE535/536/1561.

For the construction of the icd/idh start codon swap plasmids pJE1444 (SEQ ID NO: 102) and pJE1445 (SEQ ID NO: 103), several PCR reactions were assembled containing homology arms for targeting, and mutations in the start codons (and RBS neutral mutations in the region between core RBS and start codon) of icd & idh. The homology arms for targeting insertion of the two plasmids into the icd idh locus were amplified using primer pairs oJE1564/1565 and oJE1568/1569 for both plasmids. The central fragment contained between the two homology arms, containing the various mutations, was amplified using oligos oJE1566/1567 for pJE1444 and oligos oJE1570/1571 for pJE1445. The parts were assembled into EcoRI/HindIII-linearized pJE382, transformed into NEB 5-alpha F'I$^{Q}$, and transformants were screened using oJE255/256. Plasmid DNA was isolated from PCR positive candidates, and sequenced using oJE1255/256/1572/1573.

TABLE 3

Oligos used in the disclosure:

| Oligo Name | Oligo Sequence (5'-3') | Purpose |
|---|---|---|
| oJE255 | attaatgcagctggcacgac (SEQ ID NO: 1) | primers for screening insertions into the MCS of pJE382 |
| oJE256 | agctagatatcgccattcg (SEQ ID NO: 2) | primers for screening insertions into the MCS of pJE382 |
| oJE331 | tagctcactcaggaaacagctatgacatgattac gaattcGACCGAAAACATCGGTGC (SEQ ID NO: 3) | amplification of homology arms to construction pJE473 for deletion of phaC1ZC2 |
| oJE332 | tcagcacgtaggtgcctTCTAGAgtctattgtaGG ATCCTCTACGACGCTCCGTTG (SEQ ID NO: 4) | amplification of homology arms to construction pJE473 for deletion of phaC1ZC2 |
| oJE333 | aCAACGGAGCGTCGTAGAGGATCC tacaatagacTCTAGAAGGCACCTACG TGCTG (SEQ ID NO: 5) | amplification of homology arms to construction pJE473 for deletion of phaC1ZC 2 |

TABLE 3 -continued

Oligos used in the disclosure:

| Oligo Name | Oligo Sequence (5'-3') | Purpose |
|---|---|---|
| oJE334 | ccagtcacgacgttgtaaaacgacggccagtgccaagcttGCAGCCAAAACCGCAG (SEQ ID NO: 6) | amplification of homology arms to construction pJE473 for deletion of phaC1ZC2 |
| oJE335 | cagtaccaggcattgctgaa (SEQ ID NO: 7) | screening deletion of phaC1ZC2 (flanking) |
| oJE336 | gccaaggcagcagctaag (SEQ ID NO: 8) | screening deletion of phaC1ZC2 (flanking) |
| oJE337 | TGGAGCIGAAGAACGIGTTG (SEQ ID NO: 9) | screening deletion of phaC1ZC2 (internal to phaG) |
| oJE338 | CTCGTCGACAAACAAAGCAA (SEQ ID NO: 10) | screening deletion of phaC1ZC2 (internal to phaG) |
| oJE92 | ccagtcacgacgttgtaaaacgacggccagtgccaagcttGTAACCACGGCCICACTGAA (SEQ ID NO: 11) | amplification of ampC deletion homology arms for construction of pJE1031 |
| oJE608 | tagctcactcaggaaacagctatgacatgattacgaattcCTTGCCTCTGCCGGAAAC (SEQ ID NO: 12) | amplification of ampC deletion homology arms for construction of pJE1031 |
| oJE609 | CTGTCGTTTTGTCCGACAATCAACGCGAGCGttaggatccCATCGCCAGTGACAGACTG (SEQ ID NO: 13) | Amplifies PP_2685 promoter with overlaps to construct pJE1032 |
| oJE610 | TGTCAGAGAAGTCGTTCTTAGCGATGTTAATCGTGTTCATGCGGTTTCCCTTGTGTIG (SEQ ID NO: 14) | Amplifies PP_2685 promoter with overlaps to construct pJE1032 |
| oJE611 | CTGTCGTTTTGTCCGACAATCAACGCGAGCGttaggatccGCCCGGGTCAAAAGCCTTGTCAGAGAAGTCGTTCTTAGCGATGTT (SEQ ID NO: 15) | Amplifies PP_2688 promoter with overlaps to construct pJE1033 |
| oJE612 | AATCGTGTTCATACCCACTCCTTGCCGCCGTT (SEQ ID NO: 16) | Amplifies PP_2688 promoter with overlaps to construct pJE1033 |
| oJE619 | CTGTCGTTTTGTCCGACAATCAACGCGAGCCTttaggatccATGGCCTCGGGGGCTGTTGTCAGAGAAGTCGTTCTTAGCGATGTT (SEQ ID NO: 17) | Amplifies PP_4841 promoter with overlaps to construct pJE1037 |
| oJE620 | AATTCGTGTTCATGTGCTCTCTCCGCTGAGT (SEQ ID NO: 18) | Amplifies PP_4841 promoter with overlaps to construct pJE1037 |
| oJE623 | CTGTCCITTFIGTCCGACA,ATCAikCGCGAGCGttaggatccGCTGCGCACCGAAATTG (SEQ ID NO: 19) | Amplifies PP_5234 promoter with overlaps to construct pJE1039 |
| oJE624 | TGTCAGAGAAGTCGTTCTTAGCGATGTTAATCGTGTTCATGAAACTCTCTCCCGATTTGG (SEQ ID NO: 20) | Amplifies PP_5234 promoter with overlaps to construct pJE1039 |
| oJE625 | ATGAACACGATTAACATCGCTAAG (SEQ ID NO: 21) | amplification of T7 RNAP for construction of pJE1032, 1033, 1037, 1039 |
| oJE626 | GTAAAAKFTGCcATccCAACAGC (SEQ ID NO: 22) | amplification of T7 RNAP for construction of pJE1032, 1033, 1037, 1039 |
| oJE627 | GAGCATCAATATGCAATGCTGTTG (SEQ ID NO: 22) | amplification of double terminator from Dbl_term_T7 gBlock for construction of pJE1032, 1033, 1037, 1039 |
| oJE628 | CGCTCAACGGACACGCT (SEQ ID NO: 24) | amplification of double terminator Dbl_term_T7 gBlock for construction of pJE1.032, 1033, 1037, 1039 |

TABLE 3 -continued

Oligos used in the disclosure:

| Oligo Name | Oligo Sequence (5'-3') | Purpose |
|---|---|---|
| oJE629 | GACCATTACGGTGAGCGTTT (SEQ ID NO: 25) | Amplifies an internal fragment of T7 RNAP for PCR screening |
| oJE630 | CGGGTTGAACATTGACACAG (SEQ ID NO: 26) | Amplifies an internal fragment of T7 RNAP |
| oJE631 | CTCAACAAGCGCGTAGG (SEQ ID NO: 27) | Internal sequencing primer for T7 RNAP gene |
| oJE632 | GTTCATGCTTGAGCAAGCC (SEQ ID NO: 28) | internal sequencing primer for T7 RNAP gene |
| oJE633 | GGTGTTACTCGCAGTGTGAC (SEQ ID NO: 29) | Internal sequencing primer for T7 RNAP gene |
| oJE634 | gtctTAATACGACTCACTATAGGGA GAGACCTGGAATTGTGAGCGGAT AACAATT (SEQ ID NO: 30) | Anneal with oJE634 to construct T7 promoter for cloning of pJE1040 |
| oJE635 | taagAATTGTTATCCGCTICACAATFC CAGGTCTCTCCCTATAGTGAGTCG TATTA (SEQ ID NO: 31) | Anneal with oJE635 to construct T7 promoter for cloning of pJE1040 |
| oJE535 | GTTgctagcGTCGGGGTTTGTA (SEQ ID NO: 32) | Screening of genomic integration of pJE990/991 and its derivatives into JE90 derivative strains, as well as plasmid sequencing |
| oJE536 | aaaaccgcccagtctagctatcg (SEQ ID NO: 33) | Screening of genomic integration of pJE990/991 and its derivatives into JE90 derivative strains, as well as plasmid sequencing |
| oJE93 | GGCGTTGCTGGAAGAGTATT (SEQ ID NO: 34) | flanking primers for screening ampC deletion |
| oJE94 | ACCACTGCCAGCAGAATTG (SEQ ID NO: 35) | flanking primers for screening ampC deletion |
| oJE546 | gctgttgccatcgatcagt (SEQ ID NO: 36) | amplifies internal 851 bp fragment of ampC. Used for screening deletion. |
| oJE547 | acgaccagttacaggccaag (SEQ ID NO: 37) | amplifies internal 851 bp fragment of ampC. Used for screening deletion. |
| oJE177 | GGGAGACGGCTTCATCATG (SEQ ID NO: 38) | Amplifies sequence inserted btw homology arms of pJE387/1031 |
| oJE178 | ATCACTGTATCCATCTTGTCATG (SEQ ID NO: 39) | Amplifies sequence inserted btw homology arms of pJE387/1031 |
| oJE826 | gtctTAKIACGACTCACTAtcaaggaaG ACCTGGAATTGTGAGCGGATAAC AATT (SEQ ID NO: 40) | cloning T7_C4 promoter into pJE990 |
| oJE827 | taagAATTTGTTATCCGCTCACAATTC CAGGTCttccttgaTAGTGAGTCGTAT TA (SEQ ID NO: 41) | cloning T7_C4 promoter into pJE990 |
| oJE828 | gtoTAATACGACTCACTAcggaagaaG ACCIGGNATTGTGAGCGGATAAC AATT (SEQ ID NO: 42) | cloning T7_H10 promoter into pJE990 |
| oJE829 | taagAATTGTTATCCGCTCACAATIC CAGGTCttcttccgTAGTGAGTCGTAT TA (SEQIvD NO: 43) | cloning T7_H10 promoterinto pJE990 |
| oJE830 | gtctTAATACGACTCACTAatactgaaGA CCTGGAATTGTGAGCGGATAACA ATT (SEQ ID NO: 44) | cloning T7_H9 promoter into pJE990 |

TABLE 3 -continued

Oligos used in the disclosure:

| Oligo Name | Oligo Sequence (5'-3') | Purpose |
|---|---|---|
| oJE831 | taagAATTTGTTATCCGCTCACAAVIC CAGGTCttcagtatTAGTGAGTCGTAT TA (SEQ ID NO: 45) | cloning T7_H9 promoter into pJE990 |
| oJE832 | gtctTAATACGACTCACTAtttcggaaGA CCTGGAATTGTGAGCGGATAACA ATT (SEQ ID NO: 46) | cloning T7_G6 promoter into pJE990 |
| oJE833 | taagAATTGTTATCCGCTCACAATTC CAGGTCttccgaaaTAGTGAGTCGTAT TA (SEQ ID NO: 47) | cloning T7_G6 promoter into pJE990 |
| oJE817 | cccgaaaggggggcctatttcgttttggtcca ctagtCACTATCGACTACGCGATCATG (SEQ ID NO: 48) | amplify part of pLysS for construction of pJE1110 |
| oJE818 | GAAGGCGCTGGTCTTCGCGCCCAT CATGAGGTGGCGCCGTACGCTTGC CCTTCGTTCGAC (SEQ ID NO: 49) | amplify part of pLysS for construction of pJE1110 |
| oJE819 | TCTCCCACCAACGCTTAAGGTCGA ACGAAGGGCAAGCGTACGGCGCC ACCTCATGAT (SEQ ID NO: 50) | amplify part of pLysS for construction of pJE1110 |
| oJE820 | CAGGTCTCTCCCTATAGTGAGTCG TATTAagactactagtCCTGITGATACC GGGAAGC (SEQ ID NO: 51) | amplify part of pLysS for construction of pJE1110 |
| oJE821 | TCACGGACACCAACATTCTGAC (SEQ ID NO: 52) | sequencing of LysY fragment of pJE1180 |
| oJE1408 | GATAACAATTcttaagattaactcacacagga gatatcat (SEQ ID NO: 53) | amplification of cadA gBlocks for pJE1380 construction |
| oJE1409 | CCTTTGGTAAACATTTTCAGAAAAC C (SEQ ID NO: 54) | amplification of cadA gBlocks for pJE1380 construction |
| oJE1410 | GAACGCAGCTATGGGGGTTTTCTG (SEQ ID NO: 55) | amplification of cadA gBlocks for pJE1380 construction |
| oJE1411 | AAGGCCCCCCGTTAGGGAGGCCT TATTGTTCGTCtctagaTTAGACCAA GG (SEQ ID NO: 56) | amplification of cadA gBlocks for pJE1380 construction |
| oJE1412 | TGCATAGCGCAAGCATTGTG (SEQ ID NO: 57) | sequencing of cadA in pJE1380 |
| oJE1547 | ATTCTAGGCACTGCTGTACTGATA GGGTATTCACGCCGACGATGGAC (SEQ ID NO: 58) | amplification of tad1 gBlock for assembly of pJE1443 |
| oJE1548 | CGTGTGTTGAGCCGTCCATCGTCG GCGTGAATACCCTATCAGTACAGC AGTG (SEQ ID NO: 59) | amplification of adi1 gBlock for assembly of pJE1443 |
| oJE1554 | TGGAATTGTGAGCGGATAACAAT TcttaagGTagaTaAGAGCGGGTCATC G (SEQ ID NO: 60) | amplification of tad1 gBlock for assembly of pJE1443 |
| oJE1555 | GTTAGGGAGGCCTTATTGTTCGTCt ctagaTCAGGACAAGCTCCGGTC (SEQ ID NO: 61) | amplification of adi1 gBlock for assembly of pJE1443 |
| oJE1559 | AGCAACGGITGGATAGCATC (SEQ ID NO: 62) | sequencing of tad1 |
| oJE1560 | CAGGTCTTTCCCGATGCAAT (SEQ ID NO: 63) | sequencing of tad1 downstream genes |
| oJE1561 | AACCGCATCCGTCCGATA (SEQ ID NO: 64) | sequencing of adi1 |
| oJE1564 | cactcaggaaacagctatgacatgattac gaattcgccgccatcaagcagtt (SEQ ID NO: 65) | amplification of UP homology arm for pJE1444/1445 construction |

TABLE 3 -continued

Oligos used in the disclosure:

| Oligo Name | Oligo Sequence (5'-3') | Purpose |
|---|---|---|
| oJE1565 | ggataccagaaaatcaaggttccga (SEQ ID NO: 66) | amplification of UP homology arm for pJE1444/1445 construction |
| oJE1566 | tcggaaccttgattttctggtatccCACC GAAgcactactccgctgtcg (SEQ ID NO: 67) | amplification of icd/idh promoter region with GTG start codons for pJE1444 construction |
| oJE1567 | tatagatgatcttggaacgggtgggCACg TTTgttaactactgtgtgctgagc (SEQ ID NO: 68) | amplification of icd/idh promoter region with GTG start codons for pJE1444 construction |
| oJE1568 | cccacccgttccaagatcat (SEQ ID NO: 69) | amplification of DN homology arm for pJE1444/1445 construction |
| oJE1569 | cacgacgttgtaaaacgacggccagtgccaagct taacatgatcgggtcgga (SEQ ID NO: 70) | amplification of DN homology arm for pJE1444/1445 construction |
| oJE1570 | tcggaaccttgattactggtatccCAACGAAgca ctactccgctgtcg (SEQ ID NO: 71) | amplification of icd/idh promoter region with TTG start codons for pJE1445 construction |
| oJE1571 | tatagatgatcttggaacgggtgggCAAgTTTgtt aactctctgtgtgagagc (SEQ ID NO: 72) | amplification of icd/idh promoter region with TTG start codons for pJE1445 construction |
| oJE1572 | cgataccacataatcacgcac (SEQ ID NO: 73) | sequencing of pJE1444/1445 |
| oJE1573 | ctctcgactttccgctca (SEQ ID NO: 74) | sequencing of pJE1444/1445 |
| oJE1574 | ttttaggtatccCACCGAA (SEQ ID NO: 75) | screening for GTIG start codon swap for icd/idh in *P. putida* |
| oJE1575 | gggtgggCACgTTT (SEQ ID NO:7 6) | screening for GTG start codon swap for icd/idh in *P. putida* |
| oJE1576 | gatctggtatccCAACGAA (SEQ ID NO: 77) | screening for TTG start codon swap for icd/idh in *P. putida* |
| oJE1577 | cgggtgggCAAgTTT (SEQ ID NO: 78) | screening for TTG start codon for icd/idh in *P. putida* |
| oJE1578 | gattttctggtatcccatgct (SEQ ID NO: 79) | screening for wild-type start codon |
| oJE1579 | gtgggcatgcgg (SEQ ID NO: 80) | screening for wild-type start codon |
| oJE1580 | gtggcgatcacgtcgtact (SEQ ID NO: 81) | screening to ensure that plasmid backbone is removed following start codon swap |
| oJE1581 | aggaggtgatgcctttgtc (SEQ ID NO: 82) | screening to ensure that plasmid backbone is removed following start codon swap |
| oJE1582 | aggaatgatcggaggtcag (SEQ ID NO: 83) | sequencing of icd promoter region. Use with oJE1581 to amplify region for sequencing. |
| oJE66 | catgtagttgtaggcgtcttc (SEQ ID NO: 84) | screening integration of pJE990-derivative plasmids via the Bbx1-phage integrase system |

Growth Rate Analysis

LB medium was inoculated from glycerol stocks and incubated overnight at 30° C., 250 rpm for precultures. Cultures were washed twice by centrifugation (~4000×g for 10 minutes) and resuspension in equal volumes of 1×M9 salts lacking $NH_4Cl$ to remove residual LB medium, and resuspended in ⅓ volume 1×M9 salts. Optical density (OD600) of resulting suspensions was measured using a 1 cm path length cuvette. Growth assays were performed with 600 µL M9* medium supplemented with 20 mM p-coumarate and 20 mM $NH_4Cl$ in clear 48-well microtiter plates with an optically clear lid (Greiner Bio-One). All cultures were inoculated with washed cultures to an $OD_{600}$ equivalent to 0.03 in a 1 cm pathlength cuvette. Plates were incubated at 30° C., fast shaking in an Epoch2 plate reader (Bio-Tek), with $OD_{600}$ readings taken every 10 minutes. Exponential growth rates were determined using the CurveFitter software with data points in early mid-log phase. All growth rates were calculated from 3 replicate experiments.

Fluorescent Reporter Assays

Strains were revived from glycerol stocks in 5 mL LB with overnight incubation at 30° C., 250 rpm. 5 mL starter cultures in M9*+20 mM glucose+10 mM $NH_4Cl$ were inoculated with 1% of the recovery culture and similarly incubated. Coupled growth and fluorescence assays were performed with a Neo2SM (Bio-Tek) plate reader using 200 µL/well of M9*+20 mM p-coumarate+2 (limiting) or 20 (replete) $NH_4Cl$ in black-walled, µClear® flat-bottom, 96-well plates (Greiner Bio-One) with an optically clear lid. Plate cultures were inoculated with 0.5% inoculum from starter cultures, and incubated overnight at 30° C., fast shaking with $OD_{600}$ and fluorescence ($F_{510,530}$ for mNeonGreen and $F_{588,633}$ for mKate2) measured every 10 minutes. Reporter expression per cell was estimated by dividing relative fluorescence units (RFU) by $OD_{600}$ (as a proxy for cell number) for each time point and averaging those values for time points occurring during either exponential growth or stationary phase. Background absorbance and fluorescence readings from wells containing media blanks were averaged and subtracted from sample readings prior to analysis. Exponential phase was defined as time points where $OD_{600}$ was between 0.039 and the $OD_{600}$ curve inflection point, typically $OD_{600}$~0.2 (nitrogen limited) or ~0.6 (nitrogen replete). Stationary phase was defined as time points starting 2 hours following end of exponential phase.

Shake Flask Experiments

Starter cultures were prepared as described for growth rate assays with the exception that 50 µg/mL kanamycin sulfate was added to the medium. Starter cultures were inoculated to a final $OD_{600}$ of 0.1 into 25 mL of M9* medium, supplemented with 20 mM p-coumarate and 2 mM $NH_4Cl$, in a 125 mL erlenmeyer flask and incubated at 30° C., 250 rpm. Cultures were sampled periodically to measure growth by $OD_{600}$, and analyte concentrations by high performance liquid chromatography (HPLC).

Analytical Techniques

For shake flask experiments, optical density at 600 nm ($OD_{600}$) was measured using a spectrophotometer (Amersham, UltroSpec10). HPLC analysis for p-coumarate and organic acid detection was performed by injecting 20 µL of 0.2 µm filtered culture supernatant onto a Waters 1515 series system equipped with a Rezex RFQ-Fast Acid H+ (8%) column (Phenomenex) and a Micro-Guard Cation $H^+$ cartridge (Bio-Rad). Samples were run with column at 60° C. using a mobile phase of 0.01 N sulfuric acid at a flow rate of 0.6 mL/min, with a refractive index detector and UV/Vis detector measuring A230 & A280 for analyte detection. Analytes were identified and quantified by comparing retention times and spectra with pure standards.

For shake flask experiments with M9*-BCDL, optical density at 600 nm ($OD_{600}$) was measured with a Nanodrop (ThermoFisher Scientific) after diluting samples 6-fold. Uninoculated M9*-BCDL medium was used as a blank to subtract signal coming from components in the medium.

Itaconic acid quantitation in M9*-BCDL. Prior the analysis, a 0.1 mL. aliquot was taken from each sample and 0.9 mL of water were added to make a 10× dilution. Then, 34 µL of 72% sulfuric acid were added to each diluted sample to decrease the pH below 2.0 and precipitate acid insoluble lignin. Samples were centrifuged, and the supernatant was filtered through a 0.2 µM filter pore size. Itaconic acid quantification was performed on an Agilent 1100 series HPLC system, with a diode array detector (DAD) at 210 nm (Agilent Technologies). Analysis was performed by injecting 6 µL of filtered culture supernatant onto a Phenomenex Rezex™ RFQ-Fast Acid H+ (8%) column with a cation H+guard cartridge (Bio-Rad Laboratories) at 85° C. using a mobile phase of 5 mM sulfuric acid at a flow rate of 1.0 mL/min.

Aromatic compounds quantitation in M9*-BCDL. Metabolite analysis in BCD was performed on an Agilent 1200 LC system (Agilent Technologies) equipped with a DAD. Each sample and standard was injected at a volume of 10 µL onto a Phenomenex Luna C18(2) column 5 µm, 4.6×150 mm column (Phenomenex). The column temperature was maintained at 30° C. and the buffers used to separate the analytes of interest were A) 0.05% acetic acid in water and B) 0.05% acetic acid in acetonitrile. The chromatographic separation was carried out using a gradient of: initially starting at 1% B going to 50% B at 35 min before immediately switching to 99% B at 35.1 min, before equilibrium for a total run time of 47 min. The flow rate of the mobile phases was held constant at 0.6 mL/min. The same standards used in the BCDL experiments were also used to construct calibration curves, but between the ranges of 5-200 µg/L. Three separate wavelengths from the DAD were used to identify and quantitate the analytes of interest. A wavelength of 210 nm and 225 nm was used for the analytes vanillic acid and 4-hydroxybenzoic acid. A wavelength of 325 nm was used for the analytes p-coumaric acid, and ferulic acid. A minimum of five calibration levels was used with an $r^2$ coefficient of 0.995 or better for each analyte.

Transcriptional Profiling of *P. putida*

For the determination of $NO_3$ induced promoters, strain JE1657, an engineered *P. putida* strain containing a Bxb1 phage integrases system for rapid genomic integration of DNA 3, and a PT7:mNeonGreen reporter cassette was used. JE1657 was cultured at 30 C in 50 mL MME mineral medium in a 250 mL erlenmeyer shake flask at 30° C., 250 rpm shaking and harvested mid-log (OD600=~0.2) by centrifugation (~16,000×g, 2 minutes, 4° C.). Supernatants were quickly decanted, and cell pellets were frozen rapidly in liquid nitrogen prior to storage at −80° C. for storage prior to RNA isolation. Four samples were prepared for each condition for characterization of biosensor performance strain JE2212 under identical conditions.

Cell pellets were resuspended in TRIzol (ThermoFisher-Invitrogen, Waltham, Mass. USA) and processed according to the manufactures protocol for TRIzol reagent. In general, TRIzol was added to cell pellets and mixed by vortex and pipetting. Chloroform was then added and mixed and samples were centrifuged. After centrifugation the aqueous layer was removed and mixed 1:1 with 80% ethanol. The samples were then purified on a RNeasy column (Qiagen Hilden, Germany) following the manufactures protocol and the on-column DNase digestion. RNA was eluted off the column in 35 μL RNAse free H20 (Qiagen, Hilden, Germany). RNA concentration was quantified using a Nanodrop 1000 instrument (ThermoScientific, Waltham, Mass.) and RNA quality was verified by obtaining RNA Integrity Numbers (RIN) using an RNA 6000 Nanochip on an Agilent 2100 Bioanalyzer (Agilent Technologies, Santa. Clara, Calif.).

Ribosomal RNA was depleted from total RNA samples using a RiboZero rRNA Removal Kit (Epicentre-Illumina Inc. San Diego, Calif.) according to manufacturer's instructions. The depleted sample was purified on a RNA Clean & Concentrator-5 (Zymo Research, Irvine, Calif., USA) following the manufacturer's protocol, and then the depleted material was quantified using a Nanodrop 1000 and visualized on an Agilent 2100 Bioanalyzer instrument with a RNA 6000 Nanochip (Agilent Technologies, Santa Clara, Calif.). RNA depleted of ribosomal RNA was used as input material to synthesize cDNA libraries using a ScriptSeq v2 RNA-Seq Library Preparation Kit (Illumina-Epicentre, San Diego, Calif., USA) according to manufacturer's instructions and TruSeq compatible barcodes. Pooled barcoded libraries were sequenced in one direction for 50 bases (SE50) on an Illumina Hi-Seq2500 using v4 chemistry (Illumina Inc. San Diego, Calif.) and de-multiplexed as a sequencing service provided by The Genomic Services Lab at Hudson Alpha Institute for Biotechnology (HudsonAlpha, Huntsville, Ala.).

Differential Gene Expression Analysis

After Illumina sequencing, RNA-seq reads were mapped to modified versions of the *P. putida* KT2440 reference genome (NC_002947) containing the mutations found in JE1657 and JE2212 using the Geneious for RNA-seq mapping workflow. Read count per annotated gene was calculated for each treatment and replicate, as well as fragment per kilobase million (FPKM), a common normalization technique. The inventors then exported gene locus tags and raw read counts into tab-delimited files, one for each replicate. To calculate differential gene expression, R package DESeq was used which calculates log-fold change in expression and allows comparison between treatments using several replicates. There were three (JE2212 assay) or four (JE1657 assay) replicates per treatment, for a total of six or eight inputs per experiment.

Gene and Protein Sequences

SEQ ID) NO: 105: cadA gene (Codon-optimized for *P. putida* KT2440).

SEQ ID NO: 106: tad1 gene (Codon-optimized for *P. putida* KT2440).

SEQ ID NO: 107: adi1 gene (Codon-optimized for *P. putida* KT2440).

SEQ ID NO: 108: cadA protein (Organism: *Aspergillus terreus*).

SEQ ID NO: 109: tad1 protein (Organism: *Ustilago maydis*).

SEQ ID NO: 110: adi1 protein (Organism: *Ustilago maydis*).

SEQ ID NO: 111: itp1 (itaconate transporter) protein (Organism: *Ustilago maydis*)

SEQ ID NO: 112: TbrB (trans-aconitate transporter) protein (Organism: *Bacillus thuringiensus* CT-43)

Example 2: Dynamic Regulation Enables Two-Stage Production of Itaconate Production from Lignin-Derive Aromatics The enzyme cis-aconitate decarboxylase produces itaconic acid (itaconate) by enzymatic decarboxylation of the TCA cycle intermediate cis-aconitate (FIG. 1B). In the fungus *Aspergillus terreus*, the cadA gene encodes cis-aconitate decarboxylase, and is the sole enzyme required for production of itaconate from the TCA cycle intermediate cis-aconitate. In *P. putida*, many aromatic compounds derived from lignin are funneled from numerous peripheral catabolic pathways into the intermediates catechol or protocatechuate, which are further metabolized by the β-ketoadipate pathway to produce an acetyl-CoA and succinate (FIG. 1A). The production of a single itaconate requires condensation of an acetyl-CoA and oxaloacetate, which is readily produced from succinate, into a citrate molecule, which can then be dehydrated to the immediate precursor cis-aconitate (FIG. 1B).

The inventors constructed an expression cassette containing codon optimized version of the cadA gene (SEQ ID NO: 105) under the control of the T7 promoter in a Bxb1 integrase target plasmid for rapid integration into the *P. putida* genome. This plasmid was integrated into the genome of *P. putida* JE2113 (Table 1), a host strain containing the $P_{urtA}$:T7 RNAP:lysY+ cassette, generating strain JE3128. Itaconic acid production by JE3128 was assayed by shake flask cultivation with M9* medium supplemented with 20 mM p-coumarate, a model lignin-derived aromatic compound, and limiting amounts of nitrogen (2 mM $N_4Cl$). With this strain and conditions, the inventors were able to detect production of itaconic acid, but the titer (23 mg/L) and molar yield (0.96% mol/mol) were low (Table 4).

TABLE 4

Production of itaconate from lignin-derived aromatics.

| Strain | Hosted Production Pathway | Relevant genotype | Overall Molar Yield (mol/mol) | Stationary Phase Molar Yield* (mol/mol) | Mass Yield (g/g) | Titer (g/L) |
|---|---|---|---|---|---|---|
| JE3128 | PT7:cad4 (cis) | JE90$P_{urtA}$:T7_RNAP:Pcat:lysY | 0.01 | n.d. | 0.01 | 0.02 |
| JE3221 | PT7:cadA (cis) | JE90$P_{urtA}$:T7_RNAP:Pcat:lysY ΔphaC1ZC2 | 0.09 | 0.18 | 0.07 | 0.22 |
| JE3659 | PT7:tad1:adi1 (trans) | JE90 $P_{urtA}$:T7_RNAP:Pcat:lysY ΔphaC1ZC2 | 0.23 | 0.39 | 0.19 | 0.57 |
| JE3713 | PT7:cadA (cis) | JE90 $P_{urtA}$:T7_RNAP:Pcat:lysY ΔphaC1ZC2 icdGTG:idhGTG | 0.29 | 0.79 | 0.23 | 0.72 |

TABLE 4-continued

Production of itaconate from lignin-derived aromatics.

| Strain | Hosted Production Pathway | Relevant genotype | Overall Molar Yield (mol/mol) | Stationary Phase Molar Yield* (mol/mol) | Mass Yield (g/g) | Titer (g/L) |
|---|---|---|---|---|---|---|
| JE3715 | PT7:tad1:adi1 (trans) | JE90 $P_{urtA}$:T7_RNAP:Pcat:lysY ΔphaC1ZC2 icdGTG:idhGTG | 0.43 | 1.02 | 0.34 | 1.09 |
| JE3717 | PT7:cadA (cis) | JE90 $P_{urtA}$:T7_RNAP:Pcat:lysY ΔphaC1ZC2 icdTTG:idhTTG | 0.50 | 0.97 | 0.40 | 1.27 |
| JE3719 | PT7:tad1:adi1 (trans) | JE90 $P_{urtA}$:T7_RNAP:Pcat:lysY ΔphaC1ZC2 icdTTG:idhTTG | 0.56 | 1.16 | 0.45 | 1.26 |

Figures 2A, 2B:
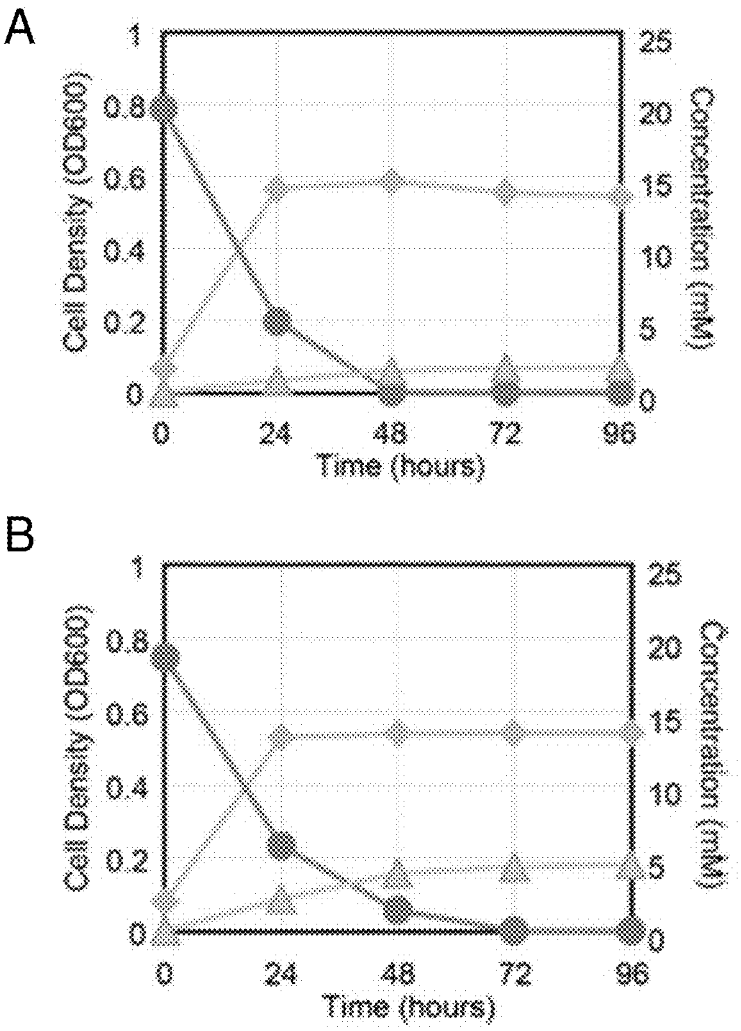
FIGS. 2A-2B. Production of itaconate by (A) strain JE3221 expressing the cis-pathway gene cadA, and (B) JE3659 expressing the trans-pathway genes tad1 & adi1, from the lignin-derived aromatic compound p-coumarate in shake flasks. Cell density as measured by $OD_{600}$ (gray diamonds), residual p-coumarate (blue circles), and produced itaconate (yellow triangles) are indicated. Values represent the average of three replicate shake flasks, with error bars indicated the standard deviation in among the three samples.

*P. putida* is well known to accumulate polyhydroxyalkanoates (PHA), a fatty acid-derived carbon storage polymer, from a variety of carbon sources, including lignin (Linger, J G., et al., *PNAS* 111.33 (2014): 12013-12018), in conditions where nitrogen is limited (Prieto, A. et al., *Environmental Microbiology,* 18.2 (2016): 341-357). Depending on the conditions, PHAs can accumulate to up to 8004 cell dry weight. As production of PHAs requires acetyl-CoA for production of fatty acid intermediates, it directly competes with itaconate production for acetyl-CoA (FIG. 1A). The inventors hypothesized that preventing the cell from producing PHAs, by deletion of the PHA synthetase genes, phaC1 and phaC2, would increase the flux of carbon during nitrogen-starvation towards the TCA cycle and itaconate production. The phaC1ZC2 operon was deleted from JE2113—generating strain JE3215, integrated the PT7:cadA cassette into JE3215 to generate strain JE3221, and tested this strain for production of itaconate from 20 mM p-coumarate under nitrogen-limited conditions. As predicted, removal of the competing pathway significantly increased titer (220 mg/L) and overall molar yield (8.56% mol/mol) (Table 4, FIG. 2A). In the first 24 hours, all of the growth occurs and some itaconate is formed—likely after the initial growth period—with a molar yield of 5.49%. However, the itaconate yield in the subsequent production/stationary phase was substantially higher (17.8% mol/mol) and accounted for over half of the total itaconate production.

Example 3: Metabolic Pathway Selection to Optimize Itaconate Production

To date, other than in organisms that natively produce itaconate, all attempts to engineer strains for itaconate production have focused on heterologous expression the cis-aconitate decarboxylase, or cis-pathway, from *A. terreus*. However, an alternate pathway for itaconate production was recently discovered in *Ustilago maydis* (Geiser et al., *Microbial Biotech.,* 9.1 (2016): 116-126). This pathway, referred to here as the trans-pathway, proceeds through two steps. First, cis-aconitate is isomerized to the thermodynamically favorable isomer, trans-aconitate, by aconitate isomerase (adi1, *P. putida* KT2440 protein sequence SEQ ID NO: 110), which is subsequently decarboxylated by trans-aconitate decarboxylase (tad1, *P. putida* KT2440 protein sequence SEQ ID NO: 109) generating itaconate (FIG. 1B). At equilibrium, the trans isomer comprises 88% of aconitate. Furthermore, trans-aconitate is not a substrate of aconitate hydratase, and also inhibits the aconitase enzyme. Taken together, the inventors hypothesized that the trans-pathway would improve itaconate production relative to the cis-pathway by providing a thermodynamically favorable route to divert carbon flux from the TCA cycle.

To test this hypothesis, the inventors constructed an expression cassette with the T7 promoter controlling expression of codon-optimized version of the tad1 & adi1 genes. The resulting plasmid was integrated into the genome of JE3215, generating strain JE3659. JE3659 was assayed for production of itaconate from p-coumarate under nitrogen-limited conditions. As hypothesized, utilization of the trans-pathway from *U. maydis* further increased both the titer (570 mg/L) and molar yield (23.39% mol/mol) (Table 4, FIG. 2B). Supporting the notion that diverting carbon out of the TCA cycle may improve yields, the inventors observed transient accumulation of up to 0.6 mM of the intermediate trans-aconitate. As observed with JE3221, itaconate yield in the stationary phase was substantially higher (38.79% mol/mol) than in the first 24 hours (16.84% mol/mol).

Example 4: Modulating TCA Cycle Flux Increases Itaconic Acid Yields and Titer One of the most reliable methods to increase product formation in a chemical reaction is to increase substrate concentration. As an obligate aerobe, *P. putida* maintains robust TCA cycle activity for energy production. The inventors hypothesized that the increased substrate accumulation with the trans pathway was the determining factor for the increase itaconate yields of JE3659 (trans) relative to JE3221 (cis). Accordingly, it was predicted that increasing accumulation of cis-aconitate would significantly increase yields. Reducing the flux through isocitrate dehydrogenase (FIG. 1B—icd idh), which decarboxylates isocitrate in a reaction that is essentially irreversible, should increase accumulation of the itaconate precursor cis-aconitate. Deletion of the two isocitrate dehydrogenase genes (icd & idh) in *P. putida* would likely produce a severely energy-starved, α-ketoglutarate auxotroph during growth on lignin-derived aromatics, so the inventors aimed to decrease expression of these enzymes instead. To reduce translational efficiency of the icd & idh genes, the start codons of each isocitrate dehydrogenase in JE3215 was altered from ATG to either GTG or TTG generating strains JE13674 and JE3681, respectively.

Figures 3A, 3B, 3C, 3D:
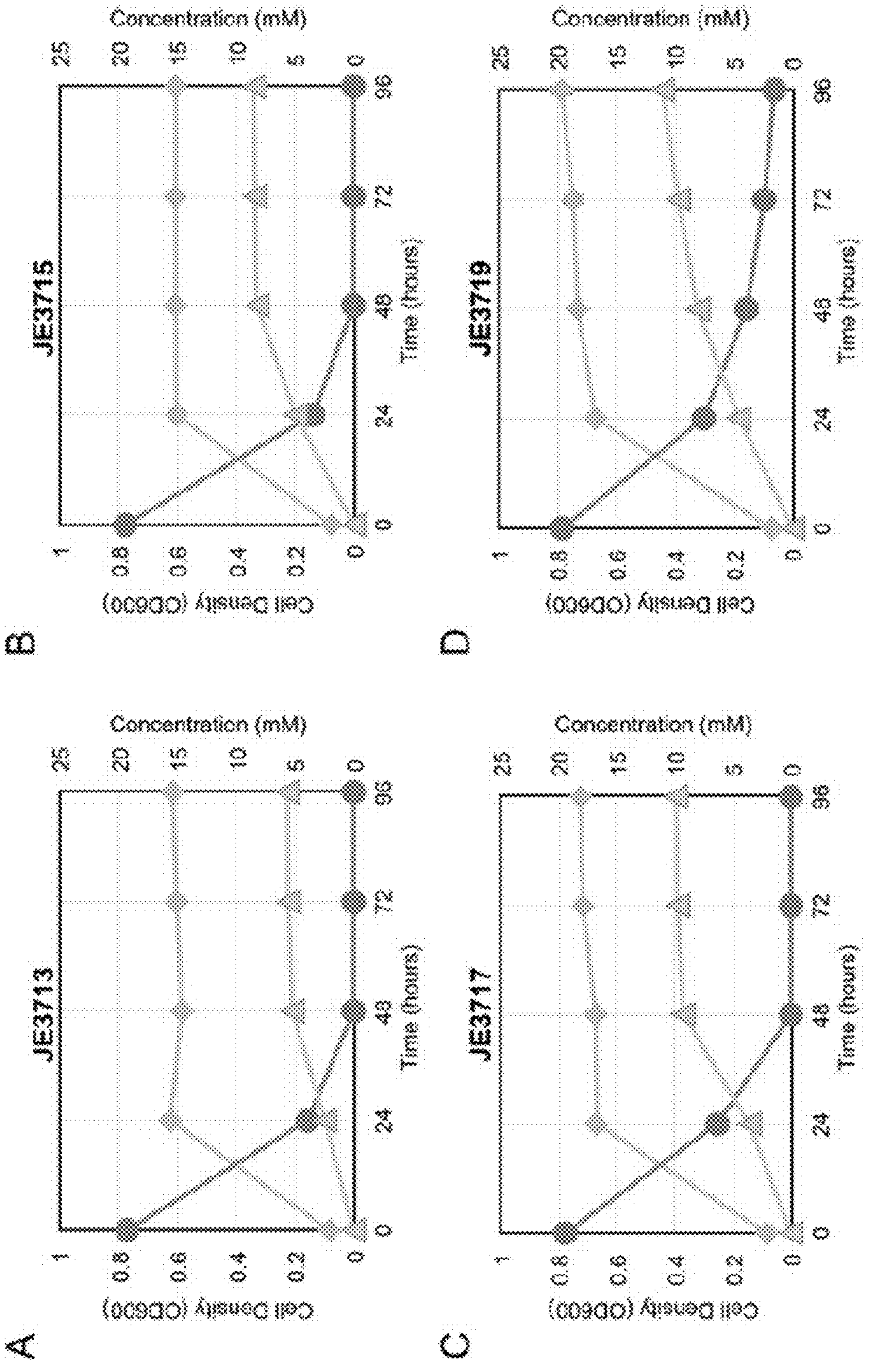
FIGS. 3A-3D. Reducing flux through the TCA cycle improves itaconate yield and titer. Production of itaconate from p-coumarate in shake flasks. Strains JE3713 (A) and JE3715 (B) have the GTG start codon replacements for icd and idh, and utilize the cis- and trans-pathways for itaconate production, respectively. Strains JE3717 (C) and JE3719 (D) have the TTG start codon replacements for icd and idh, and utilize the cis- and trans-pathways for itaconate production, respectively. Cell density as measured by $OD_{600}$ (gray diamonds), residual p-coumarate (blue circles), and produced itaconate (yellow triangles) concentrations are indicated. Values represent the average of three replicate shake flasks, with error bars indicated the standard deviation in among the three samples.

As these mutations are predicted to increase substrate accumulation for both the trans- and cis-pathways, itaconate production was tested with both pathways in JE3674 and JE3681 host strains. The cis- and trans-pathways were integrated into JE3674, generating strains JE3713 (cis) and JE3715 (trans), and JE3681, generating strains JE3717 (cis) and JE3719 (trans). All 4 strains were assayed for production of itaconate from p-coumarate under nitrogen-limited conditions. As hypothesized, the mild reduction of isocitrate dehydrogenase activity induced by the GIG start codons significantly increased itaconate titers and overall yields (FIGS. 3A-3B, Table 4) in both JE3713 (720 mg/L, 28.64% mol/mol) and JE3715 (1.09 g/L, 43.27% mol/mol). The additional reduction of isocitrate dehydrogenase activity with the TTG start codons even further increased overall itaconate production (FIGS. 3C-3D, Table 4). When compared to JE3717 (1.27 g/L, 50.37% mol/mol), containing the cis-pathway, the shift from GTG to TTG start codons in the trans-pathway strain JE3719 had less impact on itaconate yields (1.26 g/L, 56.52% mol/mol). As observed previously, the yield of itaconate from p-coumarate is substantially higher in stationary phase than the overall yields, and for all strains except JE3713 the molar yield is near or above 100% (Table 4).

Example 5: Production of Trans-Aconitate from Lignin-Derived Aromatics

Figure 4:
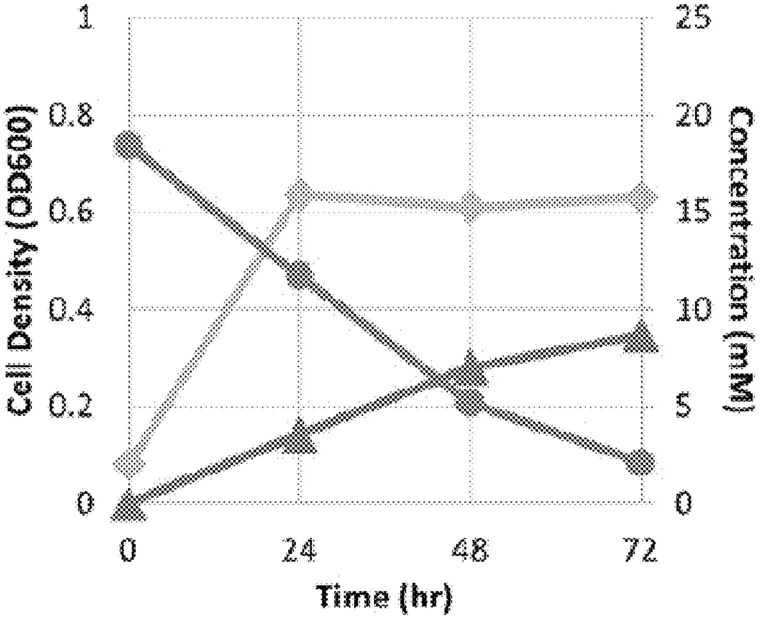
FIG. 4. Production of trans-aconitate from lignin-derived aromatics by strain JE3899 in shake flasks. Cell density as measured by $OD_{600}$ (gray diamonds), residual p-coumarate (blue circles), and produced trans-aconitate (purple triangles) are indicated. Values represent the average of three replicate shake flasks.
Figure 5A:
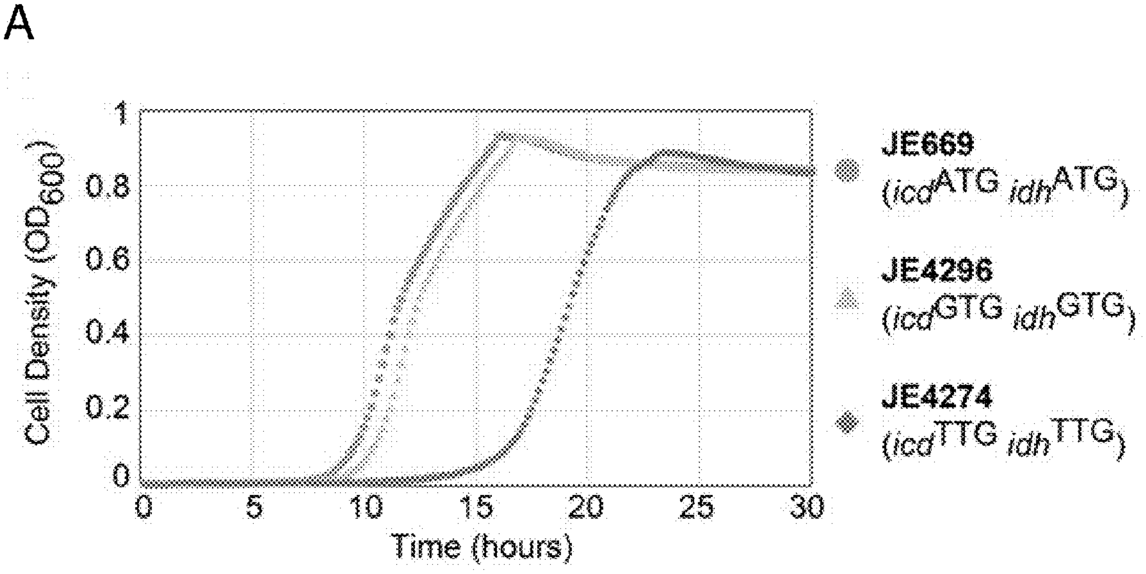
FIGS. 5A-5B. Effect of reduced isocitrate dehydrogenase production on growth and itaconate production by *Pseudomonas putida* KT2440. (A) Microtiter plate growth assay of *P. putida* strains harboring wild-type (gray circle), moderately reduced (yellow triangle), or strongly reduced (blue diamond) isocitrate dehydrogenase activity with p-coumarate as sole carbon source. Growth curves displayed are the average of three technical replicates. (B) Two-stage production of itaconic acid from p-coumaric acid in the presence of excess nitrogen (20 mM $NH_4$) by engineered *P. putida* strain JE4307 (constitutive cadA, $icd^{TTG}$ $idh^{TTG}$) in shake flasks. Cell density ($OD_{600}$, gray diamonds), residual p-coumaric acid (mM, blue circles), and produced itaconic acid (mM, yellow triangles) are indicated. Error bars indicate the standard deviation in three replicates.
Figure 5B:
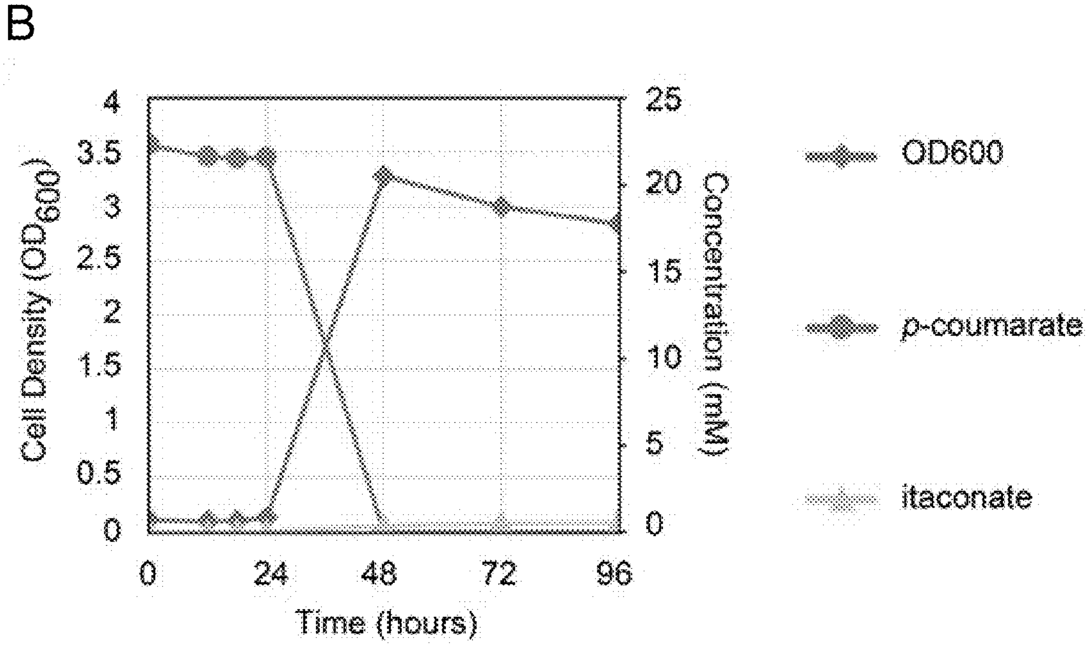

Trans-aconitate, an intermediate in the production of itaconate with the trans-pathway, is a compound with potential industrial value as well. If production of trans-aconitate becomes commercially viable, there are uses for trans-aconitate in the production of materials such as plasticizers and building blocks for hyperbranched polyesters, among others. Given the robust itaconate production by the instant engineered *P. putida* strains, the inventors hypothesized that they might also be able to produce high yields of trans-aconitate from lignin-derived aromatics using a truncated version of the trans-pathway. To test this hypothesis, the inventors constructed an expression cassette with a truncated version of the itaconic acid production trans-pathway that lack the trans-aconitate decarboxylase gene tad1, and contains just the aconitate isomerase, adi1, under the control of the T7 promoter. This cassette was incorporated into strain JE3681, generating strain JE3899. JE3899 was tested for production of trans-aconitate form p-coumarate under nitrogen-limited conditions. After 72 hours most of the p-coumarate was consumed and 1.51 g/L trans-aconitate was produced (FIG. 4). The yield was high with molar and mass yields of 53.17% mol/mol and 56.43% g/g, respectively.

Example 6: Modulating TCA Cycle Flux Increases Itaconic Acid Yields and Titer

Figures 1D, 1E:
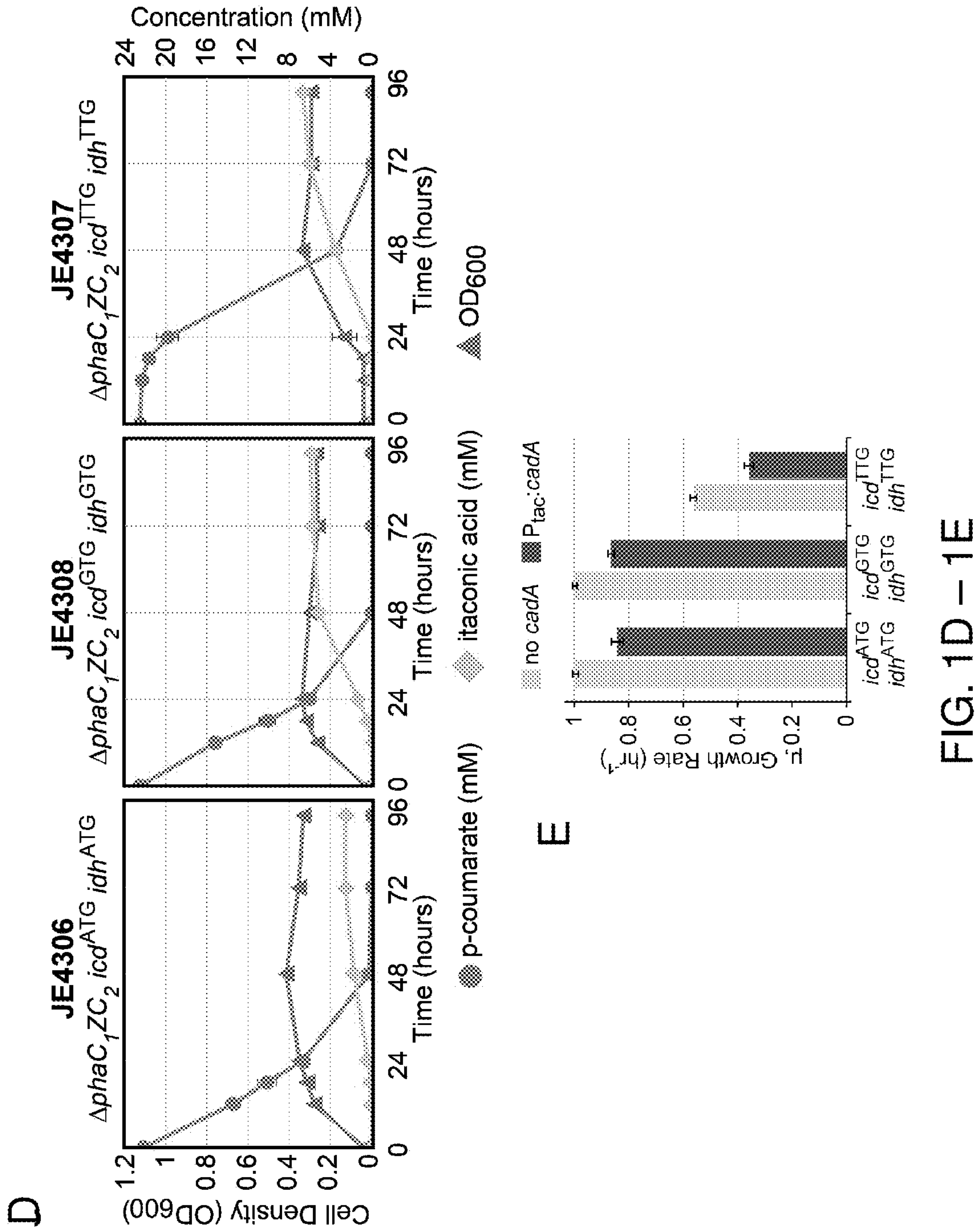

As an obligate aerobe, *P. putida* maintains robust TCA cycle activity for energy production. The inventors hypothesized that reducing flux through isocitrate dehydrogenase (FIG. 1B—icd, idh), should increase accumulation of cis-aconitate, and therefore increase yields. Deletion of icd and idh would make *P. putida* an energy-starved, α-ketoglutarate auxotroph, and likely be unable to grow on lignin-derived substrates. Instead, the inventors aimed to reduce translation efficiency of icd & idh by altering the start codons to GTG or TTG, generating strains JE4296 and JE4273, respectively. Cell yield (as measured by $OD_{600}$) was largely unaffected by the start codon alterations. The growth rate of JE4296 was also unaffected, while the growth rate of JE4273 on p-coumarate was decreased by 43.5% (FIG. 1E).

To determine the impact of these mutations on itaconate production, the inventors integrated the Ptac:cadA cassette into both strains, generating strains JE4308 (icdGTG:idhGTG) and JE4307 (icdTTG:idhTITG), and assayed itaconate production from p-coumarate under nitrogen-limited and nitrogen-replete conditions. Slowing the TCA cycle was sufficient to allow detectable itaconate production under nitrogen-replete conditions, and further increased yields under nitrogen-limited conditions to 26.5% and 30.47% mol/mol with JE3708 and JE3707, respectively (FIG. 1D). While yields improved, the detrimental effect of constitutive cadA expression was highlighted by decreased growth rates in strains expressing cadA (FIG. 1E). Growth rates in all three genetic backgrounds were negatively impacted by constitutive cadA expression, with impact being most pronounced in the JE4273 ($icd^{TG}$:$idh^{TTG}$) background where it caused a 36.5% reduction in growth rate.

Example 7: Development of a Signal-Amplified Nitrogen-Limitation Biosensor for Dynamic Metabolic Control in *Pseudomonas putida* KT2440

Figures 7A, 7B, 7C, 7D, 7E:
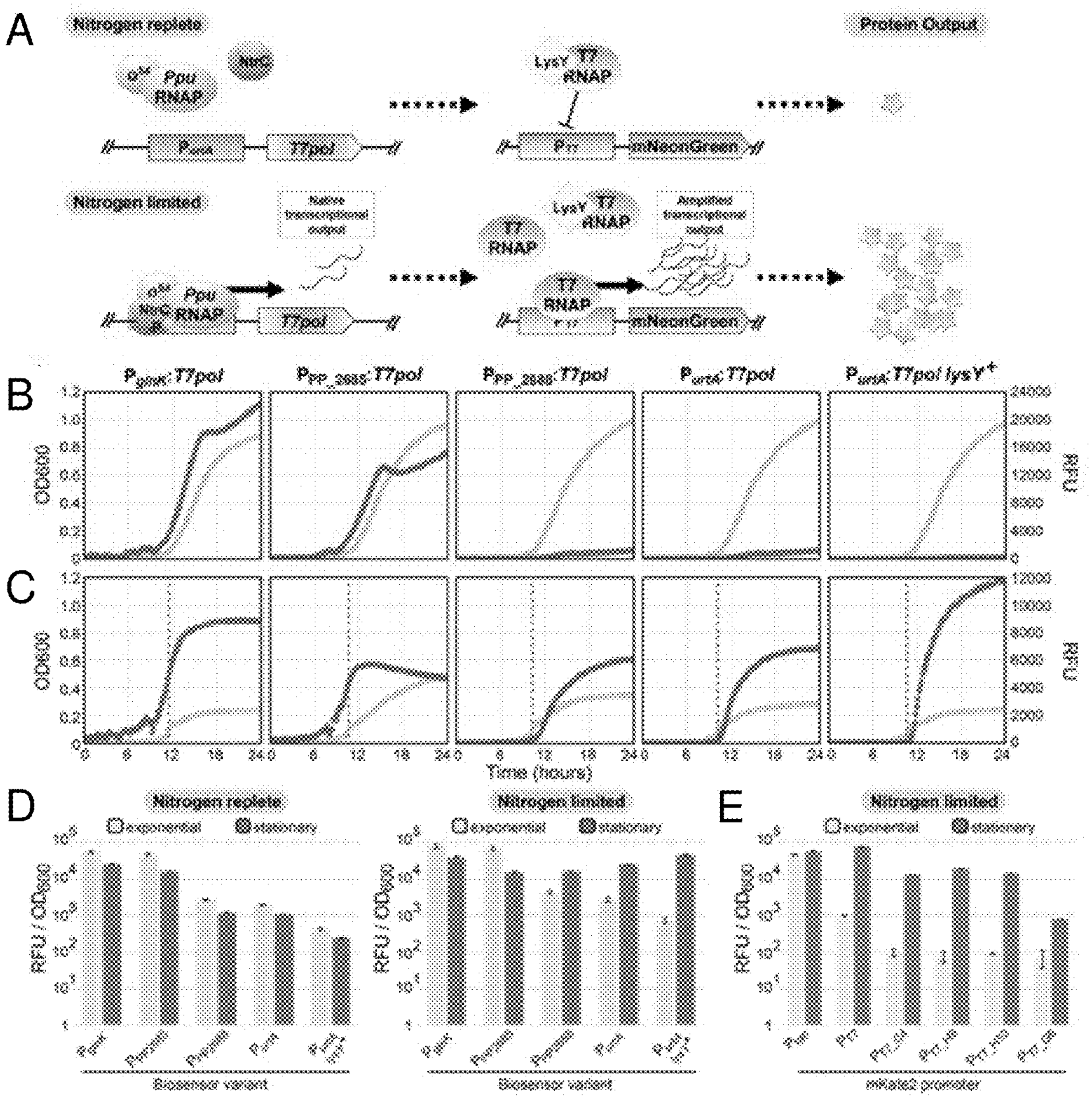
FIGS. 7A-7E. Development of a nitrogen-limitation biosensor to enable two-stage bioproductions. (A) Diagram of biosensor design and utilization as a regulated signal amplifier for pathway and tool expression. (B-C) Representative growth curves for 96-well microtiter plate cultivations of candidate biosensor strains, biosensor variant indicated, with integrated PT7:mNeonGreen cassette in either nitrogen-replete (B) or nitrogen-limited (C) medium. Cell density and mNeonGreen production, as measured by $OD_{600}$ (gray) and relative fluorescence units (RFU—green) respectively, were measured every 10 minutes. Entry to stationary phase is indicated (red dotted line) for nitrogen-limited cultures. (D) Graph of mNeonGreen production by candidate biosensor sensor strains during exponential growth (light green) or stationary phase (dark green) in microtiter plate cultivations. (E) Graph of mKate2 production by JE2113-derivatives with integrated PT7-variant:mKate2 cassettes during exponential growth (light pink) or stationary phase (dark pink) in plate reader cultivations. (d-e) Error bars indicate the standard deviation in at least 3 replicates.

By limiting its expression to production phase, dynamic regulation of the apparently toxic CadA protein could substantially improve itaconate production. Native regulatory systems are specifically tuned to provide expression sufficient for associated pathways which is often insufficient for heterologous pathways. Utilizing an orthogonal RNA polymerase intermediary, such as T7pol for dynamic regulation allows amplification of the original signal (FIG. 7A).

Here the inventors develop a biosensor that limits protein expression to production phase by controlling expression of T7pol with a nitrogen-sensitive promoter. Eleven candidate promoters were identified by comparing gene expression during growth on a good (NI-L) or poor ($NO_3$) nitrogen source (Table 5).

Table 5: Differential expression of genes downstream potential nitrogen-sensitive promoters.

| Locus Tag | Gene Name | $log_2$ fold change ($NaNO_3$/ $NH_4Cl$) | Base Mean | Predicted gene function |
|---|---|---|---|---|
| PP_1705 | nirB | 8.14 | 2029.14 | nitrite reductase large subunit |
| PP_2092 | nasA | 6.31 | 361.67 | nitrate transporter |
| PP_2094 | nasS | 2.79 | 51.23 | nitrate binding protein |
| PP_2685 | — | 4.44 | 320.51 | Bacterial proteasome, beta subunit |
| PP_2688 | — | 3.99 | 132.41 | Circularly permuted ATP-grasp type 2 |
| PP_2842 | ureD | 4.38 | 181.83 | urease accessory protein |
| PP_4053 | treY | 2.19 | 1151.28 | maltooligosyl trehalose synthase |
| PP_4841 | urtA | 4.37 | 455.68 | urea ABC transporter substrate-binding protein |
| PP_4842 | urtB | 4.56 | 72.42 | urea ABC transporter permease |
| PP_4845 | urtE | 3.77 | 67.21 | ABC transporter ATP-binding protein |
| PP_5234 | glnK | 1.45 | 8496.51 | NRII(GlnL/NtrB) phosphatase activator |

Figures 6A, 6B:
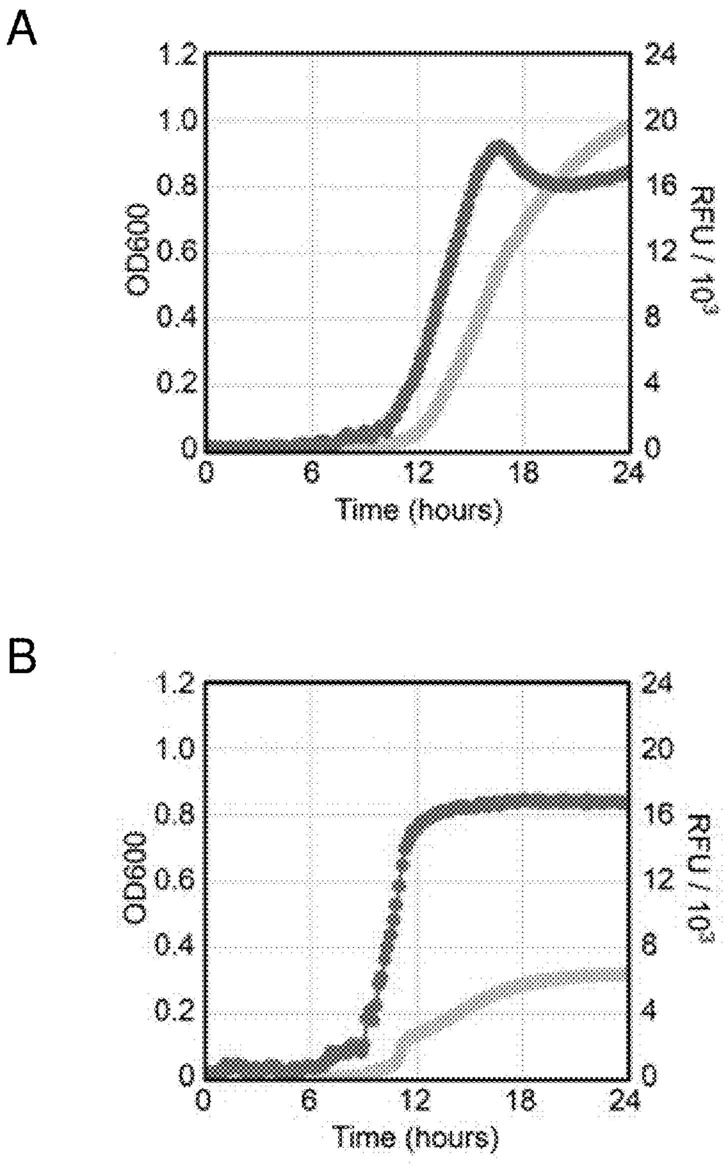
FIGS. 6A-6B. mNeonGreen production by constitutive promoter ($P_{tac}$) in a nitrogen-biosensor strain. Representative growth curves for 96-well microtiter plate cultivations of candidate biosensor strain JE2113 ($P_{urtA}$:T7 RNAP, lysY+) with integrated (constitutive) $P_{tac}$ controlled mNeonGreen cassette. Strain was grown in either nitrogen-replete (A) or nitrogen-limited conditions (B). Cell density and mNeonGreen production, as measured by $OD_{600}$ (gray) and relative fluorescence units (RFU—green) respectively, were measured every 10 minutes.

The inventors tested biosensors with four candidate promoters: $P_{PP\_2685}$, $P_{PP\_2688}$, $P_{urtA}$, and $P_{glnK}$. Candidate biosensors were integrated into the JE90 genome, replacing a β-lactam resistance gene, ampC, and assayed for production of the fluorescent protein mNeonGreen under either nitrogen-replete or nitrogen-limited conditions (FIGS. 7B-7D). While the $P_{glnK}$ and $P_{PP\_2685}$ candidate biosensors were surprisingly nitrogen-agnostic, displaying constitutive mNeonGreen expression similar to the $\sigma^{70}$ tac promoter (FIGS. 6A-6B), the other candidate $P_{PP\_2688}$- and $P_{urtA}$-based biosensors responded to nitrogen-limitation, demonstrating 3.7 and 8.8-fold mNeonGreen induction upon entry into nitrogen-depletion-induced stationary phase (FIG. 7D).

While the initial $P_{urtA}$ biosensor variant allowed strong induced expression, basal expression in the presence of nitrogen was relatively high. To reduce basal T7pol activity the inventors constitutively expressed a catalytically-deactivated variant of T7 lysozyme (LysY) (U.S. Pat. No. 8,138,324), which allosterically inhibits T7pol activity (FIG. 7A). The expression of LysY substantially improved biosensor performance: decreasing basal mNeonGreen expression by 78% in exponential phase, and increasing the maximal induced mNeonGreen expression level, resulting in 60-fold mNeonGreen induction, a 6.8-fold improvement (FIG. 7D). As an orthogonal measurement of biosensor performance, the inventors utilized RNAseq to compare gene expression with $NH_4$ and $NO_3$ as described previously. Highlighting the function of this biosensor as a signal amplifier, $NO_3$-induced mNeonGreen mRNA abundance was 302- and 54-fold higher than urtA and T7pol.

Optimal pathway performance often requires tuning expression of individual proteins. Tuning expression can be achieved with promoter (Elmore et al., *Metab Eng Commun* 5, 1-8 (2017)) and/or ribosome binding site (RBS) (Salis et al., *Nature Biotech.* 27.10 (2009): 946) modifications. The inventors utilized a small library of T7 promoter variants (see Table 6) with the red fluorescent protein mKate2 to demonstrate ability to tune the magnitude of biosensor outputs. Unlike the $\sigma^{70}$ tac promoter (FIG. 6A) which was constitutively expressed, nitrogen-limitation was required for induction of mKate2 production in all five T7 promoter variants (FIG. 7E, Table 6). With the promoter library we could tune maximal protein expression over an 89-fold range. Interestingly, the inventors observed a 2-3.5 fold dynamic range improvement over the T7 promoter with three of the variant promoters—largely driven by considerably lower basal expression—which approached the background autofluorescence.

TABLE 6

T7 Promoter variant testing.

| Promoter | T7 Promoter Variant Sequence | mKate2 production (RFU/OD600) Nitrogen-limited Exponential | Stationary | Fold-induction in N-limited stationary phase |
|---|---|---|---|---|
| Ptac (const.) | — | 43755 ± 1546 | 54287 ± 572 | 1.24 ± 0.03 |
| PT7 | taatacgactcactaTAGGGgaa (SEQ ID NO: 85) | 979 ± 30 | 73036 ± 2563 | 74.67 ± 4.76 |
| PT7_C4 | taatacgactcactaTTCAAGgaa (SEQ ID NO: 86) | 95 ± 24 | 12847 ± 416 | 142.61 ± 36.75 |
| PT7_H10 | taatacgactcactaCGGAAgaa (SEQ ID NO: 87) | 79 ± 28 | 17782 ± 301 | 262.27 ± 1977 |
| PT7_H9 | taatacgactcactaATACTgaa (SEQ ID NO: 88) | 91 ± 9 | 14110 ± 126 | 157.16 ± 17 |
| PT7_G6 | taatacgactcactaTTTCCTgaa (SEQ ID NO: 89) | 74 ± 38 | 817 ± 12 | 15.92 ± 12.22 |

Example 8: Dynamic Regulation Improves Two-Stage Production of Itaconate Production from Lignin-Derived Aromatics The inventors next sought to test whether dynamic regulation of cadA would improve itaconate production. For this, the inventors altered the isocitrate dehydrogenase start codons of JE2113, which contains $P_{urtA}$:T7pol:lysY$^{+}$ biosensor cassette, to generate strains JE3674 (icd$^{GTG}$:idh$^{GTG}$) and JE3681 (icd$^{TTG}$:idh$^{TTG}$). The inventors integrated a codon optimized copy of cadA (SEQ ID NO: 105) under the control of the T7 promoter into all three strains, and assayed production of itaconate from p-coumarate under nitrogen-limited conditions. Similar to previous shake flask experiments—with the exception of JE4307—growth is complete with the first 24 hours, with some itaconate production occurring, likely after growth is completed. Strain JE3717 ($P_{T7}$:cadA, icd$^{TTG}$:idh$^{TTG}$) achieved an itaconate yield of 510% mol/mol (FIG. 8A, Table 1), a 67% improvement over the best performing constitutive cadA expression strain, JE4307 ($P_{tac}$:cadA, $icd^{TTG}$:$idh^{TTG}$) (FIG. 1D). Itaconate yields with JE3221 ($icd^{ATG}$:$idh^{ATG}$) and JE3713 ($icd^{GTG}$:$idh^{GTG}$) were similar to those of their corresponding constitutive cadA strains (FIG. 1D, FIG. 8D), with slightly higher molar yield for JE3713 over JE4308 (29.1% vs. 26.5%). Furthermore, dynamic regulation of ca LA eliminated the growth defect induced by cadA expression (FIG. 8B), which has ramifications on itaconate productivity—at 48 hours JE3717 itaconate production is essentially complete (FIG. 8A), while production by JE4307 was not complete after 72 hours (FIG. 1D). Taken together, dynamic regulation of cadA has demonstrable improved performance, and will likely improve strain stability.

Example 9: Metabolic Pathway Selection to Optimize Itaconate Production

To date, other than in organisms that natively produce itaconate, attempts to engineer strains for itaconate production have focused on heterologous expression the cis-aconitate decarboxylase (termed here the cis-pathway) from *A. terreus*. However, an alternate pathway for itaconate production was recently discovered in *Ustilago maydis* (Geiser et al., *Microbial Biotech.,* 9.1 (2016): 116-126). This pathway, referred to here as the trans-pathway, proceeds through two steps. First, cis-aconitate is isomerized to the thermodynamically favorable isomer, trans-aconitate, by aconitate isomerase (adi1), which is subsequently decarboxylated by trans-aconitate decarboxylase (tad1) generating itaconate (FIG. 1B). The trains isomer comprises 88% of aconitate at equilibrium and is a competitive inhibitor of aconitase enzyme (Gawron et al., *Biochimnica et Biophysica Acta* (*BBA*)-*Enzymology,* 484.2 (1977): 453-464)—both features that could increase substrate accumulation.

Figures 8A, 8B, 8C:
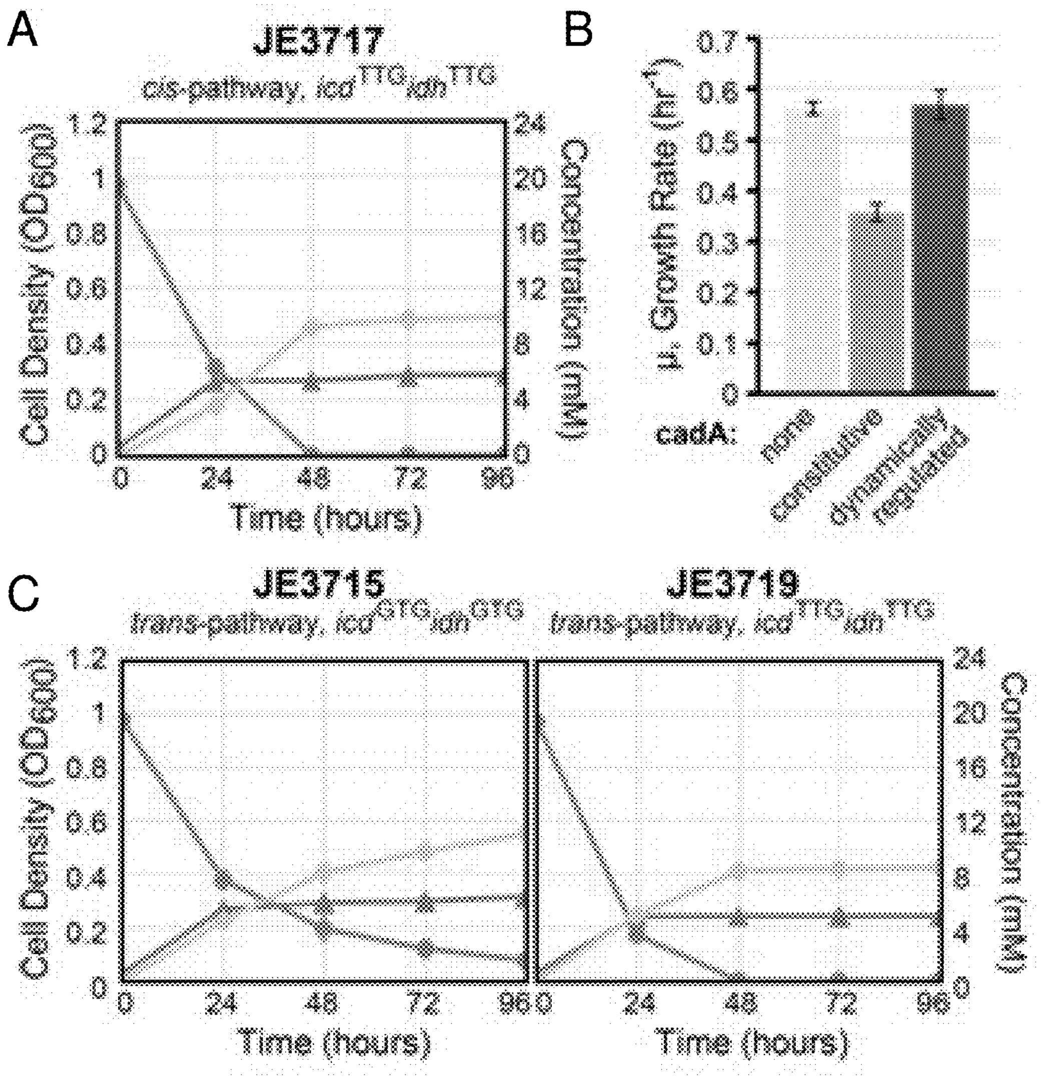
FIGS. 8A-8E. Biosensor-controlled expression of itaconate production pathways enables high yield production from lignin and model aromatic substrates. (A, C) Production of itaconic acid from p-coumarate in shake flasks by strains utilizing dynamically-regulated (A) cadA (cis-pathway) or (C) tad1/adi1 (trans-pathway) under nitrogen-limited conditions. Strain name and their unique modifications are indicated above the charts. Cell density (OD600, gray diamonds), p-coumaric acid (mM, blue circles), and itaconic acid (mM, yellow triangles) are indicated. (B) The effect of cadA expression on growth of *P. putida* icd$^{TTG}$ idh$^{TTG}$ strains in 48-well microtiter plate assays with p-coumarate as sole carbon source. (D) Molar yield of engineered strains from shake flask experiments with 20 mM p-coumarate as sole carbon source. Overall yield (yellow) and production phase yield (green) are indicated. Production phase was defined as 24 hr to 96 hr time points. (E) Consumption of detected aromatic monomers and production of itaconic acid from depolymerized lignin containing either 2 mM or 3 mM supplemented $NH_4Cl$ in shake flask cultivations with JE3715. (A-E) Error bars indicate the standard deviation in three replicates with the exception of the error bar for the 48 hr, 3 mM supplemented $NH_4Cl$ where the bar represents absolute error in two replicates.

Taken together, the inventors hypothesized that the trans-pathway would improve itaconate production relative to the cis-pathway by providing a thermodynamically favorable route to divert carbon flux from the TCA cycle. To test this hypothesis, the inventors integrated codon-optimized tad1 (SEQ) ID NO: 106) and adi1 (SEQ ID NO: 105) genes under the control of the T7 promoter into strains JE3674 and JE3681 and assayed the resulting strains JE3715 and JE3719, respectively, for itaconate production (FIG. 8C). As hypothesized, strains expressing the trans-pathway from *U. maydis* produced higher molar yields than equivalent strains expressing the cis-pathway (FIG. 8D, Table 7), and JE3719 produced the highest itaconate yield (56.4%) from p-coumarate in this study.

TABLE 7

Production of itaconic acid from p-coumaric acid

| Strain | Hosted Production Pathway | Relevant Parent Genotype | Overall Molar Yield (mol/mol) | Stationary Phase Molar Yield* (mol/mol) | Mass Yield (g/g) | Titer (g/L) |
|---|---|---|---|---|---|---|
| JE4305 | $P_{tac}$:cadA (cis) | JE90(*Pseudomonas putida* KT2440 ΔhsdR::Bxb1int-attB) | 0.04 | 0.1 | 0.03 | 0.02 |
| JE4306 | $P_{tac}$:cadA (cis) | JE90 $\Delta phaC_1ZC_2$ | 0.12 | 0.33 | 0.09 | 0.12 |
| JE4308 | $P_{tac}$:cadA (cis) | JE90 $\Delta phaC_1ZC_2$ $icd^{GTG}$:$idh^{GTG}$ | 0.27 | 0.72 | 0.21 | 0.34 |
| JE4307 | $P_{tac}$:cadA (cis) | JE90 $\Delta phaC_1ZC_2$ $icd^{TTG}$:$idh^{TTG}$ | 0.3 | n.d.** | 0.24 | 0.75 |
| JE3221 | $P_{T7}$:cadA (cis) | JE90 $P_{urtA}$:T7pol:$P_{cat}$:lysY $\Delta phaC_1ZC_2$ | 0.09 | 0.18 | 0.07 | 0.22 |
| JE3713 | $P_{T7}$:cadA (cis) | JE90 $P_{urtA}$:T7pol:$P_{cat}$:lysY $\Delta phaC_1ZC_2$ $icd^{GTG}$:$idh^{GTG}$ | 0.29 | 0.79 | 0.23 | 0.81 |
| JE3715 | $P_{T7}$:tad1:adi1 (trans) | JE90 $P_{urtA}$:T7pol:$P_{cat}$:lysY $\Delta phaC_1ZC_2$ $icd^{GTG}$:$idh^{GTG}$ | 0.43 | 1.02 | 0.34 | 1.09 |
| JE3717 | $P_{T7}$:cadA (cis) | JE90 $P_{urtA}$:T7pol:$P_{cat}$:lysY $\Delta phaC_1ZC_2$ $icd^{TTG}$:$idh^{TTG}$ | 0.5 | 0.97 | 0.4 | 1.27 |
| JE3719 | $P_{T7}$:tad1:adi1 (trans) | JE90 $P_{urtA}$:T7pol:$P_{cat}$:lysY $\Delta phaC_1ZC_2$ $icd^{TTG}$:$idh^{TTG}$ | 0.56 | 1.16 | 0.45 | 1.26 |

*Stationary phase molar yield was calculated using itaconate yield from 24 to 96 hour time points.
**Not Determined.

Example 10: Production of Itaconate from Depolymerized Lignin

To test the viability of itaconate production from lignin, we assayed the ability of strain JE3715 to upgrade a depolymerized lignin stream produced from an industrially-relevant lignocellulose deconstruction process (Rodriguez, *Acs Sustain Chem Eng* 5, 8171-8180 (2017)) to itaconate. Base-catalyzed depolymerization of washed lignin was performed as described previously (Rodriguez, *Acs Sustain*

Figures 8D, 8E:
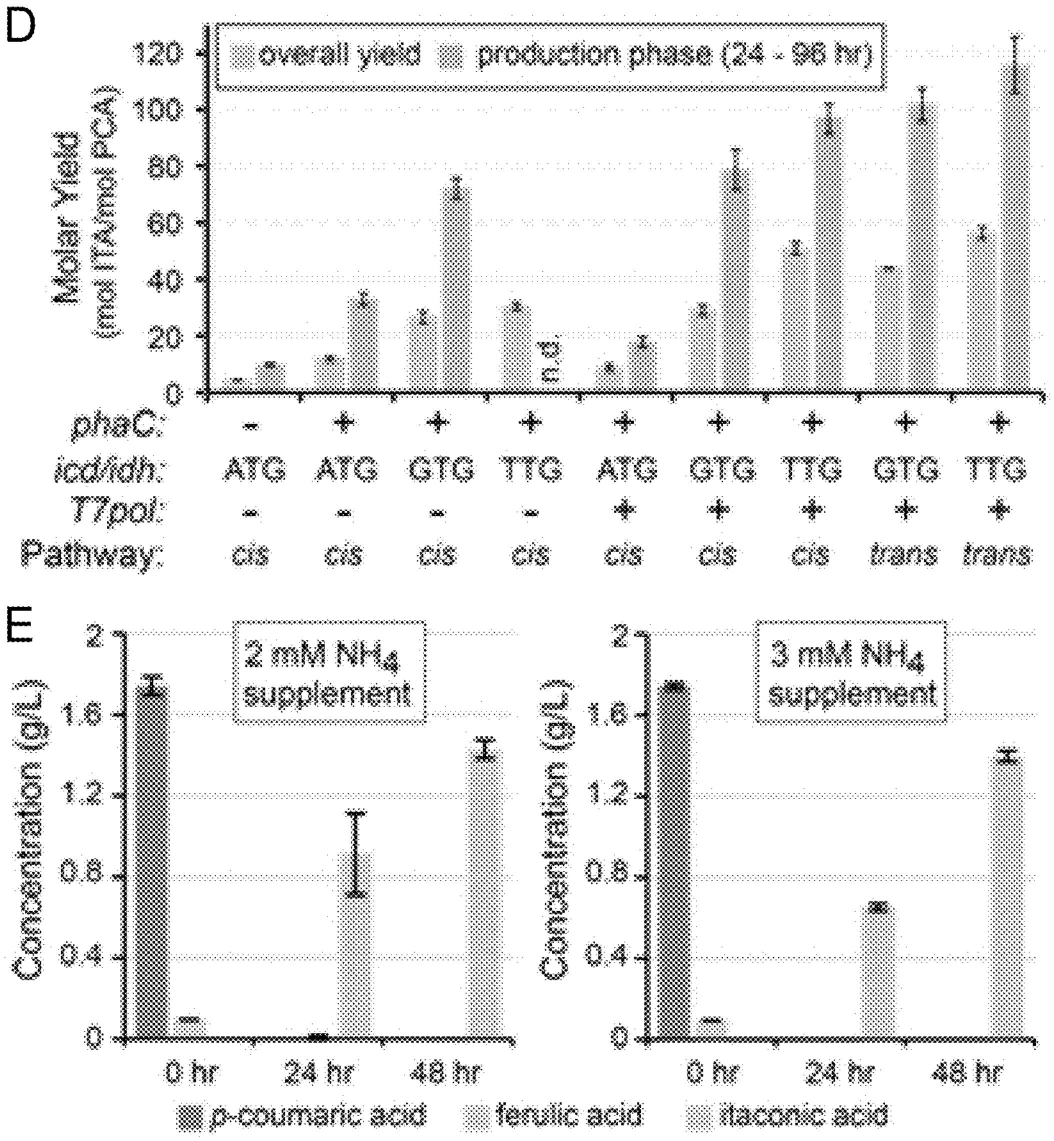

9*Chem Eng* 5, 8171-8180 (2017)), and the resulting liquor (BCDL) was diluted with concentrated modified M9 salts containing either 2 or 3 mM $NH_4Cl$. This medium was analyzed and found to contain ~1.74 g/L p-coumarate, 0.5 g/L ferulic acid (ferulate), trace amounts of other monomeric carbon sources, and residual higher molecular weight lignin. JE3715, chosen as a compromise between itaconate yield from coumarate and productivity, was inoculated into shake flasks containing the two media variants and assayed for itaconate production. Production of itaconic acid leveled off at 48 hours with titers between 1.4 and 1.43 g/L (FIG. 8E). The high apparent yields (98.8% molar yield and 0.79 g itaconate/g aromatic monomer) suggest that not only is depolymerized lignin a great substrate for itaconate production, but that the performance JE3715 is enhanced by components of the lignin and/or may also be consuming additional higher molecular weight lignin.

Example 11: Production of Itaconic Acid and Trans-Aconitate from Diverse Substrates Tables 8 and 9 summarize embodiments where itaconic acid (Table 8) and trans-aconitate (Table 9) was produced from diverse substrates using genetically engineered *Pseudomonas* strains. It is noted that the AG4074 strain has an exogenous nucleic acid comprising the itp1 gene (encoding an efflux pump for itaconic acid), and the AG4116 strain has an exogenous nucleic acid comprising the thrB gene (efflux pump for trans-aconitate).

TABLE 8

Production of Itaconic Acid from diverse substrates. Engineered strains were cultured on substrates encompassing a variety organic compound classes. Samples were collected following 72 hours growth and the final titer (g/L) of either itaconic acid or trans-aconitate was determined via HPLC. Genotypes of the engineered species are as follows:AG4001 AG4001:ΔPP_4740::Bxb1-attL:kanR:PT7:cadA:attR ΔampC::Pr_ 4841_T7_RNAP-lysY(+) ΔphaC1/Z/C2 icd(A1T):idh(A1T) Δged::araE-araCDABE fpvA:xylE-xylDXBC, AG4074:KT2440 ΔhsdR::Bxb1attL-KanR:Plac: itp1:Pt7:tad1:adi1-attR ΔampC::Pr_ 4841_T7_RNAP-lysY(+) ΔphaC1/Z/C2 icd(A1G):idh(A1G).

| | Substrate (Concentration) | | | | | | | | | |
|---|---|---|---|---|---|---|---|---|---|---|
| Strain | Glucose (20 mM) | Xylose (20 mM) | Arabinose (20 mM) | Coumarate (20 mM) | Ferulate (20 mM) | Benzoate (20 mM) | Acetate (30 mM) | Succinate (30 mM) | Octanoate (15 mM) | Glycerol (40 mM) |
| AG4001 | 0.970 | 0.359 | 0.475 | N/A | N/A | N/A | N/A | N/A | N/A | N/A |
| AG4074 | NA | N/A | N/A | 1.522 | 1.237 | 0.740 | 0.053 | 0.254 | 0.140 | 0.644 |
| | Sugar | Non-native sugar | Non-native sugar | Aromatic Monomer | Aromatic Monomer | Aromatic through alternate pathway | Organic Acid | Organic Acid | Fatty Acid | Biodiesel Waste |
| | Substrate Class | | | | | | | | | |

TABLE 9

Production of Trans-aconitate from diverse substrates. Engineered strains were cultured on substrates encompassing a variety organic compound classes. Samples were collected following 72 hours growth and the final titer (g/L) of either itaconic acid or trans-aconitate was determined via HPLC. Genotypes of the engineered species are as follows:AG4003:ΔPP_4740::Bxb1-attL:kanR:PT7:adi1:attR ΔampC::Pr_4841_T7_RNAP-lysY(+) ΔphaC1/Z/C2 icd(A1T):idh(A1T) Δgcd::araE-araCDABE fpvA:xylE-xylDXBC, AG4116:KT2440 ΔhsdR::Bxb1attL-KanR:Plac: tbrB:Pt7:adi1-attR ΔampC::Pr_4841_T7_RNAP-lysY(+) ΔphaC1/Z/C2 icd(A1G):idh(A1G).

| | Substrate (Concentration) | | | | | | | | | |
|---|---|---|---|---|---|---|---|---|---|---|
| Strain | Glucose (20 mM) | Xylose (20 mM) | Arabinose (20 mM) | Coumarate (20 mM) | Ferulate (20 mM) | Benzoate (20 mM) | Acetate (30 mM) | Succinate (30 mM) | Octanoate (15 mM) | Glycerol (40 mM) |
| AG4003 | 0.0117 | 0.0128 | 0.0003 | N/A | N/A | N/A | N/A | N/A | N/A | N/A |
| AG4116 | N/A | N/A | N/A | 1.106 | 0.796 | 0.680 | 0.086 | 0.470 | 0.604 | 0.670 |
| | Sugar | Non-native sugar | Non-native sugar | Aromatic Monomer | Aromatic Monomer | Aromatic through alternate pathway | Organic Acid | Organic Acid | Fatty Acid | Biodiesel Waste |
| | Substrate Class | | | | | | | | | |

What is claimed is:

1. A genetically-modified bacterium from the genus *Pseudomonas* comprising an exogenous nucleic acid encoding a cis-aconitate decarboxylase having a protein sequence with at least 95% identity to SEQ ID NO: 108, wherein the endogenous genes that encode polyhydroxyalkanoate (PHA) synthases are mutated to be inactivated in the bacterium.

2. A genetically-modified bacterium from the genus *Pseudomonas* comprising an exogenous nucleic acid encoding an aconitate isomerase having a protein sequence with at least 95% identity to SEQ ID NO: 110, wherein the endogenous genes that encode polyhydroxyalkanoate (PHA) synthases are mutated to be inactivated in the bacterium.

3. The genetically-modified bacterium of claim 2, wherein the bacterium further comprises an exogenous nucleic acid encoding a trans-aconitate decarboxylase having a protein sequence with at least 95% identity to SEQ ID NO: 109.

4. The genetically-modified bacterium of claim 2, wherein the bacterium does not have an exogenous nucleic acid encoding a trans-aconitate decarboxylase.

5. The genetically-modified bacterium of claim 1, wherein the bacterium comprises an exogenous nucleic acid encoding a cis-aconitate decarboxylase having a protein sequence with at least 95% identity to SEQ ID NO: 108, an exogenous nucleic acid encoding an aconitate isomerase having a protein sequence with at least 95% identity to SEQ ID NO: 110, and an exogenous nucleic acid encoding a trans-aconitate decarboxylase having a protein sequence with at least 95% identity to SEQ ID NO: 109.

6. The genetically-modified bacterium of claim 1, wherein the bacterium is grown on lignin or a breakdown product of lignin as a carbon source.

7. The genetically-modified bacterium of claim 6, wherein the breakdown product of lignin comprises p-coumaric acid, ferulic acid, or saccharides.

8. The genetically-modified bacterium of claim 1, wherein the bacterium is grown on an organic compound selected from the group consisting of an aromatic compound, a saccharide, an organic acid, and an alcohol.

9. The genetically-modified bacterium of claim 1, wherein the bacterium is grown on an organic compound selected from the group consisting glycerol, a diacid, a fatty acid, and benzoic acid.

10. The genetically-modified bacterium of claim 1, wherein the bacterium further comprises an exogenous nucleic acid encoding a citrate synthase.

11. The genetically-modified bacterium of claim 10, wherein the citrate synthase is a mutant enzyme that is immune to allosteric inhibition.

12. The genetically-modified bacterium of claim 1, wherein the level of isocitrate dehydrogenase in the bacterium is reduced compared to the corresponding wild-type bacterium.

13. The genetically-modified bacterium of claim 12, wherein (i) the start codon of the isocitrate dehydrogenase gene in the bacterium is either "GTG" or "TTG," (ii) the isocitrate dehydrogenase gene promoter in the bacterium comprises a mutation, (iii) the ribosome binding site of the isocitrate dehydrogenase gene transcript in the bacterium comprises a mutation, or (iv) the isocitrate dehydrogenase encoded by the isocitrate dehydrogenase gene in the bacterium comprises a protease recognition sequence.

14. The genetically-modified bacterium of claim 1, wherein the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

15. The genetically-modified bacterium of claim 1, wherein the bacterium further comprises an exogenous nucleic acid encoding an itaconic acid efflux pump having a protein sequence with at least 95% identity to SEQ ID NO: 111.

16. The genetically-modified bacterium of claim 4, wherein the bacterium further comprises an exogenous nucleic acid encoding a trans-aconitate efflux pump having a protein sequence with at least 95% identity to SEQ ID NO: 112.

17. A method for converting an organic compound to itaconic acid, the method comprising inoculating an aqueous solution containing said organic compound with the genetically-modified bacterium of claim 1.

18. The method of claim 17, wherein the organic compound is selected from aromatic compounds, saccharides, organic acids, and alcohols.

19. The method of claim 17, wherein the organic compound is a breakdown product of lignin produced during a lignin depolymerization process.

20. The method of claim 17, wherein the organic compound is selected from the group consisting of aromatic compounds, glycerol, diacids, fatty acids, and benzoic acid.

21. The method of claim 17, wherein the aqueous solution is a lignin depolymerization stream or derived from a lignin depolymerization stream.

22. The method of claim 21, wherein the lignin depolymerization stream contains p-coumaric acid, ferulic acid, and saccharides.

23. The method of claim 17, wherein the bacterium further comprises an exogenous nucleic acid encoding a citrate synthase.

24. The method of claim 23, wherein the citrate synthase is a mutant enzyme that is immune to allosteric inhibition.

25. The method of claim 17, wherein the level of isocitrate dehydrogenase in the bacterium is reduced compared to the corresponding wild-type bacterium.

26. The method of claim 25, wherein (i) the start codon of the isocitrate dehydrogenase gene in the bacterium is either "GTG" or "TTG," (ii) the isocitrate dehydrogenase gene promoter in the bacterium comprises a mutation, (iii) the ribosome binding site of the isocitrate dehydrogenase gene transcript in the bacterium comprises a mutation, or (iv) the isocitrate dehydrogenase encoded by the isocitrate dehydrogenase gene in the bacterium comprises a protease recognition sequence.

27. The method of claim 17, wherein the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina, P. taiwanensis.*

28. The method of claim 17, wherein the bacterium further comprises an exogenous nucleic acid encoding an itaconic acid efflux pump having a protein sequence with at least 95% identity to SEQ ID NO: 111.

29. A method for converting an organic compound to itaconic acid, the method comprising inoculating an aqueous solution containing said organic compound with the genetically-modified bacterium of claim 3.

30. The method of claim 29, wherein the organic compound is selected from aromatic compounds, saccharides, organic acids, and alcohols.

31. The method of claim 29, wherein the organic compound is a breakdown product of lignin produced during a lignin depolymerization process.

32. The method of claim 29, wherein the organic compound is selected from the group consisting of aromatic compounds, glycerol, diacids, fatty acids, and benzoic acid.

33. The method of claim 29, wherein the aqueous solution is a lignin depolymerization stream or derived from a lignin depolymerization stream.

34. The method of claim 33, wherein the lignin depolymerization stream contains p-coumaric acid, ferulic acid, and saccharides.

35. The method of claim 29, wherein the bacterium further comprises an exogenous nucleic acid encoding a citrate synthase.

36. The method of claim 35, wherein the citrate synthase is a mutant enzyme that is immune to allosteric inhibition.

37. The method of claim 29, wherein the level of isocitrate dehydrogenase in the bacterium is reduced compared to the corresponding wild-type bacterium.

38. The method of claim 37, wherein (i) the start codon of the isocitrate dehydrogenase gene in the bacterium is either "GTG" or "TTG," (ii) the isocitrate dehydrogenase gene promoter in the bacterium comprises a mutation, (iii) the ribosome binding site of the isocitrate dehydrogenase gene transcript in the bacterium comprises a mutation, or (iv) the isocitrate dehydrogenase encoded by the isocitrate dehydrogenase gene in the bacterium comprises a protease recognition sequence.

39. The method of claim 29, wherein the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegens, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis.*

40. The method of claim 29, wherein the bacterium further comprises an exogenous nucleic acid encoding an itaconic acid efflux pump having a protein sequence with at least 95% identity to SEQ ID NO: 111.

41. A method for converting an organic compound to trans-aconitate, the method comprising inoculating an aqueous solution containing said organic compound with the genetically-modified bacterium of claim 2.

42. The method of claim 41, wherein the organic compound is selected from aromatic compounds, saccharides, organic acids, and alcohols.

43. The method of claim 41, wherein the organic compound is a breakdown product of lignin produced during a lignin depolymerization process.

44. The method of claim 41, wherein the organic compound is selected from the group consisting of aromatic compounds, glycerol, diacids, fatty acids, and benzoic acid.

45. The method of claim 41, wherein the aqueous solution is a lignin depolymerization stream or derived from a lignin depolymerization stream.

46. The method of claim 45, wherein the lignin depolymerization stream contains p-coumaric acid, ferulic acid, and saccharides.

47. The method of claim 41, wherein the bacterium further comprises an exogenous nucleic acid encoding a citrate synthase.

48. The method of claim 47, wherein the citrate synthase is a mutant enzyme that is immune to allosteric inhibition.

49. The method of claim 41, wherein the level of isocitrate dehydrogenase in the bacterium is reduced compared to the corresponding wild-type bacterium.

50. The method of claim 49, wherein (i) the start codon of the isocitrate dehydrogenase gene in the bacterium is either "GTG" or "TTG," (ii) the isocitrate dehydrogenase gene promoter in the bacterium comprises a mutation, (iii) the ribosome binding site of the isocitrate dehydrogenase gene transcript in the bacterium comprises a mutation, or (iv) the isocitrate dehydrogenase encoded by the isocitrate dehydrogenase gene in the bacterium comprises a protease recognition sequence.

51. The method of claim 41, wherein the bacterium is selected from the group consisting of *P. aeruginosa, P. alcaligenes, P. anguilliseptica, P. argentinensis, P. borborid, P. citronellolis, P. flavescens, P. mendocina, P. nitroreducens, P. oleovorans, P. pseudoalcaligenes, P. resinovorans, P. straminea, P. asplenii, P. aurantiaca, P. aureofaciens, P. chlororaphis, P. corrugate, P. fragi, P. lundensis, P. taetrolens, P. antarctica, P. azotoformans, P. blatchfordae, P. brassicacearum, P. brenneri, P. cedrina, P. corrugate, P. fluorescens, P. gessardii, P. libanensis, P. mandelii, P. marginalis, P. mediterranea, P. meridiana, P. migulae, P. mucidolens, P. orientalis, P. panacis, P. protegees, P. proteolytica, P. rhodesiae, P. synxantha, P. thivervalensis, P. tolaasii, P. veronii, P. denitrificans, P. pertucinogena, P. putida* group, *P. cremoricolorata, P. entomophila, P. fulva, P. monteilii, P. mosselii, P. oryzihabitans, P. parafulva, P. plecoglossicida, P. putida, P. balearica, P. luteola, P. stutzeri, P. amygdali, P. avellanae, P. caricapapayae, P. cichorii, P. coronafaciens, P. ficuserectae, P. helianthin, P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. protegens, P. psychrophile, P. psychrotolerans, P. rathonis, P. reptilivora, P. resiniphila, P. rhizosphaerae, P. rubescens, P. salomonii, P. segitis, P. septica, P. simiae, P. suis, P. teessidea, P. thermotolerans, P. toyotomiensis, P. tremae, P. trivialis, P. turbinellae, P. tuticorinensis, P. umsongensis, P. vancouverensis, P. vranovensis, P. xanthomarina*, and *P. taiwanensis*.

52. The method of claim 41, wherein the bacterium further comprises an exogenous nucleic acid encoding a trans-aconitate efflux pump having a protein sequence with at least 95% identity to SEQ ID NO: 112.

* * * * *

SEQUENCE LISTING

```
<160> NUMBER OF SEQ ID NOS: 112

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide
```

-continued

<400> SEQUENCE: 1
attaatgcag ctggcacgac 20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
agctagctta tcgccattcg 20

<210> SEQ ID NO 3
<211> LENGTH: 58
<212> TYPE: DNA
<213> ORGANISM: Artificial Sequence
<220> FEATURE:
<223> OTHER INFORMATION: Oligonucleotide

<400> SEQUENCE: 3
tagctcactc aggaaacagc tatgacatga ttacgaattc gaccgaaaac atcggtgc 58

<210> SEQ ID NO 4
<211> LENGTH: 56
<212> TYPE: DNA
<213> ORGANISM: Artificial Sequence
<220> FEATURE:
<223> OTHER INFORMATION: Oligonucleotide

<400> SEQUENCE: 4
tcagcacgta ggtgccttct agagtctatt gtaggatcct ctacgacgct ccgttg 56

<210> SEQ ID NO 5
<211> LENGTH: 56
<212> TYPE: DNA
<213> ORGANISM: Artificial Sequence
<220> FEATURE:
<223> OTHER INFORMATION: Oligonucleotide

<400> SEQUENCE: 5
acaacggagc gtcgtagagg atcctacaat agactctaga aggcacctac gtgctg 56

<210> SEQ ID NO 6
<211> LENGTH: 56
<212> TYPE: DNA
<213> ORGANISM: Artificial Sequence
<220> FEATURE:
<223> OTHER INFORMATION: Oligonucleotide

<400> SEQUENCE: 6
ccagtcacga cgttgtaaaa cgacggccag tgccaagctt gcagccaaaa ccgcag 56

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
cagtaccagg cattgctgaa 20

<210> SEQ ID NO 8

-continued

<211> LENGTH: 18
<212> TYPE: DNA
<213> ORGANISM: Artificial Sequence
<220> FEATURE:
<223> OTHER INFORMATION: Oligonucleotide

<400> SEQUENCE: 8
gccaaggcag cagctaag 18

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
tggagctgaa gaacgtgttg 20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
ctcgtcgaca aacaaagcaa 20

<210> SEQ ID NO 11
<211> LENGTH: 60
<212> TYPE: DNA
<213> ORGANISM: Artificial Sequence
<220> FEATURE:
<223> OTHER INFORMATION: Oligonucleotide

<400> SEQUENCE: 11
ccagtcacga cgttgtaaaa cgacggccag tgccaagctt gtaaccacgg cctcactgaa 60

<210> SEQ ID NO 12
<211> LENGTH: 58
<212> TYPE: DNA
<213> ORGANISM: Artificial Sequence
<220> FEATURE:
<223> OTHER INFORMATION: Oligonucleotide

<400> SEQUENCE: 12
tagctcactc aggaaacagc tatgacatga ttacgaattc cttgcctctg ccggaaac 58

<210> SEQ ID NO 13
<211> LENGTH: 59
<212> TYPE: DNA
<213> ORGANISM: Artificial Sequence
<220> FEATURE:
<223> OTHER INFORMATION: Oligonucleotide

<400> SEQUENCE: 13
ctgtcgtttt gtccgacaat caacgcgagc gttaggatcc catcgccagt gacagactg 59

<210> SEQ ID NO 14
<211> LENGTH: 58
<212> TYPE: DNA
<213> ORGANISM: Artificial Sequence
<220> FEATURE:
<223> OTHER INFORMATION: Oligonucleotide

<400> SEQUENCE: 14
tgtcagagaa gtcgttctta gcgatgttaa tcgtgttcat gcggtttccc ttgtgttg 58

<210> SEQ ID NO 15
<211> LENGTH: 84
<212> TYPE: DNA
<213> ORGANISM: Artificial Sequence
<220> FEATURE:
<223> OTHER INFORMATION: Oligonucleotide

<400> SEQUENCE: 15
ctgtcgtttt gtccgacaat caacgcgagc gttaggatcc gcccgggtca aaagcgtgtc 60
agagaagtcg ttcttagcga tgtt 84

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide

<400> SEQUENCE: 16
aatcgtgttc atacccactc cttgccgccg tt 32

<210> SEQ ID NO 17
<211> LENGTH: 85
<212> TYPE: DNA
<213> ORGANISM: Artificial Sequence
<220> FEATURE:
<223> OTHER INFORMATION: Oligonucleotide

<400> SEQUENCE: 17
ctgtcgtttt gtccgacaat caacgcgagc gttaggatcc atggcctcgg gggctgttgt 60
cagagaagtc gttcttagcg atgtt 85

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide

<400> SEQUENCE: 18
aatcgtgttc atgtgctctc tccgctgagt 30

<210> SEQ ID NO 19
<211> LENGTH: 59
<212> TYPE: DNA
<213> ORGANISM: Artificial Sequence
<220> FEATURE:
<223> OTHER INFORMATION: Oligonucleotide

<400> SEQUENCE: 19
ctgtcgtttt gtccgacaat caacgcgagc gttaggatcc gctgcgcacc gaaattgtg 59

<210> SEQ ID NO 20
<211> LENGTH: 60
<212> TYPE: DNA
<213> ORGANISM: Artificial Sequence
<220> FEATURE:
<223> OTHER INFORMATION: Oligonucleotide

<400> SEQUENCE: 20
tgtcagagaa gtcgttctta gcgatgttaa tcgtgttcat gaaactctct cccgatttgg 60

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide

<400> SEQUENCE: 21
atgaacacga ttaacatcgc taag 24

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide

<400> SEQUENCE: 22
gtaaaaattg ccatcccaac agc 23

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide

<400> SEQUENCE: 23
gagcatcaat atgcaatgct gttg 24

<210> SEQ ID NO 24
<211> LENGTH: 17
<212> TYPE: DNA
<213> ORGANISM: Artificial Sequence
<220> FEATURE:
<223> OTHER INFORMATION: Oligonucleotide

<400> SEQUENCE: 24
cgctcaacgg acacgct 17

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
gaccattacg gtgagcgttt 20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
cgggttgaac attgacacag 20

<210> SEQ ID NO 27
<211> LENGTH: 17
<212> TYPE: DNA
<213> ORGANISM: Artificial Sequence
<220> FEATURE:
<223> OTHER INFORMATION: Oligonucleotide

<400> SEQUENCE: 27
ctcaacaagc gcgtagg 17

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide

<400> SEQUENCE: 28
gttcatgctt gagcaagcc 19

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
ggtgttactc gcagtgtgac 20

<210> SEQ ID NO 30
<211> LENGTH: 55
<212> TYPE: DNA
<213> ORGANISM: Artificial Sequence
<220> FEATURE:
<223> OTHER INFORMATION: Oligonucleotide

<400> SEQUENCE: 30
gtcttaatac gactcactat agggagagac ctggaattgt gagcggataa caatt 55

<210> SEQ ID NO 31
<211> LENGTH: 55
<212> TYPE: DNA
<213> ORGANISM: Artificial Sequence
<220> FEATURE:
<223> OTHER INFORMATION: Oligonucleotide

<400> SEQUENCE: 31
taagaattgt tatccgctca caattccagg tctctcccta tagtgagtcg tatta 55

<210> SEQ ID NO 32
<211> LENGTH: 22
<212> TYPE: DNA
<213> ORGANISM: Artificial Sequence
<220> FEATURE:
<223> OTHER INFORMATION: Oligonucleotide

<400> SEQUENCE: 32
gttgctagcg tcggggtttg ta 22

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide

<400> SEQUENCE: 33
aaaaccgccc agtctagcta tcg 23

<210> SEQ ID NO 34

<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
ggcgttgctg gaagagtatt 20

<210> SEQ ID NO 35
<211> LENGTH: 19
<212> TYPE: DNA
<213> ORGANISM: Artificial Sequence
<220> FEATURE:
<223> OTHER INFORMATION: Oligonucleotide

<400> SEQUENCE: 35
accactgcca gcagaattg 19

<210> SEQ ID NO 36
<211> LENGTH: 19
<212> TYPE: DNA
<213> ORGANISM: Artificial Sequence
<220> FEATURE:
<223> OTHER INFORMATION: Oligonucleotide

<400> SEQUENCE: 36
gctgttgcca tcgatcagt 19

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
acgaccagtt acaggccaag 20

<210> SEQ ID NO 38
<211> LENGTH: 19
<212> TYPE: DNA
<213> ORGANISM: Artificial Sequence
<220> FEATURE:
<223> OTHER INFORMATION: Oligonucleotide

<400> SEQUENCE: 38
gggagacggc ttcatcatg 19

<210> SEQ ID NO 39
<211> LENGTH: 23
<212> TYPE: DNA
<213> ORGANISM: Artificial Sequence
<220> FEATURE:
<223> OTHER INFORMATION: Oligonucleotide

<400> SEQUENCE: 39
atcactgtat ccatcttgtc atg 23

<210> SEQ ID NO 40
<211> LENGTH: 55
<212> TYPE: DNA
<213> ORGANISM: Artificial Sequence
<220> FEATURE:
<223> OTHER INFORMATION: Oligonucleotide

<400> SEQUENCE: 40
gtcttaatac gactcactat caaggaagac ctggaattgt gagcggataa caatt 55

<210> SEQ ID NO 41
<211> LENGTH: 55
<212> TYPE: DNA
<213> ORGANISM: Artificial Sequence
<220> FEATURE:
<223> OTHER INFORMATION: Oligonucleotide

<400> SEQUENCE: 41
taagaattgt tatccgctca caattccagg tcttccttga tagtgagtcg tatta 55

<210> SEQ ID NO 42
<211> LENGTH: 55
<212> TYPE: DNA
<213> ORGANISM: Artificial Sequence
<220> FEATURE:
<223> OTHER INFORMATION: Oligonucleotide

<400> SEQUENCE: 42
gtcttaatac gactcactac ggaagaagac ctggaattgt gagcggataa caatt 55

<210> SEQ ID NO 43
<211> LENGTH: 55
<212> TYPE: DNA
<213> ORGANISM: Artificial Sequence
<220> FEATURE:
<223> OTHER INFORMATION: Oligonucleotide

<400> SEQUENCE: 43
taagaattgt tatccgctca caattccagg tcttcttccg tagtgagtcg tatta 55

<210> SEQ ID NO 44
<211> LENGTH: 55
<212> TYPE: DNA
<213> ORGANISM: Artificial Sequence
<220> FEATURE:
<223> OTHER INFORMATION: Oligonucleotide

<400> SEQUENCE: 44
gtcttaatac gactcactaa tactgaagac ctggaattgt gagcggataa caatt 55

<210> SEQ ID NO 45
<211> LENGTH: 55
<212> TYPE: DNA
<213> ORGANISM: Artificial Sequence
<220> FEATURE:
<223> OTHER INFORMATION: Oligonucleotide

<400> SEQUENCE: 45
taagaattgt tatccgctca caattccagg tcttcagtat tagtgagtcg tatta 55

<210> SEQ ID NO 46
<211> LENGTH: 55
<212> TYPE: DNA
<213> ORGANISM: Artificial Sequence
<220> FEATURE:
<223> OTHER INFORMATION: Oligonucleotide

<400> SEQUENCE: 46
gtcttaatac gactcactat ttcggaagac ctggaattgt gagcggataa caatt 55

<210> SEQ ID NO 47
<211> LENGTH: 55
<212> TYPE: DNA

<213> ORGANISM: Artificial Sequence
<220> FEATURE:
<223> OTHER INFORMATION: Oligonucleotide

<400> SEQUENCE: 47
taagaattgt tatccgctca caattccagg tcttccgaaa tagtgagtcg tatta 55

<210> SEQ ID NO 48
<211> LENGTH: 60
<212> TYPE: DNA
<213> ORGANISM: Artificial Sequence
<220> FEATURE:
<223> OTHER INFORMATION: Oligonucleotide

<400> SEQUENCE: 48
cccgaaaggg gggccttttt tcgttttggt ccactagtca ctatcgacta cgcgatcatg 60

<210> SEQ ID NO 49
<211> LENGTH: 60
<212> TYPE: DNA
<213> ORGANISM: Artificial Sequence
<220> FEATURE:
<223> OTHER INFORMATION: Oligonucleotide

<400> SEQUENCE: 49
gaaggcgctg gtcttcgcgc ccatcatgag gtggcgccgt acgcttgccc ttcgttcgac 60

<210> SEQ ID NO 50
<211> LENGTH: 57
<212> TYPE: DNA
<213> ORGANISM: Artificial Sequence
<220> FEATURE:
<223> OTHER INFORMATION: Oligonucleotide

<400> SEQUENCE: 50
tctcccacca acgcttaagg tcgaacgaag ggcaagcgta cggcgccacc tcatgat 57

<210> SEQ ID NO 51
<211> LENGTH: 59
<212> TYPE: DNA
<213> ORGANISM: Artificial Sequence
<220> FEATURE:
<223> OTHER INFORMATION: Oligonucleotide

<400> SEQUENCE: 51
caggtctctc cctatagtga gtcgtattaa gactactagt cctgttgata ccgggaagc 59

<210> SEQ ID NO 52
<211> LENGTH: 22
<212> TYPE: DNA
<213> ORGANISM: Artificial Sequence
<220> FEATURE:
<223> OTHER INFORMATION: Oligonucleotide

<400> SEQUENCE: 52
tcacggacac caacattctg ac 22

<210> SEQ ID NO 53
<211> LENGTH: 40
<212> TYPE: DNA
<213> ORGANISM: Artificial Sequence
<220> FEATURE:
<223> OTHER INFORMATION: Oligonucleotide

<400> SEQUENCE: 53
gataacaatt cttaagatta actcacacag gagatatcat 40

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide

<400> SEQUENCE: 54
ccttggtaaa cattttcaga aaacc 25

<210> SEQ ID NO 55
<211> LENGTH: 24
<212> TYPE: DNA
<213> ORGANISM: Artificial Sequence
<220> FEATURE:
<223> OTHER INFORMATION: Oligonucleotide

<400> SEQUENCE: 55
gaacgcagct atgggggttt tctg 24

<210> SEQ ID NO 56
<211> LENGTH: 51
<212> TYPE: DNA
<213> ORGANISM: Artificial Sequence
<220> FEATURE:
<223> OTHER INFORMATION: Oligonucleotide

<400> SEQUENCE: 56
aaggcccccc gttagggagg ccttattgtt cgtctctaga ttagaccaag g 51

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide

<400> SEQUENCE: 57
tgcatagcgc aagcattgtg 20

<210> SEQ ID NO 58
<211> LENGTH: 47
<212> TYPE: DNA
<213> ORGANISM: Artificial Sequence
<220> FEATURE:
<223> OTHER INFORMATION: Oligonucleotide

<400> SEQUENCE: 58
attctaggca ctgctgtact gatagggtat tcacgccgac gatggac 47

<210> SEQ ID NO 59
<211> LENGTH: 52
<212> TYPE: DNA
<213> ORGANISM: Artificial Sequence
<220> FEATURE:
<223> OTHER INFORMATION: Oligonucleotide

<400> SEQUENCE: 59
cgtgtgttga gccgtccatc gtcggcgtga ataccctatc agtacagcag tg 52

<210> SEQ ID NO 60
<211> LENGTH: 51
<212> TYPE: DNA
<213> ORGANISM: Artificial Sequence
<220> FEATURE:

<223> OTHER INFORMATION: Oligonucleotide

<400> SEQUENCE: 60
tggaattgtg agcggataac aattcttaag gtagataaga gcgggtcatc g 51

<210> SEQ ID NO 61
<211> LENGTH: 48
<212> TYPE: DNA
<213> ORGANISM: Artificial Sequence
<220> FEATURE:
<223> OTHER INFORMATION: Oligonucleotide

<400> SEQUENCE: 61
gttagggagg ccttattgtt cgtctctaga tcaggacaag ctccggtc 48

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide

<400> SEQUENCE: 62
agcaacggtt ggatagcatc 20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
caggtctttc ccgatgcaat 20

<210> SEQ ID NO 64
<211> LENGTH: 19
<212> TYPE: DNA
<213> ORGANISM: Artificial Sequence
<220> FEATURE:
<223> OTHER INFORMATION: Oligonucleotide

<400> SEQUENCE: 64
aaccgcatcc gtccgatac 19

<210> SEQ ID NO 65
<211> LENGTH: 52
<212> TYPE: DNA
<213> ORGANISM: Artificial Sequence
<220> FEATURE:
<223> OTHER INFORMATION: Oligonucleotide

<400> SEQUENCE: 65
cactcaggaa acagctatga catgattacg aattcgccgc catcaagcag tt 52

<210> SEQ ID NO 66
<211> LENGTH: 25
<212> TYPE: DNA
<213> ORGANISM: Artificial Sequence
<220> FEATURE:
<223> OTHER INFORMATION: Oligonucleotide

<400> SEQUENCE: 66
ggataccaga aaatcaaggt tccga 25

<210> SEQ ID NO 67
<211> LENGTH: 49
<212> TYPE: DNA
<213> ORGANISM: Artificial Sequence
<220> FEATURE:
<223> OTHER INFORMATION: Oligonucleotide

<400> SEQUENCE: 67
tcggaacctt gattttctgg tatcccaccg aagcactact ccgctgtcg 49

<210> SEQ ID NO 68
<211> LENGTH: 54
<212> TYPE: DNA
<213> ORGANISM: Artificial Sequence
<220> FEATURE:
<223> OTHER INFORMATION: Oligonucleotide

<400> SEQUENCE: 68
tatagatgat cttggaacgg gtgggcacgt ttgttaactc tctgtgtgct gagc 54

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide

<400> SEQUENCE: 69
cccacccgtt ccaagatcat 20

<210> SEQ ID NO 70
<211> LENGTH: 52
<212> TYPE: DNA
<213> ORGANISM: Artificial Sequence
<220> FEATURE:
<223> OTHER INFORMATION: Oligonucleotide

<400> SEQUENCE: 70
cacgacgttg taaaacgacg gccagtgcca agcttaacat gatcgggtcg ga 52

<210> SEQ ID NO 71
<211> LENGTH: 49
<212> TYPE: DNA
<213> ORGANISM: Artificial Sequence
<220> FEATURE:
<223> OTHER INFORMATION: Oligonucleotide

<400> SEQUENCE: 71
tcggaacctt gattttctgg tatcccaacg aagcactact ccgctgtcg 49

<210> SEQ ID NO 72
<211> LENGTH: 54
<212> TYPE: DNA
<213> ORGANISM: Artificial Sequence
<220> FEATURE:
<223> OTHER INFORMATION: Oligonucleotide

<400> SEQUENCE: 72
tatagatgat cttggaacgg gtgggcaagt ttgttaactc tctgtgtgct gagc 54

<210> SEQ ID NO 73
<211> LENGTH: 21
<212> TYPE: DNA
<213> ORGANISM: Artificial Sequence
<220> FEATURE:
<223> OTHER INFORMATION: Oligonucleotide

<400> SEQUENCE: 73
cgataccaca taatcacgca c 21

<210> SEQ ID NO 74
<211> LENGTH: 19
<212> TYPE: DNA
<213> ORGANISM: Artificial Sequence
<220> FEATURE:
<223> OTHER INFORMATION: Oligonucleotide

<400> SEQUENCE: 74
ctctcgactt tccgctcat 19

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide

<400> SEQUENCE: 75
ttttctggta tcccaccgaa 20

<210> SEQ ID NO 76
<211> LENGTH: 14
<212> TYPE: DNA
<213> ORGANISM: Artificial Sequence
<220> FEATURE:
<223> OTHER INFORMATION: Oligonucleotide

<400> SEQUENCE: 76
gggtgggcac gttt 14

<210> SEQ ID NO 77
<211> LENGTH: 22
<212> TYPE: DNA
<213> ORGANISM: Artificial Sequence
<220> FEATURE:
<223> OTHER INFORMATION: Oligonucleotide

<400> SEQUENCE: 77
gattttctgg tatcccaacg aa 22

<210> SEQ ID NO 78
<211> LENGTH: 15
<212> TYPE: DNA
<213> ORGANISM: Artificial Sequence
<220> FEATURE:
<223> OTHER INFORMATION: Oligonucleotide

<400> SEQUENCE: 78
cgggtgggca agttt 15

<210> SEQ ID NO 79
<211> LENGTH: 22
<212> TYPE: DNA
<213> ORGANISM: Artificial Sequence
<220> FEATURE:
<223> OTHER INFORMATION: Oligonucleotide

<400> SEQUENCE: 79
gattttctgg tatcccatgc tt 22

<210> SEQ ID NO 80
<211> LENGTH: 12

<212> TYPE: DNA
<213> ORGANISM: Artificial Sequence
<220> FEATURE:
<223> OTHER INFORMATION: Oligonucleotide

<400> SEQUENCE: 80
gtgggcatgc gg 12

<210> SEQ ID NO 81
<211> LENGTH: 19
<212> TYPE: DNA
<213> ORGANISM: Artificial Sequence
<220> FEATURE:
<223> OTHER INFORMATION: Oligonucleotide

<400> SEQUENCE: 81
gtggcgatca cgtcgtact 19

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide

<400> SEQUENCE: 82
aggttggtga tgcctttgtc 20

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide

<400> SEQUENCE: 83
aggaatgatc ggatggtcag 20

<210> SEQ ID NO 84
<211> LENGTH: 21
<212> TYPE: DNA
<213> ORGANISM: Artificial Sequence
<220> FEATURE:
<223> OTHER INFORMATION: Oligonucleotide

<400> SEQUENCE: 84
catgtagttg taggcgtctt c 21

<210> SEQ ID NO 85
<211> LENGTH: 23
<212> TYPE: DNA
<213> ORGANISM: Artificial Sequence
<220> FEATURE:
<223> OTHER INFORMATION: Oligonucleotide

<400> SEQUENCE: 85
taatacgact cactataggg gaa 23

<210> SEQ ID NO 86
<211> LENGTH: 23
<212> TYPE: DNA
<213> ORGANISM: Artificial Sequence
<220> FEATURE:
<223> OTHER INFORMATION: Oligonucleotide

<400> SEQUENCE: 86
taatacgact cactatcaag gaa 23

<210> SEQ ID NO 87
<211> LENGTH: 23
<212> TYPE: DNA
<213> ORGANISM: Artificial Sequence
<220> FEATURE:
<223> OTHER INFORMATION: Oligonucleotide

<400> SEQUENCE: 87
taatacgact cactacggaa gaa 23

<210> SEQ ID NO 88
<211> LENGTH: 23
<212> TYPE: DNA
<213> ORGANISM: Artificial Sequence
<220> FEATURE:
<223> OTHER INFORMATION: Oligonucleotide

<400> SEQUENCE: 88
taatacgact cactaatact gaa 23

<210> SEQ ID NO 89
<211> LENGTH: 23
<212> TYPE: DNA
<213> ORGANISM: Artificial Sequence
<220> FEATURE:
<223> OTHER INFORMATION: Oligonucleotide

<400> SEQUENCE: 89
taatacgact cactatttcg gaa 23

<210> SEQ ID NO 90
<211> LENGTH: 7206
<212> TYPE: DNA
<213> ORGANISM: Artificial Sequence
<220> FEATURE:
<223> OTHER INFORMATION: Oligonucleotide

<400> SEQUENCE: 90
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480
gacgggcgtt ccttgcgcag ctgtgctcga cgttgtcact gaagcgggaa gggactggct 540
gctattgggc gaagtgccgg ggcaggatct cctgtcatct caccttgctc ctgccgagaa 600
agtatccatc atggctgatg caatgcggcg gctgcatacg cttgatccgg ctacctgccc 660
attcgaccac caagcgaaac atcgcatcga gcgagcacgt actcggatgg aagccggtct 720
tgtcgatcag gatgatctgg acgaagagca tcaggggctc gcgccagccg aactgttcgc 780
caggctcaag gcgcggatgc ccgacggcga ggatctcgtc gtgacccatg gcgatgcctg 840
cttgccgaat atcatggtgg aaaatggccg cttttctgga ttcatcgact gtggccggct 900
gggtgtggcg gaccgctatc aggacatagc gttggctacc cgtgatattg ctgaagagct 960
tggcggcgaa tgggctgacc gcttcctcgt gctttacggt atcgccgctc ccgattcgca 1020
gcgcatcgcc ttctatcgcc ttcttgacga gttcttctga gcgggactct ggggttcgct 1080
agaggatcga tcctttttaa cccatcacat atacctgccg ttcactatta tttagtgaaa 1140
tgagatatta tgatattttc tgaattgtga ttaaaaaggc aactttatgc ccatgcaaca 1200
gaaactataa aaaatacaga gaatgaaaag aaacagatag attttttagt tctttaggcc 1260
cgtagtctgc aaatcctttt atgattttct atcaaacaaa agaggaaaat agaccagttg 1320
caatccaaac gagagtctaa tagaatgagg tcgaaaagta aatcgcgcgg gtttgttact 1380
gataaagcag gcaagaccta aaatgtgtaa agggcaaagt gtatactttg gcgtcacccc 1440
ttacatattt taggtctttt tttattgtgc gtaactaact tgccatcttc aaacaggagg 1500
gctggaagaa gcagaccgct aacacagtac ataaaaaagg agacatgaac gatgaacatc 1560
aaaaagtttg caaaacaagc aacagtatta acctttacta ccgcactgct ggcaggaggc 1620
gcaactcaag cgtttgcgaa agaaacgaac caaaagccat ataaggaaac atacggcatt 1680
tcccatatta cacgccatga tatgctgcaa atccctgaac agcaaaaaaa tgaaaaatat 1740
caagtttctg aatttgattc gtccacaatt aaaaatatct cttctgcaaa aggcctggac 1800
gtttgggaca gctggccatt acaaaacgct gacggcactg tcgcaaacta tcacggctac 1860
cacatcgtct ttgcattagc cggagatcct aaaaatgcgg atgacacatc gatttacatg 1920
ttctatcaaa aagtcggcga aacttctatt gacagctgga aaaacgctgg ccgcgtcttt 1980
aaagacagcg acaaattcga tgcaaatgat tctatcctaa aagaccaaac acaagaatgg 2040
tcaggttcag ccacatttac atctgacgga aaaatccgtt tattctacac tgatttctcc 2100
ggtaaacatt acggcaaaca aacactgaca actgcacaag ttaacgtatc agcatcagac 2160
agctctttga acatcaacgg tgtagaggat tataaatcaa tctttgacgg tgacggaaaa 2220
acgtatcaaa atgtacagca gttcatcgat gaaggcaact acagctcagg cgacaaccat 2280
acgctgagag atcctcacta cgtagaagat aaaggccaca aatacttagt atttgaagca 2340
aacactggaa ctgaagatgg ctaccaaggc gaagaatctt tatttaacaa agcatactat 2400
ggcaaaagca catcattctt ccgtcaagaa agtcaaaaac ttctgcaaag cgataaaaaa 2460
cgcacggctg agttagcaaa cggcgctctc ggtatgattg agctaaacga tgattacaca 2520
ctgaaaaaag tgatgaaacc gctgattgca tctaacacag taacagatga aattgaacgc 2580
gcgaacgtct ttaaaatgaa cggcaaatgg tacctgttca ctgactcccg cggatcaaaa 2640
atgacgattg acggcattac gtctaacgat atttacatgc ttggttatgt ttctaattct 2700
ttaactggcc catacaagcc gctgaacaaa actggccttg tgttaaaaat ggatcttgat 2760
cctaacgatg taacctttac ttactcacac ttcgctgtac ctcaagcgaa aggaaacaat 2820
gtcgtgatta caagctatat gacaaacaga ggattctacg cagacaaaca atcaacgttt 2880
gcgccgagct tcctgctgaa catcaaaggc aagaaaacat ctgttgtcaa agacagcatc 2940
cttgaacaag gacaattaac agttaacaaa taaaaacgca aaagaaaatg ccgatgggta 3000
ccgagcgaaa tgaccgacca agcgacgccc aacctgccat cacgagattt cgattccacc 3060
gccgccttct atgaaaggtt gggcttcgga atcgttttcc gggacgccct cgcggacgtg 3120
ctcatagtcc acgacgcccg tgattttgta gccctggccg acggccagca ggtaggccga 3180
caggctcatg ccggccgccg ccgccttttc ctcaatcgct cttcgttcgt ctggaaggca 3240
gtacaccttg ataggtgggc tgcccttcct ggttggcttg gtttcatcag ccatccgctt 3300
gccctcatct gttacgccgg cggtagccgg ccagcctcgc agagcaggat tcccgttgag 3360
caccgccagg tgcgaataag ggacagtgaa gaaggaacac ccgctcgcgg gtgggcctac 3420
ttcacctatc ctgcccggct gacgccgttg gatacaccaa ggaaagtcta cacgaaccct 3480
ttggcaaaat cctgtatatc gtgcgaaaaa ggatggatat accgaaaaaa tcgctataat 3540
gaccccgaag cagggttatg cagcggaaaa gcgctgcttc cctgctgttt tgtggaatat 3600
ctaccgactg gaaacaggca aatgcaggaa attactgaac tgaggggaca ggcgagagac 3660
gatgccaaag agctcctgaa aatctcgata actcaaaaaa tacgcccggt agtgatctta 3720
tttcattatg gtgaaagttg gaacctctta cgtgccgatc aacgtctcat tttcgccaaa 3780
agttggccca gggcttcccg gtatcaacag ggacaccagg atttatttat tctgcgaagt 3840
gatcttccgt cacaggtatt tattcggcgc aaagtgcgtc gggtgatgct gccaacttac 3900
tgatttagtg tatgatggtg tttttgaggt gctccagtgg cttctgtttc tatcagctcc 3960
tgaaaatctc gataactcaa aaaatacgcc cggtagtgat cttatttcat tatggtgaaa 4020
gttggaacct cttacgtgcc gatcaacgtc tcattttcgc caaaagttgg cccagggctt 4080
cccggtatca acagggacac caggatttat ttattctgcg aagtgatctt ccgtcacagg 4140
tatttattcg gcgcaaagtg cgtcgggtga tgctgccaac ttactgattt agtgtatgat 4200
ggtgtttttg aggtgctcca gtggcttctg tttctatcag ggctggatga tcctccagcg 4260
cggggatctc atgctggagt tcttcgccca ccccaaaagg atctaggtga agatcctttt 4320
tgataatctc atgaccaaaa tcccttaacg tgagttttcg ttccactgag cgtcagaccc 4380
cgtagaaaag atcaaaggat cttcttgaga tccttttttt ctgcgcgtaa tctgctgctt 4440
gcaaacaaaa aaaccaccgc taccagcggt ggtttgtttg ccggatcaag agctaccaac 4500
tctttttccg aaggtaactg gcttcagcag agcgcagata ccaaatactg ttcttctagt 4560
gtagccgtag ttaggccacc acttcaagaa ctctgtagca ccgcctacat acctcgctct 4620
gctaatcctg ttaccagtgg ctgctgccag tggcgataag tcgtgtctta ccgggttgga 4680
ctcaagacga tagttaccgg ataaggcgca gcggtcgggc tgaacggggg gttcgtgcac 4740
acagcccagc ttggagcgaa cgacctacac cgaactgaga tacctacagc gtgagctatg 4800
agaaagcgcc acgcttcccg aagggagaaa ggcggacagg tatccggtaa gcggcagggt 4860
cggaacagga gagcgcacga gggagcttcc agggggaaac gcctggtatc tttatagtcc 4920
tgtcgggttt cgccacctct gacttgagcg tcgatttttg tgatgctcgt caggggggcg 4980
gagcctatgg aaaaacgcca gcaacgcggc ctttttacgg ttcctggcct tttgctggcc 5040
ttttgctcac atgttctttc ctgcgttatc ccctgattct gtggataacc gtattaccgc 5100
ctttgagtga gctgataccg ctcgccgcag ccgaacgacc gagcgcagcg agtcagtgag 5160
cgaggaagcg gaagagcgcc caatacgcaa accgcctctc cccgcgcgtt ggccgattca 5220
ttaatgcagc tggcacgaca ggtttcccga ctggaaagcg ggcagtgagc gcaacgcaat 5280
taatgtgagt tagctcactc attaggcacc ccaggcttta cactttatgc ttccggctcg 5340
tatgttgtgt ggaattgtga gcggataaca atttcacaca ggaaacagct atgacatgat 5400
tacgaattcc ttgcctctgc cggaaacccg tctgcagcgg cgccaggcat gaaaaagccc 5460
ggcctatgca ggccgggctc tggtaagggt gcgaaccctc aattcagcgg ttcgatcacc 5520
ttgactgcct gctgctcgcg ggcagcgggc cattcttgtt gcagggtctg cagcacgcgg 5580
ccaacgaatt cagtgtcggc ggcggctttc ttgccgacgt aaccttggcc acggcggtag 5640
accttgaagc gggcacgcat gctgggcagg tgctcttcaa attcatcttc gacggtgttc 5700
ggtggcaggc ggtcgaggcg cacttcaccg gtttggctaa cccacagcaa atggtcgtca 5760
aggctgtcct tgcgcacggc gaacagctgg gccaattggt cgatagtcgg attgttgttc 5820
aagttcatca taaagccccc attacccatt cataggtgat tttcacagtt ggcgctatca 5880
cggtgtagcg cactaccaag gctgctacag cagcatcgca acaggggctt tctcacgctg 5940
ccttttggac agtttccctc tccacggacg gcctgcgtta ccgcgcaggc cgtctggaac 6000
acccttgcca ccgctcccga tcggggagac ggcttcatca tgcccaagcg cgatgaacgg 6060
cgtcaaccat tttgtagtga atatttttgc tcactacatt ctgtcgtttt gtccgacaat 6120
caacgcgagc gttaggatcc ttgcttcccg ggtaccattc tagaggtgag tccttttgtg 6180
gagcgtgtcc gttgagcgat accactcggg gttccggcgt tagcgacggg gagccaaaga 6240
ccttatcgtc tgcccaccca ccatgacaag atggatacag tgatgaagta tttgcgcatg 6300
ttatttgaca atttcaccct ggccttgctc ggtgtggtac tcatcgccac cgtactgcct 6360
tgctcgggcg atggcgcggt gtatttcggc tggctgacca acctggccat tggcctgttg 6420
ttcttcctgc atggcgccaa actgtcccgt gaagccatca ttgccggtgc cgggcactgg 6480
cgcctgcacc tactggtgtt ctcctgtact ttcgtattgt tcccgctgct gggcctggcg 6540
ttcaaacctc tgttcgtacc gctggtgggt aacgagcttt atctgggcat cctgtacctg 6600
tgtgccttgc ctgcaaccgt gcagtcggcc attgccttta cctcgctggc ccgcggtaac 6660
gtgccagcgg ccatctgcag cgcggcggcc tccagcctgc tgggtatctt cctcaccccg 6720
ttgctggtga tgctgctact gggcgccggt ggtgatacag gttccggcct ggatgcggtg 6780
ttgaagatca ctttgcagct gctggtgccg ttcgttgccg ggcaggtcgc gcggcgctgg 6840
atcggcgcct gggtcaagcg caatgcgcgc tggctcaagg tggtggacca gggttcgatc 6900
ctgctggtgg tgtacaccgc cttcagtgag gccgtggtta caagcttggc actggccgtc 6960
gttttacaac gtcgtgactg ggaaaaccct ggcgttaccc aacttaatcg ccttgcagca 7020
catccccctt tcgccagctg gcgtaatagc gaagaggccc gcaccgatcg cccttcccaa 7080
cagttgcgca gcctgaatgg cgaatggcga taagctagct tcacgctgcc gcaagcactc 7140
agggcgcaag ggctgctaaa ggaagcggaa cacgtagaaa gccagtccgc agaaacggtg 7200
ctgacc 7206

<210> SEQ ID NO 91
<211> LENGTH: 7617
<212> TYPE: DNA
<213> ORGANISM: Artificial Sequence
<220> FEATURE:
<223> OTHER INFORMATION: Oligonucleotide

<400> SEQUENCE: 91
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480

-continued

```
gacgggcgtt ccttgcgcag ctgtgctcga cgttgtcact gaagcgggaa gggactggct    540
gctattgggc gaagtgccgg ggcaggatct cctgtcatct caccttgctc ctgccgagaa    600
agtatccatc atggctgatg caatgcggcg gctgcatacg cttgatccgg ctacctgccc    660
attcgaccac caagcgaaac atcgcatcga gcgagcacgt actcggatgg aagccggtct    720
tgtcgatcag gatgatctgg acgaagagca tcaggggctc gcgccagccg aactgttcgc    780
caggctcaag gcgcggatgc ccgacggcga ggatctcgtc gtgacccatg gcgatgcctg    840
cttgccgaat atcatggtgg aaaatggccg cttttctgga ttcatcgact gtggccggct    900
gggtgtggcg gaccgctatc aggacatagc gttggctacc cgtgatattg ctgaagagct    960
tggcggcgaa tgggctgacc gcttcctcgt gctttacggt atcgccgctc ccgattcgca   1020
gcgcatcgcc ttctatcgcc ttcttgacga gttcttctga gcgggactct ggggttcgct   1080
agaggatcga tcctttttaa cccatcacat atacctgccg ttcactatta tttagtgaaa   1140
tgagatatta tgatattttc tgaattgtga ttaaaaaggc aactttatgc ccatgcaaca   1200
gaaactataa aaaatacaga gaatgaaaag aaacagatag atttttagt tctttaggcc   1260
cgtagtctgc aaatcctttt atgattttct atcaaacaaa agaggaaaat agaccagttg   1320
caatccaaac gagagtctaa tagaatgagg tcgaaaagta aatcgcgcgg gtttgttact   1380
gataaagcag gcaagaccta aaatgtgtaa agggcaaagt gtatactttg gcgtcacccc   1440
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
```

gcgccgagct tcctgctgaa catcaaaggc aagaaaacat ctgttgtcaa agacagcatc 2940
cttgaacaag gacaattaac agttaacaaa taaaaacgca aaagaaaatg ccgatgggta 3000
ccgagcgaaa tgaccgacca agcgacgccc aacctgccat cacgagattt cgattccacc 3060
gccgccttct atgaaaggtt gggcttcgga atcgttttcc gggacgccct cgcggacgtg 3120
ctcatagtcc acgacgcccg tgattttgta gccctggccg acggccagca ggtaggccga 3180
caggctcatg ccggccgccg ccgccttttc ctcaatcgct cttcgttcgt ctggaaggca 3240
gtacaccttg ataggtgggc tgcccttcct ggttggcttg gtttcatcag ccatccgctt 3300
gccctcatct gttacgccgg cggtagccgg ccagcctcgc agagcaggat tcccgttgag 3360
caccgccagg tgcgaataag ggacagtgaa gaaggaacac ccgctcgcgg gtgggcctac 3420
ttcacctatc ctgcccggct gacgccgttg gatacaccaa ggaaagtcta cacgaaccct 3480
ttggcaaaat cctgtatatc gtgcgaaaaa ggatggatat accgaaaaaa tcgctataat 3540
gaccccgaag cagggttatg cagcggaaaa gcgctgcttc cctgctgttt tgtggaatat 3600
ctaccgactg gaaacaggca aatgcaggaa attactgaac tgaggggaca ggcgagagac 3660
gatgccaaag agctcctgaa aatctcgata actcaaaaaa tacgcccggt agtgatctta 3720
tttcattatg gtgaaagttg gaacctctta cgtgccgatc aacgtctcat tttcgccaaa 3780
agttggccca gggcttcccg gtatcaacag ggacaccagg atttatttat tctgcgaagt 3840
gatcttccgt cacaggtatt tattcggcgc aaagtgcgtc gggtgatgct gccaacttac 3900
tgatttagtg tatgatggtg tttttgaggt gctccagtgg cttctgtttc tatcagctcc 3960
tgaaaatctc gataactcaa aaaatacgcc cggtagtgat cttatttcat tatggtgaaa 4020
gttggaacct cttacgtgcc gatcaacgtc tcattttcgc caaaagttgg cccagggctt 4080
cccggtatca acagggacac caggatttat ttattctgcg aagtgatctt ccgtcacagg 4140
tatttattcg gcgcaaagtg cgtcgggtga tgctgccaac ttactgattt agtgtatgat 4200
ggtgtttttg aggtgctcca gtggcttctg tttctatcag ggctggatga tcctccagcg 4260
cggggatctc atgctggagt tcttcgccca ccccaaaagg atctaggtga agatcctttt 4320
tgataatctc atgaccaaaa tcccttaacg tgagttttcg ttccactgag cgtcagaccc 4380
cgtagaaaag atcaaaggat cttcttgaga tccttttttt ctgcgcgtaa tctgctgctt 4440
gcaaacaaaa aaaccaccgc taccagcggt ggtttgtttg ccggatcaag agctaccaac 4500
tctttttccg aaggtaactg gcttcagcag agcgcagata ccaaatactg ttcttctagt 4560
gtagccgtag ttaggccacc acttcaagaa ctctgtagca ccgcctacat acctcgctct 4620
gctaatcctg ttaccagtgg ctgctgccag tggcgataag tcgtgtctta ccgggttgga 4680
ctcaagacga tagttaccgg ataaggcgca gcggtcgggc tgaacggggg gttcgtgcac 4740
acagcccagc ttggagcgaa cgacctacac cgaactgaga tacctacagc gtgagctatg 4800
agaaagcgcc acgcttcccg aagggagaaa ggcggacagg tatccggtaa gcggcagggt 4860
cggaacagga gagcgcacga gggagcttcc agggggaaac gcctggtatc tttatagtcc 4920
tgtcgggttt cgccacctct gacttgagcg tcgatttttg tgatgctcgt caggggggcg 4980
gagcctatgg aaaaacgcca gcaacgcggc ctttttacgg ttcctggcct tttgctggcc 5040
ttttgctcac atgttctttc ctgcgttatc ccctgattct gtggataacc gtattaccgc 5100
ctttgagtga gctgataccg ctcgccgcag ccgaacgacc gagcgcagcg agtcagtgag 5160
cgaggaagcg gaagagcgcc caatacgcaa accgcctctc cccgcgcgtt ggccgattca 5220

-continued ttaatgcagc tggcacgaca ggtttcccga ctggaaagcg ggcagtgagc gcaacgcaat 5280
taatgtgagt tagctcactc aggaaacagc tatgacatga ttacgaattc gaccgaaaac 5340
atcggtgccc gccgcctgca caccctgctc gagcgtttgc tcgaagaagt gtcgttcagt 5400
gcgggcgacc tggccagcac ccatgacgaa gcgccgatcc agatcgacgc ggcgtatgtg 5460
aacagccacc tgggtgagct ggcacagaac gaagacctgt cgcgttacat tctgtaagac 5520
cggtttcgac agtttcgcgg gcaagcccgc tcctgcacgc gccaccacaa cccttgggcc 5580
tgtggtgatc cgtgcggggg cgggcttgcc cgcgaagagg cccttgaatc cctcccccat 5640
aagctggaag ctgtgcttca tcagctcccg agagattctg cccatggccc gcctgcctac 5700
cgccatcaac ctgcacaaag cctccaagac cctcagcctc acctacgcac ccggcgaggt 5760
ctaccacctg cccgccgaat tcctgcgcgt gcactctccc tccgccgagg tccagggcca 5820
cggcaacccc atcctgcagt tcggcaagat caacgtcggc ctcagtggct tggaacctgc 5880
cggccaatat gcactgaaac tgaccttcga cgacggccat gacagcggct tgttcacttg 5940
ggaatacctt gagcaactgt gcctgcgcca ggaacaactg tgggcagaat acctcgatga 6000
gttgcaaaag gccggcaaat cccgcgaccc agccgaatct gtggtcaagc tcatgctcta 6060
gcgcaaggcc tgcggggttt agagcgcatt ttctaaattc atctgtttga atgacttgca 6120
gacagcccag tgaagggctg tcttgcgcat tacacgaaag tcgggtaacc aatgggtgtg 6180
gcaagttccc tgcatgactt tgcaggtcgg cagaacccac gcagcaccgc tgttccttat 6240
cactggtcac ccgagtagca gtaccgggct cagggctgtg cacccgccac agcaaccggt 6300
actcgtctca ggacaacgga gcgtcgtaga ggatcctaca atagactcta gaaggcacct 6360
acgtgctgac ccgatgagct gctgactgga tgaaaacccg cgatcgtatc cttgaatgcg 6420
ccctgcagtt gttcaaccag cagggcgaac ccaacgtatc caccctggaa attgccaacg 6480
aactcggcat cagcccaggc aacctgtact accacttcca tggcaaggag cccttggttc 6540
tgggcttgtt cgagcgtttt gaagaagcgt tgatgccgtt gctggaccca ccgctggagg 6600
tgcggctgga cgcagaggat tactggctgt ttctgcactt gatcgtcgag cgcatggctc 6660
agtaccgctt cctgttccag gacctgtcca acctgaccgg gcgcctgccc aaactcgccc 6720
gaggcatgcg cagcctgatc aatgcaatca aacgcacgct ggcggcgctg ttggccagcc 6780
tcaagagcca ggggctggta gaaagtgata cccaggcgct ggggcaactg gtcgagcaga 6840
tcacactgac gctgatgttc tcgctggatt accagcgtgt gctggggcgc gagggggatg 6900
tggggatcgt ggtgtatcag gtgatgatgc tggtggcgcc gcatctgcag gcccaggccc 6960
gggcggcggc ggagcagctg gcagtgaagt acctggaggg gtaggcctgc tggagatgta 7020
gtgttgcagc cgacgcattc gcgggtaaac ccgctcctac aaggtttggc gcatcttgta 7080
ggagcgggtt tacccgcgaa gaaggcgacg cggtatcaga tcagggtacc ggtgccagtc 7140
ggtgccgacg gcgtgctgct ggccggggtg gcggcagttg ccggtgctgt ggtcgctgca 7200
ggcgcagcgc tggcagctgg tgctgctggt ttggccgctg ccggtttggc tggagctttc 7260
ttcaccgcag gtttcttggc tgccgcaggt ttggccgctg caggcttggc tgctggctta 7320
gctgcaggtt tttccgctgc ggttttggct gcaagcttgg cactggccgt cgttttacaa 7380
cgtcgtgact gggaaaaccc tggcgttacc caacttaatc gccttgcagc acatccccct 7440
ttcgccagct ggcgtaatag cgaagaggcc cgcaccgatc gcccttccca acagttgcgc 7500
agcctgaatg gcgaatggcg ataagctagc ttcacgctgc cgcaagcact cagggcgcaa 7560
gggctgctaa aggaagcgga acacgtagaa agccagtccg cagaaacggt gctgacc 7617

<210> SEQ ID NO 92
<211> LENGTH: 3298
<212> TYPE: DNA
<213> ORGANISM: Artificial Sequence
<220> FEATURE:
<223> OTHER INFORMATION: Oligonucleotide

<400> SEQUENCE: 92
aaaaggatct aggtgaagat cctttttgat aatctcatga ccaaaatccc ttaacgtgag 60
ttttcgttcc actgagcgtc agaccccgta gaaaagatca aaggatcttc ttgagatcct 120 tttttctgc gcgtaatctg ctgcttgcaa acaaaaaaac caccgctacc agcggtggtt 180
tgtttgccgg atcaagagct accaactctt tttccgaagg taactggctt cagcagagcg 240
cagataccaa atactgttct tctagtgtag ccgtagttag gccaccactt caagaactct 300
gtagcaccgc ctacatacct cgctctgcta atcctgttac cagtggctgc tgccagtggc 360
gataagtcgt gtcttaccgg gttggactca agacgatagt taccggataa ggcgcagcgg 420
tcgggctgaa cggggggttc gtgcacacag cccagcttgg agcgaacgac ctacaccgaa 480
ctgagatacc tacagcgtga gctatgagaa agcgccacgc ttcccgaagg gagaaaggcg 540
gacaggtatc cggtaagcgg cagggtcgga acaggagagc gcacgaggga gcttccaggg 600
ggaaacgcct ggtatcttta tagtcctgtc gggtttcgcc acctctgact tgagcgtcga 660
tttttgtgat gctcgtcagg ggggcggagc ctatggaaaa acgccagcaa cgcggccttt 720
ttacggttcc tggccttttg ctggcctttt gctcacatgt tctttcctgc gttatcccct 780
gattctgtgg ataaccgtat taccgccttt gagtgagctg ataccgctcg ccgcagccga 840
acgaccgagc gcagcgagtc agtgagcgag gaagcggaag agcgcccaat acgcaaaccg 900
cctctgggag accagaaaca aaaaaaggcc gcgttagcgg ccttcaataa ttggacctgg 960
ctcctaactg atttttaagg cgactgatga gtcgcctttt ttttgtctaa gaattcatca 1020
gaagaactcg tcaagaaggc gatagaaggc gatgcgctgc gaatcgggag cggcgatacc 1080
gtaaagcacg aggaagcggt cagcccattc gccgccaagc tcttcagcaa tatcacgggt 1140
agccaacgct atgtcctgat agcggtccgc cacacccagc cggccacagt cgatgaatcc 1200
agaaaagcgg ccattttcca ccatgatatt cggcaagcag gcatcgccat gggtcacgac 1260
gagatcctcg ccgtcgggca tccgcgcctt gagcctggcg aacagttcgg ctggcgcgag 1320
cccctgatgc tcttcgtcca gatcatcctg atcgacaaga ccggcttcca tccgagtacg 1380
tgctcgctcg atgcgatgtt tcgcttggtg gtcgaatggg caggtagccg gatcaagcgt 1440
atgcagccgc cgcattgcat cagccatgat ggatactttc tcggcaggag caaggtgaga 1500
tgacaggaga tcctgccccg gcacttcgcc caatagcagc cagtcccttc ccgcttcagt 1560
gacaacgtcg agcacagctg cgcaaggaac gcccgtcgtg gccagccacg atagccgcgc 1620
tgcctcgtct tggagttcat tcagggcacc ggacaggtcg gtcttgacaa aaagaaccgg 1680
gcgcccctgc gctgacagcc ggaacacggc ggcatcagag cagccgattg tctgttgtgc 1740
ccagtcatag ccgaatagcc tctccaccca agcggccgga gaacctgcgt gcaatccatc 1800
ttgttcaatc atgcgaaacg atcctcatcc tgtctcttga tcagatcttg atcccctgcg 1860
ccatcagatc cttggcggca agaaagccat ccagtttact ttgcagggct tcccaacctt 1920
accagagggc gccccagctg gcaattccgg ttcgcttgct gtccataaaa ccgcccagtc 1980
tagctatcgc catgtaagcc cactgcaagc tacctgcttt ctctttgcgc ttgcgttttc 2040

```
ccttgtccag atagcccagt agctgacatt catccgggac gtcgtgcccc aactggggta   2100
acctttgagt tctctcagtt gggggatcga tagtcaaaag cctccggtcg gaggcttttg   2160
actagcacct cggtaccaaa ttccagaaaa gaggcctccc gaaagggggg cctttttcg   2220
ttttggtcca ctagtagtct tagtcttcac cgatgagcta cccagtagta gaagacaact   2280
taagattaac tcacacagga gatatcatat ggtgtccaaa ggggaagagg acaatatggc   2340
atcgttgcca gctacgcatg aactgcacat cttcggctcg attaacggtg tcgatttcga   2400
tatggtcggc cagggtacgg ggaatcctaa cgacggttat gaggagctga acctcaaatc   2460
gacgaagggg gatctccagt ttagcccctg gattttggtc ccacatattg gttacggctt   2520
tcatcagtac ctcccgtatc cggacggtat gagccctttt caagctgcta tggtggacgg   2580
tagcggttac caagtccacc ggaccatgca gtttgaggat ggggcatcgc tgacggtcaa   2640
ctaccgttat acctacgaag gtagccatat taagggcgaa gctcaagtga agggtaccgg   2700
ctttccggcg gacggtccgg tgatgacgaa ctccctcacc gccgccgatt ggtgtcgtag   2760
caagaaaacc tatccgaatg acaaaaccat catctcgacg tttaagtgga gctatacgac   2820
gggtaatggc aagcgctacc gttcgacggc acgtaccacc tacacgtttg caaagcctat   2880
ggctgcaaat tacctcaaga atcaacctat gtatgtgttc cggaaaacgg aactcaaaca   2940
tagcaaaacg gaactgaact tcaaagagtg gcagaaagct ttcacggatg tcatgggtat   3000
ggacgaactc tataaataat ctagagacga acaataaggc ctccctaacg gggggccttt   3060
tttattgata acaaaaatcc acaaggaaaa attaaagggg agataaaatc cccccttttt   3120
ggttaactgc ggccgcgtcg tggtttgtct ggtcaaccac cgcggtctca gtggtgtacg   3180
gtacaaaccc cgacgctagc aacgcatgag aaagcccccg gaagatcacc ttccgggggc   3240
tttttattg cgctgcgggt gccagggcgt gcccttgggc tccccgggcg cgtactcc     3298
```

<210> SEQ ID NO 93
<211> LENGTH: 7127
<212> TYPE: DNA
<213> ORGANISM: Artificial Sequence
<220> FEATURE:
<223> OTHER INFORMATION: Oligonucleotide

<400> SEQUENCE: 93

```
ccggatgaat gtcagctact gggctatctg gacaagggaa aacgcaagcg caaagagaaa     60
gcaggtagct tgcagtgggc ttacatggcg atagctagac tgggcggttt tatggacagc    120
aagcgaaccg gaattgccag ctggggcgcc ctctggtaag gttgggaagc cctgcaaagt    180
aaactggatg gctttcttgc cgccaaggat ctgatggcgc aggggatcaa gatctgatca    240
agagacagga tgaggatcgt ttcgcatgat tgaacaagat ggattgcacg caggttctcc    300
ggccgcttgg gtggagaggc tattcggcta tgactgggca caacagacaa tcggctgctc    360
tgatgccgcc gtgttccggc tgtcagcgca ggggcgcccg gttctttttg tcaagaccga    420
cctgtccggt gccctgaatg aactccaaga cgaggcagcg cggctatcgt ggctggccac    480
gacgggcgtt ccttgcgcag ctgtgctcga cgttgtcact gaagcgggaa gggactggct    540
gctattgggc gaagtgccgg ggcaggatct cctgtcatct caccttgctc ctgccgagaa    600
agtatccatc atggctgatg caatgcggcg gctgcatacg cttgatccgg ctacctgccc    660
attcgaccac caagcgaaac atcgcatcga gcgagcacgt actcggatgg aagccggtct    720
tgtcgatcag gatgatctgg acgaagagca tcaggggctc gcgccagccg aactgttcgc    780
caggctcaag gcgcggatgc ccgacggcga ggatctcgtc gtgacccatg gcgatgcctg    840
```

cttgccgaat atcatggtgg aaaatggccg cttttctgga ttcatcgact gtggccggct 900
gggtgtggcg gaccgctatc aggacatagc gttggctacc cgtgatattg ctgaagagct 960
tggcggcgaa tgggctgacc gcttcctcgt gctttacggt atcgccgctc ccgattcgca 1020
gcgcatcgcc ttctatcgcc ttcttgacga gttcttctga gcgggactct ggggttcgct 1080
agaggatcga tcctttttaa cccatcacat atacctgccg ttcactatta tttagtgaaa 1140
tgagatatta tgatattttc tgaattgtga ttaaaaaggc aactttatgc ccatgcaaca 1200
gaaactataa aaaatacaga gaatgaaaag aaacagatag atttttagt tctttaggcc 1260 cgtagtctgc aaatcctttt atgattttct atcaaacaaa agaggaaaat agaccagttg 1320
caatccaaac gagagtctaa tagaatgagg tcgaaaagta aatcgcgcgg gtttgttact 1380
gataaagcag gcaagaccta aaatgtgtaa agggcaaagt gtatactttg gcgtcacccc 1440
ttacatattt taggtctttt tttattgtgc gtaactaact tgccatcttc aaacaggagg 1500
gctggaagaa gcagaccgct aacacagtac ataaaaaagg agacatgaac gatgaacatc 1560
aaaaagtttg caaaacaagc aacagtatta acctttacta ccgcactgct ggcaggaggc 1620
gcaactcaag cgtttgcgaa agaaacgaac caaaagccat ataaggaaac atacggcatt 1680
tcccatatta cacgccatga tatgctgcaa atccctgaac agcaaaaaaa tgaaaaatat 1740
caagtttctg aatttgattc gtccacaatt aaaaatatct cttctgcaaa aggcctggac 1800
gtttgggaca gctggccatt acaaaacgct gacggcactg tcgcaaacta tcacggctac 1860
cacatcgtct ttgcattagc cggagatcct aaaaatgcgg atgacacatc gatttacatg 1920
ttctatcaaa aagtcggcga aacttctatt gacagctgga aaaacgctgg ccgcgtcttt 1980
aaagacagcg acaaattcga tgcaaatgat tctatcctaa aagaccaaac acaagaatgg 2040
tcaggttcag ccacatttac atctgacgga aaaatccgtt tattctacac tgatttctcc 2100
ggtaaacatt acggcaaaca aacactgaca actgcacaag ttaacgtatc agcatcagac 2160
agctctttga acatcaacgg tgtagaggat tataaatcaa tctttgacgg tgacggaaaa 2220
acgtatcaaa atgtacagca gttcatcgat gaaggcaact acagctcagg cgacaaccat 2280
acgctgagag atcctcacta cgtagaagat aaaggccaca aatacttagt atttgaagca 2340
aacactggaa ctgaagatgg ctaccaaggc gaagaatctt tatttaacaa agcatactat 2400
ggcaaaagca catcattctt ccgtcaagaa agtcaaaaac ttctgcaaag cgataaaaaa 2460
cgcacggctg agttagcaaa cggcgctctc ggtatgattg agctaaacga tgattacaca 2520
ctgaaaaaag tgatgaaacc gctgattgca tctaacacag taacagatga aattgaacgc 2580
gcgaacgtct ttaaaatgaa cggcaaatgg tacctgttca ctgactcccg cggatcaaaa 2640
atgacgattg acggcattac gtctaacgat atttacatgc ttggttatgt ttctaattct 2700
ttaactggcc catacaagcc gctgaacaaa actggccttg tgttaaaaat ggatcttgat 2760
cctaacgatg taacctttac ttactcacac ttcgctgtac ctcaagcgaa aggaaacaat 2820
gtcgtgatta caagctatat gacaaacaga ggattctacg cagacaaaca atcaacgttt 2880
gcgccgagct tcctgctgaa catcaaaggc aagaaaacat ctgttgtcaa agacagcatc 2940
cttgaacaag gacaattaac agttaacaaa taaaaacgca aaagaaaatg ccgatgggta 3000
ccgagcgaaa tgaccgacca agcgacgccc aacctgccat cacgagattt cgattccacc 3060
gccgccttct atgaaaggtt gggcttcgga atcgttttcc gggacgccct cgcggacgtg 3120
ctcatagtcc acgacgcccg tgattttgta gccctggccg acggccagca ggtaggccga 3180

-continued

```
caggctcatg ccggccgccg ccgccttttc ctcaatcgct cttcgttcgt ctggaaggca   3240

gtacaccttg ataggtgggc tgcccttcct ggttggcttg gtttcatcag ccatccgctt   3300

gccctcatct gttacgccgg cggtagccgg ccagcctcgc agagcaggat tcccgttgag   3360

caccgccagg tgcgaataag ggacagtgaa gaaggaacac ccgctcgcgg gtgggcctac   3420

ttcacctatc ctgcccggct gacgccgttg gatacaccaa ggaaagtcta cacgaaccct   3480

ttggcaaaat cctgtatatc gtgcgaaaaa ggatggatat accgaaaaaa tcgctataat   3540

gaccccgaag cagggttatg cagcggaaaa gcgctgcttc cctgctgttt tgtggaatat   3600

ctaccgactg gaaacaggca aatgcaggaa attactgaac tgaggggaca ggcgagagac   3660

gatgccaaag agctcctgaa aatctcgata actcaaaaaa tacgcccggt agtgatctta   3720

tttcattatg gtgaaagttg gaacctctta cgtgccgatc aacgtctcat tttcgccaaa   3780

agttggccca gggcttcccg gtatcaacag ggacaccagg atttatttat tctgcgaagt   3840

gatcttccgt cacaggtatt tattcggcgc aaagtgcgtc gggtgatgct gccaacttac   3900

tgatttagtg tatgatggtg tttttgaggt gctccagtgg cttctgtttc tatcagctcc   3960

tgaaaatctc gataactcaa aaaatacgcc cggtagtgat cttatttcat tatggtgaaa   4020

gttggaacct cttacgtgcc gatcaacgtc tcattttcgc caaaagttgg cccagggctt   4080

cccggtatca acagggacac caggatttat ttattctgcg aagtgatctt ccgtcacagg   4140

tatttattcg gcgcaaagtg cgtcgggtga tgctgccaac ttactgattt agtgtatgat   4200

ggtgtttttg aggtgctcca gtggcttctg tttctatcag ggctggatga tcctccagcg   4260

cggggatctc atgctggagt tcttcgccca ccccaaaagg atctaggtga agatcctttt   4320

tgataatctc atgaccaaaa tcccttaacg tgagttttcg ttccactgag cgtcagaccc   4380

cgtagaaaag atcaaaggat cttcttgaga tccttttttt ctgcgcgtaa tctgctgctt   4440

gcaaacaaaa aaaccaccgc taccagcggt ggtttgtttg ccggatcaag agctaccaac   4500

tctttttccg aaggtaactg gcttcagcag agcgcagata ccaaatactg ttcttctagt   4560

gtagccgtag ttaggccacc acttcaagaa ctctgtagca ccgcctacat acctcgctct   4620

gctaatcctg ttaccagtgg ctgctgccag tggcgataag tcgtgtctta ccgggttgga   4680

ctcaagacga tagttaccgg ataaggcgca gcggtcgggc tgaacggggg gttcgtgcac   4740

acagcccagc ttggagcgaa cgacctacac cgaactgaga tacctacagc gtgagctatg   4800

agaaagcgcc acgcttcccg aagggagaaa ggcggacagg tatccggtaa gcggcagggt   4860

cggaacagga gagcgcacga gggagcttcc agggggaaac gcctggtatc tttatagtcc   4920

tgtcgggttt cgccacctct gacttgagcg tcgatttttg tgatgctcgt caggggggcg   4980

gagcctatgg aaaaacgcca gcaacgcggc ctttttacgg ttcctggcct tttgctggcc   5040

ttttgctcac atgttctttc ctgcgttatc ccctgattct gtggataacc gtattaccgc   5100

ctttgagtga gctgataccg ctcgccgcag ccgaacgacc gagcgcagcg agtcagtgag   5160

cgaggaagcg gaagagcgcc caatacgcaa accgcctctc cccgcgcgtt ggccgattca   5220

ttaatgcagc tggcacgaca ggtttcccga ctggaaagcg ggcagtgagc gcaacgcaat   5280

taatgtgagt tagctcactc aggaaacagc tatgacatga ttacgaattc cttgcctctg   5340

ccggaaaccc gtctgcagcg gcgccaggca tgaaaaagcc cggcctatgc aggccgggct   5400

ctggtaaggg tgcgaaccct caattcagcg gttcgatcac cttgactgcc tgctgctcgc   5460

gggcagcggg ccattcttgt tgcagggtct gcagcacgcg gccaacgaat tcagtgtcgg   5520

cggcggcttt cttgccgacg taaccttggc cacggcggta gaccttgaag cgggcacgca   5580
```

tgctgggcag gtgctcttca aattcatctt cgacggtgtt cggtggcagg cggtcgaggc 5640
gcacttcacc ggtttggcta acccacagca aatggtcgtc aaggctgtcc ttgcgcacgg 5700
cgaacagctg ggccaattgg tcgatagtcg gattgttgtt caagttcatc ataaagcccc 5760
cattacccat tcataggtga ttttcacagt tggcgctatc acggtgtagc gcactaccaa 5820
ggctgctaca gcagcatcgc aacaggggct ttctcacgct gccttttgga cagtttccct 5880
ctccacggac ggcctgcgtt accgcgcagg ccgtctggaa cacccttgcc accgctcccg 5940
atcggggaga cggcttcatc atgcccaagc gcgatgaacg gcgtcaacca ttttgtagtg 6000
aatatttttg ctcactacat tctgtcgttt tgtccgacaa tcaacgcgag cgttaggatc 6060
cttgcttccc gggtaccatt ctagaggtga gtccttttgt ggagcgtgtc cgttgagcga 6120
taccactcgg ggttccggcg ttagcgacgg ggagccaaag accttatcgt ctgcccaccc 6180
accatgacaa gatggataca gtgatgaagt atttgcgcat gttatttgac aatttcaccc 6240
tggccttgct cggtgtggta ctcatcgcca ccgtactgcc ttgctcgggc gatggcgcgg 6300
tgtatttcgg ctggctgacc aacctggcca ttggcctgtt gttcttcctg catggcgcca 6360
aactgtcccg tgaagccatc attgccggtg ccgggcactg gcgcctgcac ctactggtgt 6420
tctcctgtac tttcgtattg ttcccgctgc tgggcctggc gttcaaacct ctgttcgtac 6480
cgctggtggg taacgagctt tatctgggca tcctgtacct gtgtgccttg cctgcaaccg 6540
tgcagtcggc cattgccttt acctcgctgg cccgcggtaa cgtgccagcg gccatctgca 6600
gcgcggcggc ctccagcctg ctgggtatct tcctcacccc gttgctggtg atgctgctac 6660
tgggcgccgg tggtgataca ggttccggcc tggatgcggt gttgaagatc actttgcagc 6720
tgctggtgcc gttcgttgcc gggcaggtcg cgcggcgctg gatcggcgcc tgggtcaagc 6780
gcaatgcgcg ctggctcaag gtggtggacc agggttcgat cctgctggtg gtgtacaccg 6840
ccttcagtga ggccgtggtt acaagcttgg cactggccgt cgttttacaa cgtcgtgact 6900
gggaaaaccc tggcgttacc caacttaatc gccttgcagc acatccccct ttcgccagct 6960
ggcgtaatag cgaagaggcc cgcaccgatc gcccttccca acagttgcgc agcctgaatg 7020
gcgaatggcg ataagctagc ttcacgctgc cgcaagcact cagggcgcaa gggctgctaa 7080
aggaagcgga acacgtagaa agccagtccg cagaaacggt gctgacc 7127

<210> SEQ ID NO 94
<211> LENGTH: 10249
<212> TYPE: DNA
<213> ORGANISM: Artificial Sequence
<220> FEATURE:
<223> OTHER INFORMATION: Oligonucleotide

<400> SEQUENCE: 94
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480

-continued

```
gacgggcgtt ccttgcgcag ctgtgctcga cgttgtcact gaagcgggaa gggactggct    540
gctattgggc gaagtgccgg ggcaggatct cctgtcatct caccttgctc ctgccgagaa    600
agtatccatc atggctgatg caatgcggcg gctgcatacg cttgatccgg ctacctgccc    660
attcgaccac caagcgaaac atcgcatcga gcgagcacgt actcggatgg aagccggtct    720
tgtcgatcag gatgatctgg acgaagagca tcaggggctc gcgccagccg aactgttcgc    780
caggctcaag gcgcggatgc ccgacggcga ggatctcgtc gtgacccatg gcgatgcctg    840
cttgccgaat atcatggtgg aaaatggccg cttttctgga ttcatcgact gtggccggct    900
gggtgtggcg gaccgctatc aggacatagc gttggctacc cgtgatattg ctgaagagct    960
tggcggcgaa tgggctgacc gcttcctcgt gctttacggt atcgccgctc ccgattcgca   1020
gcgcatcgcc ttctatcgcc ttcttgacga gttcttctga gcgggactct ggggttcgct   1080
agaggatcga tcctttttaa cccatcacat atacctgccg ttcactatta tttagtgaaa   1140
tgagatatta tgatattttc tgaattgtga ttaaaaaggc aactttatgc ccatgcaaca   1200
gaaactataa aaaatacaga gaatgaaaag aaacagatag attttttagt tctttaggcc   1260
cgtagtctgc aaatcctttt atgattttct atcaaacaaa agaggaaaat agaccagttg   1320
caatccaaac gagagtctaa tagaatgagg tcgaaaagta aatcgcgcgg gtttgttact   1380
gataaagcag gcaagaccta aaatgtgtaa agggcaaagt gtatactttg gcgtcacccc   1440
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
```

gcgccgagct tcctgctgaa catcaaaggc aagaaaacat ctgttgtcaa agacagcatc 2940
cttgaacaag gacaattaac agttaacaaa taaaaacgca aaagaaaatg ccgatgggta 3000
ccgagcgaaa tgaccgacca agcgacgccc aacctgccat cacgagattt cgattccacc 3060
gccgccttct atgaaaggtt gggcttcgga atcgttttcc gggacgccct cgcggacgtg 3120
ctcatagtcc acgacgcccg tgattttgta gccctggccg acggccagca ggtaggccga 3180
caggctcatg ccggccgccg ccgccttttc ctcaatcgct cttcgttcgt ctggaaggca 3240
gtacaccttg ataggtgggc tgcccttcct ggttggcttg gtttcatcag ccatccgctt 3300
gccctcatct gttacgccgg cggtagccgg ccagcctcgc agagcaggat tcccgttgag 3360
caccgccagg tgcgaataag ggacagtgaa gaaggaacac ccgctcgcgg gtgggcctac 3420
ttcacctatc ctgcccggct gacgccgttg gatacaccaa ggaaagtcta cacgaaccct 3480
ttggcaaaat cctgtatatc gtgcgaaaaa ggatggatat accgaaaaaa tcgctataat 3540
gaccccgaag cagggttatg cagcggaaaa gcgctgcttc cctgctgttt tgtggaatat 3600
ctaccgactg gaaacaggca aatgcaggaa attactgaac tgaggggaca ggcgagagac 3660
gatgccaaag agctcctgaa aatctcgata actcaaaaaa tacgcccggt agtgatctta 3720
tttcattatg gtgaaagttg gaacctctta cgtgccgatc aacgtctcat tttcgccaaa 3780
agttggccca gggcttcccg gtatcaacag ggacaccagg atttatttat tctgcgaagt 3840
gatcttccgt cacaggtatt tattcggcgc aaagtgcgtc gggtgatgct gccaacttac 3900
tgatttagtg tatgatggtg tttttgaggt gctccagtgg cttctgtttc tatcagctcc 3960
tgaaaatctc gataactcaa aaaatacgcc cggtagtgat cttatttcat tatggtgaaa 4020
gttggaacct cttacgtgcc gatcaacgtc tcattttcgc caaaagttgg cccagggctt 4080
cccggtatca acagggacac caggatttat ttattctgcg aagtgatctt ccgtcacagg 4140
tatttattcg gcgcaaagtg cgtcgggtga tgctgccaac ttactgattt agtgtatgat 4200
ggtgtttttg aggtgctcca gtggcttctg tttctatcag ggctggatga tcctccagcg 4260
cggggatctc atgctggagt tcttcgccca ccccaaaagg atctaggtga agatcctttt 4320
tgataatctc atgaccaaaa tcccttaacg tgagttttcg ttccactgag cgtcagaccc 4380
cgtagaaaag atcaaaggat cttcttgaga tccttttttt ctgcgcgtaa tctgctgctt 4440
gcaaacaaaa aaaccaccgc taccagcggt ggtttgtttg ccggatcaag agctaccaac 4500
tctttttccg aaggtaactg gcttcagcag agcgcagata ccaaatactg ttcttctagt 4560
gtagccgtag ttaggccacc acttcaagaa ctctgtagca ccgcctacat acctcgctct 4620
gctaatcctg ttaccagtgg ctgctgccag tggcgataag tcgtgtctta ccgggttgga 4680
ctcaagacga tagttaccgg ataaggcgca gcggtcgggc tgaacggggg gttcgtgcac 4740
acagcccagc ttggagcgaa cgacctacac cgaactgaga tacctacagc gtgagctatg 4800
agaaagcgcc acgcttcccg aagggagaaa ggcggacagg tatccggtaa gcggcagggt 4860
cggaacagga gagcgcacga gggagcttcc agggggaaac gcctggtatc tttatagtcc 4920
tgtcgggttt cgccacctct gacttgagcg tcgatttttg tgatgctcgt caggggggcg 4980
gagcctatgg aaaaacgcca gcaacgcggc ctttttacgg ttcctggcct tttgctggcc 5040
ttttgctcac atgttctttc ctgcgttatc ccctgattct gtggataacc gtattaccgc 5100
ctttgagtga gctgataccg ctcgccgcag ccgaacgacc gagcgcagcg agtcagtgag 5160
cgaggaagcg gaagagcgcc caatacgcaa accgcctctc cccgcgcgtt ggccgattca 5220

-continued

```
ttaatgcagc tggcacgaca ggtttcccga ctggaaagcg ggcagtgagc gcaacgcaat   5280
taatgtgagt tagctcactc aggaaacagc tatgacatga ttacgaattc cttgcctctg   5340
ccggaaaccc gtctgcagcg gcgccaggca tgaaaaagcc cggcctatgc aggccgggct   5400
ctggtaaggg tgcgaaccct caattcagcg gttcgatcac cttgactgcc tgctgctcgc   5460
gggcagcggg ccattcttgt tgcagggtct gcagcacgcg gccaacgaat tcagtgtcgg   5520
cggcggcttt cttgccgacg taaccttggc cacggcggta gaccttgaag cgggcacgca   5580
tgctgggcag gtgctcttca aattcatctt cgacggtgtt cggtggcagg cggtcgaggc   5640
gcacttcacc ggtttggcta acccacagca aatggtcgtc aaggctgtcc ttgcgcacgg   5700
cgaacagctg ggccaattgg tcgatagtcg gattgttgtt caagttcatc ataaagcccc   5760
cattacccat tcataggtga ttttcacagt tggcgctatc acggtgtagc gcactaccaa   5820
ggctgctaca gcagcatcgc aacaggggct ttctcacgct gccttttgga cagtttccct   5880
ctccacggac ggcctgcgtt accgcgcagg ccgtctggaa caccctttgcc accgctcccg   5940
atcggggaga cggcttcatc atgcccaagc gcgatgaacg gcgtcaacca ttttgtagtg   6000
aatattttttg ctcactacat tctgtcgttt tgtccgacaa tcaacgcgag cgttaggatc   6060
ccatcgccag tgacagactg gcttcagacc ggtcttgccg cgcgagtgcg gcaagaccct   6120
tccacacgca acacaaggga aaccgcatga acacgattaa catcgctaag aacgacttct   6180
ctgacatcga actggctgct atcccgttca acactctggc tgaccattac ggtgagcgtt   6240
tagctcgcga acagttggcc cttgagcatg agtcttacga gatgggtgaa gcacgcttcc   6300
gcaagatgtt tgagcgtcaa cttaaagctg gtgaggttgc ggataacgct gccgccaagc   6360
ctctcatcac taccctactc cctaagatga ttgcacgcat caacgactgg tttgaggaag   6420
tgaaagctaa gcgcggcaag cgcccgacag ccttccagtt cctgcaagaa atcaagccgg   6480
aagccgtagc gtacatcacc attaagacca ctctggcttg cctaaccagt gctgacaata   6540
caaccgttca ggctgtagca agcgcaatcg gtcgggccat tgaggacgag gctcgcttcg   6600
gtcgtatccg tgaccttgaa gctaagcact tcaagaaaaa cgttgaggaa caactcaaca   6660
agcgcgtagg gcacgtctac aagaaagcat ttatgcaagt tgtcgaggct gacatgctct   6720
ctaagggtct actcggtggc gaggcgtggt cttcgtggca taaggaagac tctattcatg   6780
taggagtacg ctgcatcgag atgctcattg agtcaaccgg aatggttagc ttacaccgcc   6840
aaaatgctgg cgtagtaggt caagactctg agactatcga actcgcacct gaatacgctg   6900
aggctatcgc aacccgtgca ggtgcgctgg ctggcatctc tccgatgttc caaccttgcg   6960
tagttcctcc taagccgtgg actggcatta ctggtggtgg ctattgggct aacggtcgtc   7020
gtcctctggc gctggtgcgt actcacagta agaaagcact gatgcgctac gaagacgttt   7080
acatgcctga ggtgtacaaa gcgattaaca ttgcgcaaaa caccgcatgg aaaatcaaca   7140
agaaagtcct agcggtcgcc aacgtaatca ccaagtggaa gcattgtccg gtcgaggaca   7200
tccctgcgat tgagcgtgaa gaactcccga tgaaaccgga agacatcgac atgaatcctg   7260
aggctctcac cgcgtggaaa cgtgctgccg ctgctgtgta ccgcaaggac aaggctcgca   7320
agtctcgccg tatcagcctt gagttcatgc ttgagcaagc caataagttt gctaaccata   7380
aggccatctg gttcccttac aacatggact ggcgcggtcg tgtttacgct gtgtcaatgt   7440
tcaacccgca aggtaacgat atgaccaaag gactgcttac gctggcgaaa ggtaaaccaa   7500
tcggtaagga aggttactac tggctgaaaa tccacggtgc aaactgtgcg ggtgtcgata   7560
aggttccgtt ccctgagcgc atcaagttca ttgaggaaaa ccacgagaac atcatggctt   7620
```

gcgctaagtc tccactggag aacacttggt gggctgagca agattctccg ttctgcttcc 7680
ttgcgttctg ctttgagtac gctggggtac agcaccacgg cctgagctat aactgctccc 7740
ttccgctggc gtttgacggg tcttgctctg gcatccagca cttctccgcg atgctccgag 7800
atgaggtagg tggtcgcgcg gttaacttgc ttcctagtga aaccgttcag gacatctacg 7860
ggattgttgc taagaaagtc aacgagattc tacaagcaga cgcaatcaat gggaccgata 7920
acgaagtagt taccgtgacc gatgagaaca ctggtgaaat ctctgagaaa gtcaagctgg 7980
gcactaaggc actggctggt caatggctgg cttacggtgt tactcgcagt gtgactaagc 8040
gttcagtcat gacgctggct tacgggtcca aagagttcgg cttccgtcaa caagtgctgg 8100
aagataccat tcagccagct attgattccg gcaagggtct gatgttcact cagccgaatc 8160
aggctgctgg atacatggct aagctgattt gggaatctgt gagcgtgacg gtggtagctg 8220
cggttgaagc aatgaactgg cttaagtctg ctgctaagct gctggctgct gaggtcaaag 8280
ataagaagac tggagagatt cttcgcaagc gttgcgctgt gcattgggta actcctgatg 8340
gtttccctgt gtggcaggaa tacaagaagc ctattcagac gcgcttgaac ctgatgttcc 8400
tcggtcagtt ccgcttacag cctaccatta acaccaacaa agatagcgag attgatgcac 8460
acaaacagga gtctggtatc gctcctaact ttgtacacag ccaagacggt agccaccttc 8520
gtaagactgt agtgtgggca cacgagaagt acggaatcga atcttttgca ctgattcacg 8580
actccttcgg taccattccg gctgacgctg cgaacctgtt caaagcagtg cgcgaaacta 8640
tggttgacac atatgagtct tgtgatgtac tggctgattt ctacgaccag ttcgctgacc 8700
agttgcacga gtctcaattg gacaaaatgc cagcacttcc ggctaaaggt aacttgaacc 8760
tccgtgacat cttagagtcg gacttcgcgt tcgcgtaacg ccaaatcaat acgactccgg 8820
atccccttcg aaggaaagac ctgatgcttt tcgtgcgcgc ataaaatacc ttgatactgt 8880
gccggatgaa agcggttcgc gacgagtaga tgcaattatg gtttctccgc caagaatctc 8940
tttgcattta tcaagtgttt ccttcattga tattccgaga gcatcaatat gcaatgctgt 9000
tgggatggca atttttacga agacgcttca gccaaaaaac ttaagaccgc cggtcttgtc 9060
cactaccttg cagtaatgcg gtggacagga tcggcggttt tcttttctct tctcaatgac 9120
cacgcagcca cataccggga gaccagaaac aaaaaaaggc cccccgttag ggaggccttc 9180
aataattggc tagctgtctt ctctagaggt gagtcctttt gtggagcgtg tccgttgagc 9240
gataccactc ggggttccgg cgttagcgac ggggagccaa agaccttatc gtctgcccac 9300
ccaccatgac aagatggata cagtgatgaa gtatttgcgc atgttatttg acaatttcac 9360
cctggccttg ctcggtgtgg tactcatcgc caccgtactg ccttgctcgg gcgatggcgc 9420
ggtgtatttc ggctggctga ccaacctggc cattggcctg ttgttcttcc tgcatggcgc 9480
caaactgtcc cgtgaagcca tcattgccgg tgccgggcac tggcgcctgc acctactggt 9540
gttctcctgt actttcgtat tgttcccgct gctgggcctg gcgttcaaac ctctgttcgt 9600
accgctggtg ggtaacgagc tttatctggg catcctgtac ctgtgtgcct tgcctgcaac 9660
cgtgcagtcg gccattgcct ttacctcgct ggcccgcggt aacgtgccag cggccatctg 9720
cagcgcggcg gcctccagcc tgctgggtat cttcctcacc ccgttgctgg tgatgctgct 9780
actgggcgcc ggtggtgata caggttccgg cctggatgcg gtgttgaaga tcactttgca 9840
gctgctggtg ccgttcgttg ccgggcaggt cgcgcggcgc tggatcggcg cctgggtcaa 9900
gcgcaatgcg cgctggctca aggtggtgga ccagggttcg atcctgctgg tggtgtacac 9960
cgccttcagt gaggccgtgg ttacaagctt ggcactggcc gtcgttttac aacgtcgtga 10020
ctgggaaaac cctggcgtta cccaacttaa tcgccttgca gcacatcccc ctttcgccag 10080
ctggcgtaat agcgaagagg cccgcaccga tcgcccttcc caacagttgc gcagcctgaa 10140
tggcgaatgg cgataagcta gcttcacgct gccgcaagca ctcagggcgc aagggctgct 10200
aaaggaagcg gaacacgtag aaagccagtc cgcagaaacg gtgctgacc 10249

<210> SEQ ID NO 95
<211> LENGTH: 10434
<212> TYPE: DNA
<213> ORGANISM: Artificial Sequence
<220> FEATURE:
<223> OTHER INFORMATION: Oligonucleotide

<400> SEQUENCE: 95
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480
gacgggcgtt ccttgcgcag ctgtgctcga cgttgtcact gaagcgggaa gggactggct 540
gctattgggc gaagtgccgg ggcaggatct cctgtcatct caccttgctc ctgccgagaa 600
agtatccatc atggctgatg caatgcggcg gctgcatacg cttgatccgg ctacctgccc 660
attcgaccac caagcgaaac atcgcatcga gcgagcacgt actcggatgg aagccggtct 720
tgtcgatcag gatgatctgg acgaagagca tcaggggctc gcgccagccg aactgttcgc 780
caggctcaag gcgcggatgc ccgacggcga ggatctcgtc gtgacccatg gcgatgcctg 840
cttgccgaat atcatggtgg aaaatggccg cttttctgga ttcatcgact gtggccggct 900
gggtgtggcg gaccgctatc aggacatagc gttggctacc cgtgatattg ctgaagagct 960
tggcggcgaa tgggctgacc gcttcctcgt gctttacggt atcgccgctc ccgattcgca 1020
gcgcatcgcc ttctatcgcc ttcttgacga gttcttctga gcgggactct ggggttcgct 1080
agaggatcga tcctttttaa cccatcacat atacctgccg ttcactatta tttagtgaaa 1140
tgagatatta tgatattttc tgaattgtga ttaaaaaggc aactttatgc ccatgcaaca 1200
gaaactataa aaaatacaga gaatgaaaag aaacagatag atttttttagt tctttaggcc 1260 cgtagtctgc aaatcctttt atgattttct atcaaacaaa agaggaaaat agaccagttg 1320
caatccaaac gagagtctaa tagaatgagg tcgaaaagta aatcgcgcgg gtttgttact 1380
gataaagcag gcaagaccta aaatgtgtaa agggcaaagt gtatactttg gcgtcacccc 1440
ttacatattt taggtctttt tttattgtgc gtaactaact tgccatcttc aaacaggagg 1500
gctggaagaa gcagaccgct aacacagtac ataaaaaagg agacatgaac gatgaacatc 1560
aaaaagtttg caaaacaagc aacagtatta acctttacta ccgcactgct ggcaggaggc 1620
gcaactcaag cgtttgcgaa agaaacgaac caaaagccat ataaggaaac atacggcatt 1680
tcccatatta cacgccatga tatgctgcaa atccctgaac agcaaaaaaa tgaaaaatat 1740
caagtttctg aatttgattc gtccacaatt aaaaatatct cttctgcaaa aggcctggac 1800

```
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
gttggaacct cttacgtgcc gatcaacgtc tcattttcgc caaaagttgg cccagggctt   4080
cccggtatca acagggacac caggatttat ttattctgcg aagtgatctt ccgtcacagg   4140
```

-continued

```
tatttattcg gcgcaaagtg cgtcgggtga tgctgccaac ttactgattt agtgtatgat   4200
ggtgtttttg aggtgctcca gtggcttctg tttctatcag ggctggatga tcctccagcg   4260
cggggatctc atgctggagt tcttcgccca ccccaaaagg atctaggtga agatcctttt   4320
tgataatctc atgaccaaaa tcccttaacg tgagttttcg ttccactgag cgtcagaccc   4380
cgtagaaaag atcaaaggat cttcttgaga tccttttttt ctgcgcgtaa tctgctgctt   4440
gcaaacaaaa aaaccaccgc taccagcggt ggtttgtttg ccggatcaag agctaccaac   4500
tctttttccg aaggtaactg gcttcagcag agcgcagata ccaaatactg ttcttctagt   4560
gtagccgtag ttaggccacc acttcaagaa ctctgtagca ccgcctacat acctcgctct   4620
gctaatcctg ttaccagtgg ctgctgccag tggcgataag tcgtgtctta ccgggttgga   4680
ctcaagacga tagttaccgg ataaggcgca gcggtcgggc tgaacggggg gttcgtgcac   4740
acagcccagc ttggagcgaa cgacctacac cgaactgaga tacctacagc gtgagctatg   4800
agaaagcgcc acgcttcccg aagggagaaa ggcggacagg tatccggtaa gcggcagggt   4860
cggaacagga gagcgcacga gggagcttcc agggggaaac gcctggtatc tttatagtcc   4920
tgtcgggttt cgccacctct gacttgagcg tcgatttttg tgatgctcgt caggggggcg   4980
gagcctatgg aaaaacgcca gcaacgcggc ctttttacgg ttcctggcct tttgctggcc   5040
ttttgctcac atgttctttc ctgcgttatc ccctgattct gtggataacc gtattaccgc   5100
ctttgagtga gctgataccg ctcgccgcag ccgaacgacc gagcgcagcg agtcagtgag   5160
cgaggaagcg gaagagcgcc caatacgcaa accgcctctc cccgcgcgtt ggccgattca   5220
ttaatgcagc tggcacgaca ggtttcccga ctggaaagcg ggcagtgagc gcaacgcaat   5280
taatgtgagt tagctcactc aggaaacagc tatgacatga ttacgaattc cttgcctctg   5340
ccggaaaccc gtctgcagcg gcgccaggca tgaaaaagcc cggcctatgc aggccgggct   5400
ctggtaaggg tgcgaaccct caattcagcg gttcgatcac cttgactgcc tgctgctcgc   5460
gggcagcggg ccattcttgt tgcagggtct gcagcacgcg gccaacgaat tcagtgtcgg   5520
cggcggcttt cttgccgacg taaccttggc cacggcggta gaccttgaag cgggcacgca   5580
tgctgggcag gtgctcttca aattcatctt cgacggtgtt cggtggcagg cggtcgaggc   5640
gcacttcacc ggtttggcta acccacagca aatggtcgtc aaggctgtcc ttgcgcacgg   5700
cgaacagctg ggccaattgg tcgatagtcg gattgttgtt caagttcatc ataaagcccc   5760
cattacccat tcataggtga ttttcacagt tggcgctatc acggtgtagc gcactaccaa   5820
ggctgctaca gcagcatcgc aacaggggct ttctcacgct gccttttgga cagtttccct   5880
ctccacggac ggcctgcgtt accgcgcagg ccgtctggaa caccccttgcc accgctcccg   5940
atcggggaga cggcttcatc atgcccaagc gcgatgaacg gcgtcaacca ttttgtagtg   6000
aatatttttg ctcactacat tctgtcgttt tgtccgacaa tcaacgcgag cgttaggatc   6060
cgcccgggtc aaaagcgccc ttttttgatg cgccggccct tgcggccagg cagcacagat   6120
cgggtgtgcc cctcacattc cctgcatccc cagaacctcc aggggtattc ggcactttta   6180
ttgcaaagac tgattgtgct caacgcactg gcaatctacc gagaccgagg ttaacgcgag   6240
acacagctcc cacttacccc agcaaggcag caccctgaaa gacgcagatg aaccgcaatg   6300
aagctgccgg caacggcggc aaggagtggg tatgaacacg attaacatcg ctaagaacga   6360
cttctctgac atcgaactgg ctgctatccc gttcaacact ctggctgacc attacggtga   6420
gcgtttagct cgcgaacagt tggcccttga gcatgagtct tacgagatgg gtgaagcacg   6480
cttccgcaag atgtttgagc gtcaacttaa agctggtgag gttgcggata acgctgccgc   6540
```

caagcctctc atcactaccc tactccctaa gatgattgca cgcatcaacg actggtttga 6600
ggaagtgaaa gctaagcgcg gcaagcgccc gacagccttc cagttcctgc aagaaatcaa 6660
gccggaagcc gtagcgtaca tcaccattaa gaccactctg gcttgcctaa ccagtgctga 6720
caatacaacc gttcaggctg tagcaagcgc aatcggtcgg gccattgagg acgaggctcg 6780
cttcggtcgt atccgtgacc ttgaagctaa gcacttcaag aaaaacgttg aggaacaact 6840
caacaagcgc gtagggcacg tctacaagaa agcatttatg caagttgtcg aggctgacat 6900
gctctctaag ggtctactcg gtggcgaggc gtggtcttcg tggcataagg aagactctat 6960
tcatgtagga gtacgctgca tcgagatgct cattgagtca accggaatgg ttagcttaca 7020
ccgccaaaat gctggcgtag taggtcaaga ctctgagact atcgaactcg cacctgaata 7080
cgctgaggct atcgcaaccc gtgcaggtgc gctggctggc atctctccga tgttccaacc 7140
ttgcgtagtt cctcctaagc cgtggactgg cattactggt ggtggctatt gggctaacgg 7200
tcgtcgtcct ctggcgctgg tgcgtactca cagtaagaaa gcactgatgc gctacgaaga 7260
cgtttacatg cctgaggtgt acaaagcgat taacattgcg caaaacaccg catggaaaat 7320
caacaagaaa gtcctagcgg tcgccaacgt aatcaccaag tggaagcatt gtccggtcga 7380
ggacatccct gcgattgagc gtgaagaact cccgatgaaa ccggaagaca tcgacatgaa 7440
tcctgaggct ctcaccgcgt ggaaacgtgc tgccgctgct gtgtaccgca aggacaaggc 7500
tcgcaagtct cgccgtatca gccttgagtt catgcttgag caagccaata agtttgctaa 7560
ccataaggcc atctggttcc cttacaacat ggactggcgc ggtcgtgttt acgctgtgtc 7620
aatgttcaac ccgcaaggta acgatatgac caaaggactg cttacgctgg cgaaaggtaa 7680
accaatcggt aaggaaggtt actactggct gaaaatccac ggtgcaaact gtgcgggtgt 7740
cgataaggtt ccgttccctg agcgcatcaa gttcattgag gaaaaccacg agaacatcat 7800
ggcttgcgct aagtctccac tggagaacac ttggtgggct gagcaagatt ctccgttctg 7860
cttccttgcg ttctgctttg agtacgctgg ggtacagcac cacggcctga gctataactg 7920
ctcccttccg ctggcgtttg acgggtcttg ctctggcatc cagcacttct ccgcgatgct 7980
ccgagatgag gtaggtggtc gcgcggttaa cttgcttcct agtgaaaccg ttcaggacat 8040
ctacgggatt gttgctaaga aagtcaacga gattctacaa gcagacgcaa tcaatgggac 8100
cgataacgaa gtagttaccg tgaccgatga gaacactggt gaaatctctg agaaagtcaa 8160
gctgggcact aaggcactgg ctggtcaatg gctggcttac ggtgttactc gcagtgtgac 8220
taagcgttca gtcatgacgc tggcttacgg gtccaaagag ttcggcttcc gtcaacaagt 8280
gctggaagat accattcagc cagctattga ttccggcaag ggtctgatgt tcactcagcc 8340
gaatcaggct gctggataca tggctaagct gatttgggaa tctgtgagcg tgacggtggt 8400
agctgcggtt gaagcaatga actggcttaa gtctgctgct aagctgctgg ctgctgaggt 8460
caaagataag aagactggag agattcttcg caagcgttgc gctgtgcatt gggtaactcc 8520
tgatggtttc cctgtgtggc aggaatacaa gaagcctatt cagacgcgct tgaacctgat 8580
gttcctcggt cagttccgct tacagcctac cattaacacc aacaaagata gcgagattga 8640
tgcacacaaa caggagtctg gtatcgctcc taactttgta cacagccaag acggtagcca 8700
ccttcgtaag actgtagtgt gggcacacga gaagtacgga atcgaatctt ttgcactgat 8760
tcacgactcc ttcggtacca ttccggctga cgctgcgaac ctgttcaaag cagtgcgcga 8820
aactatggtt gacacatatg agtcttgtga tgtactggct gatttctacg accagttcgc 8880

```
tgaccagttg cacgagtctc aattggacaa aatgccagca cttccggcta aaggtaactt   8940
gaacctccgt gacatcttag agtcggactt cgcgttcgcg taacgccaaa tcaatacgac   9000
tccggatccc cttcgaagga aagacctgat gcttttcgtg cgcgcataaa ataccttgat   9060
actgtgccgg atgaaagcgg ttcgcgacga gtagatgcaa ttatggtttc tccgccaaga   9120
atctctttgc atttatcaag tgtttccttc attgatattc cgagagcatc aatatgcaat   9180
gctgttggga tggcaatttt tacgaagacg cttcagccaa aaaacttaag accgccggtc   9240
ttgtccacta ccttgcagta atgcggtgga caggatcggc ggttttcttt tctcttctca   9300
atgaccacgc agccacatac cgggagacca gaaacaaaaa aaggcccccc gttagggagg   9360
ccttcaataa ttggctagct gtcttctcta gaggtgagtc cttttgtgga gcgtgtccgt   9420
tgagcgatac cactcggggt tccggcgtta gcgacgggga gccaaagacc ttatcgtctg   9480
cccacccacc atgacaagat ggatacagtg atgaagtatt tgcgcatgtt atttgacaat   9540
ttcaccctgg ccttgctcgg tgtggtactc atcgccaccg tactgccttg ctcgggcgat   9600
ggcgcggtgt atttcggctg gctgaccaac ctggccattg gcctgttgtt cttcctgcat   9660
ggcgccaaac tgtcccgtga agccatcatt gccggtgccg ggcactggcg cctgcaccta   9720
ctggtgttct cctgtacttt cgtattgttc ccgctgctgg gcctggcgtt caaacctctg   9780
ttcgtaccgc tggtgggtaa cgagctttat ctgggcatcc tgtacctgtg tgccttgcct   9840
gcaaccgtgc agtcggccat tgcctttacc tcgctggccc gcggtaacgt gccagcggcc   9900
atctgcagcg cggcggcctc cagcctgctg ggtatcttcc tcaccccgtt gctggtgatg   9960
ctgctactgg gcgccggtgg tgatacaggt tccggcctgg atgcggtgtt gaagatcact  10020
ttgcagctgc tggtgccgtt cgttgccggg caggtcgcgc ggcgctggat cggcgcctgg  10080
gtcaagcgca atgcgcgctg gctcaaggtg gtggaccagg gttcgatcct gctggtggtg  10140
tacaccgcct tcagtgaggc cgtggttaca agcttggcac tggccgtcgt tttacaacgt  10200
cgtgactggg aaaaccctgg cgttacccaa cttaatcgcc ttgcagcaca tccccctttc  10260
gccagctggc gtaatagcga agaggcccgc accgatcgcc cttcccaaca gttgcgcagc  10320
ctgaatggcg aatggcgata agctagcttc acgctgccgc aagcactcag ggcgcaaggg  10380
ctgctaaagg aagcggaaca cgtagaaagc cagtccgcag aaacggtgct gacc        10434
```

<210> SEQ ID NO 96
<211> LENGTH: 10414
<212> TYPE: DNA
<213> ORGANISM: Artificial Sequence
<220> FEATURE:
<223> OTHER INFORMATION: Oligonucleotide

<400> SEQUENCE: 96

```
ccggatgaat gtcagctact gggctatctg gacaagggaa aacgcaagcg caaagagaaa     60
gcaggtagct tgcagtgggc ttacatggcg atagctagac tgggcggttt tatggacagc    120
aagcgaaccg gaattgccag ctggggcgcc ctctggtaag gttgggaagc cctgcaaagt    180
aaactggatg gctttcttgc cgccaaggat ctgatggcgc aggggatcaa gatctgatca    240
agagacagga tgaggatcgt ttcgcatgat tgaacaagat ggattgcacg caggttctcc    300
ggccgcttgg gtggagaggc tattcggcta tgactgggca caacagacaa tcggctgctc    360
tgatgccgcc gtgttccggc tgtcagcgca ggggcgcccg gttctttttg tcaagaccga    420
cctgtccggt gccctgaatg aactccaaga cgaggcagcg cggctatcgt ggctggccac    480
gacgggcgtt ccttgcgcag ctgtgctcga cgttgtcact gaagcgggaa gggactggct    540
```

```
gctattgggc gaagtgccgg ggcaggatct cctgtcatct caccttgctc ctgccgagaa    600
agtatccatc atggctgatg caatgcggcg gctgcatacg cttgatccgg ctacctgccc    660
attcgaccac caagcgaaac atcgcatcga gcgagcacgt actcggatgg aagccggtct    720
tgtcgatcag gatgatctgg acgaagagca tcaggggctc gcgccagccg aactgttcgc    780
caggctcaag gcgcggatgc ccgacggcga ggatctcgtc gtgacccatg gcgatgcctg    840
cttgccgaat atcatggtgg aaaatggccg cttttctgga ttcatcgact gtggccggct    900
gggtgtggcg gaccgctatc aggacatagc gttggctacc cgtgatattg ctgaagagct    960
tggcggcgaa tgggctgacc gcttcctcgt gctttacggt atcgccgctc ccgattcgca   1020
gcgcatcgcc ttctatcgcc ttcttgacga gttcttctga gcgggactct ggggttcgct   1080
agaggatcga tcctttttaa cccatcacat atacctgccg ttcactatta tttagtgaaa   1140
tgagatatta tgatattttc tgaattgtga ttaaaaaggc aactttatgc ccatgcaaca   1200
gaaactataa aaaatacaga gaatgaaaag aaacagatag atttttagt tctttaggcc    1260
cgtagtctgc aaatcctttt atgattttct atcaaacaaa agaggaaaat agaccagttg   1320
caatccaaac gagagtctaa tagaatgagg tcgaaaagta aatcgcgcgg gtttgttact   1380
gataaagcag gcaagaccta aaatgtgtaa agggcaaagt gtatactttg gcgtcacccc   1440
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
```

```
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
gttggaacct cttacgtgcc gatcaacgtc tcattttcgc caaaagttgg cccagggctt   4080
cccggtatca acagggacac caggatttat ttattctgcg aagtgatctt ccgtcacagg   4140
tatttattcg gcgcaaagtg cgtcgggtga tgctgccaac ttactgattt agtgtatgat   4200
ggtgtttttg aggtgctcca gtggcttctg tttctatcag ggctggatga tcctccagcg   4260
cggggatctc atgctggagt tcttcgccca ccccaaaagg atctaggtga agatcctttt   4320
tgataatctc atgaccaaaa tcccttaacg tgagttttcg ttccactgag cgtcagaccc   4380
cgtagaaaag atcaaaggat cttcttgaga tccttttttt ctgcgcgtaa tctgctgctt   4440
gcaaacaaaa aaaccaccgc taccagcggt ggtttgtttg ccggatcaag agctaccaac   4500
tctttttccg aaggtaactg gcttcagcag agcgcagata ccaaatactg ttcttctagt   4560
gtagccgtag ttaggccacc acttcaagaa ctctgtagca ccgcctacat acctcgctct   4620
gctaatcctg ttaccagtgg ctgctgccag tggcgataag tcgtgtctta ccgggttgga   4680
ctcaagacga tagttaccgg ataaggcgca gcggtcgggc tgaacggggg gttcgtgcac   4740
acagcccagc ttggagcgaa cgacctacac cgaactgaga tacctacagc gtgagctatg   4800
agaaagcgcc acgcttcccg aagggagaaa ggcggacagg tatccggtaa gcggcagggt   4860
cggaacagga gagcgcacga gggagcttcc agggggaaac gcctggtatc tttatagtcc   4920
tgtcgggttt cgccacctct gacttgagcg tcgatttttg tgatgctcgt caggggggcg   4980
gagcctatgg aaaaacgcca gcaacgcggc ctttttacgg ttcctggcct tttgctggcc   5040
ttttgctcac atgttctttc ctgcgttatc ccctgattct gtggataacc gtattaccgc   5100
ctttgagtga gctgataccg ctcgccgcag ccgaacgacc gagcgcagcg agtcagtgag   5160
cgaggaagcg gaagagcgcc caatacgcaa accgcctctc cccgcgcgtt ggccgattca   5220
ttaatgcagc tggcacgaca ggtttcccga ctggaaagcg ggcagtgagc gcaacgcaat   5280
```

taatgtgagt tagctcactc aggaaacagc tatgacatga ttacgaattc cttgcctctg 5340
ccggaaaccc gtctgcagcg gcgccaggca tgaaaaagcc cggcctatgc aggccgggct 5400
ctggtaaggg tgcgaaccct caattcagcg gttcgatcac cttgactgcc tgctgctcgc 5460
gggcagcggg ccattcttgt tgcagggtct gcagcacgcg gccaacgaat tcagtgtcgg 5520
cggcggcttt cttgccgacg taaccttggc cacggcggta gaccttgaag cgggcacgca 5580
tgctgggcag gtgctcttca aattcatctt cgacggtgtt cggtggcagg cggtcgaggc 5640
gcacttcacc ggtttggcta acccacagca aatggtcgtc aaggctgtcc ttgcgcacgg 5700
cgaacagctg ggccaattgg tcgatagtcg gattgttgtt caagttcatc ataaagcccc 5760
cattacccat tcataggtga ttttcacagt tggcgctatc acggtgtagc gcactaccaa 5820
ggctgctaca gcagcatcgc aacaggggct ttctcacgct gccttttgga cagtttccct 5880
ctccacggac ggcctgcgtt accgcgcagg ccgtctggaa caccccttgcc accgctcccg 5940 atcggggaga cggcttcatc atgcccaagc gcgatgaacg gcgtcaacca ttttgtagtg 6000
aatatttttg ctcactacat tctgtcgttt tgtccgacaa tcaacgcgag cgttaggatc 6060
catggcctcg gggctgttc ccacgaaggc acggtgtacg ccgtccgatg tgggagcgcc 6120
cttgtgtcgc gatgggccgc accgcggccc caatcctgtg cacacaaatc catcaggcac 6180
caacctggat ccaaccaacg ccccaagacc tcgcacagcc cctctaaacc gtacctttcg 6240
ccactaggca cagcccttgc aacgccctcc ccgcttgccc aacaccataa aaaactcagc 6300
ggagagagca catgaacacg attaacatcg ctaagaacga cttctctgac atcgaactgg 6360
ctgctatccc gttcaacact ctggctgacc attacggtga gcgtttagct cgcgaacagt 6420
tggcccttga gcatgagtct tacgagatgg gtgaagcacg cttccgcaag atgtttgagc 6480
gtcaacttaa agctggtgag gttgcggata acgctgccgc caagcctctc atcactaccc 6540
tactccctaa gatgattgca cgcatcaacg actggtttga ggaagtgaaa gctaagcgcg 6600
gcaagcgccc gacagccttc cagttcctgc aagaaatcaa gccggaagcc gtagcgtaca 6660
tcaccattaa gaccactctg gcttgcctaa ccagtgctga caatacaacc gttcaggctg 6720
tagcaagcgc aatcggtcgg gccattgagg acgaggctcg cttcggtcgt atccgtgacc 6780
ttgaagctaa gcacttcaag aaaaacgttg aggaacaact caacaagcgc gtagggcacg 6840
tctacaagaa agcatttatg caagttgtcg aggctgacat gctctctaag ggtctactcg 6900
gtggcgaggc gtggtcttcg tggcataagg aagactctat tcatgtagga gtacgctgca 6960
tcgagatgct cattgagtca accggaatgg ttagcttaca ccgccaaaat gctggcgtag 7020
taggtcaaga ctctgagact atcgaactcg cacctgaata cgctgaggct atcgcaaccc 7080
gtgcaggtgc gctggctggc atctctccga tgttccaacc ttgcgtagtt cctcctaagc 7140
cgtggactgg cattactggt ggtggctatt gggctaacgg tcgtcgtcct ctggcgctgg 7200
tgcgtactca cagtaagaaa gcactgatgc gctacgaaga cgtttacatg cctgaggtgt 7260
acaaagcgat taacattgcg caaaacaccg catggaaaat caacaagaaa gtcctagcgg 7320
tcgccaacgt aatcaccaag tggaagcatt gtccggtcga ggacatccct gcgattgagc 7380
gtgaagaact cccgatgaaa ccggaagaca tcgacatgaa tcctgaggct ctcaccgcgt 7440
ggaaacgtgc tgccgctgct gtgtaccgca aggacaaggc tcgcaagtct cgccgtatca 7500
gccttgagtt catgcttgag caagccaata agtttgctaa ccataaggcc atctggttcc 7560
cttacaacat ggactggcgc ggtcgtgttt acgctgtgtc aatgttcaac ccgcaaggta 7620
acgatatgac caaaggactg cttacgctgg cgaaaggtaa accaatcggt aaggaaggtt 7680
actactggct gaaaatccac ggtgcaaact gtgcgggtgt cgataaggtt ccgttccctg 7740
agcgcatcaa gttcattgag gaaaaccacg agaacatcat ggcttgcgct aagtctccac 7800
tggagaacac ttggtgggct gagcaagatt ctccgttctg cttccttgcg ttctgctttg 7860
agtacgctgg ggtacagcac cacggcctga gctataactg ctcccttccg ctggcgtttg 7920
acgggtcttg ctctggcatc cagcacttct ccgcgatgct ccgagatgag gtaggtggtc 7980
gcgcggttaa cttgcttcct agtgaaaccg ttcaggacat ctacgggatt gttgctaaga 8040
aagtcaacga gattctacaa gcagacgcaa tcaatgggac cgataacgaa gtagttaccg 8100
tgaccgatga gaacactggt gaaatctctg agaaagtcaa gctgggcact aaggcactgg 8160
ctggtcaatg gctggcttac ggtgttactc gcagtgtgac taagcgttca gtcatgacgc 8220
tggcttacgg gtccaaagag ttcggcttcc gtcaacaagt gctggaagat accattcagc 8280
cagctattga ttccggcaag ggtctgatgt tcactcagcc gaatcaggct gctggataca 8340
tggctaagct gatttgggaa tctgtgagcg tgacggtggt agctgcggtt gaagcaatga 8400
actggcttaa gtctgctgct aagctgctgg ctgctgaggt caaagataag aagactggag 8460
agattcttcg caagcgttgc gctgtgcatt gggtaactcc tgatggtttc cctgtgtggc 8520
aggaatacaa gaagcctatt cagacgcgct tgaacctgat gttcctcggt cagttccgct 8580
tacagcctac cattaacacc aacaaagata gcgagattga tgcacacaaa caggagtctg 8640
gtatcgctcc taactttgta cacagccaag acggtagcca ccttcgtaag actgtagtgt 8700
gggcacacga gaagtacgga atcgaatctt ttgcactgat tcacgactcc ttcggtacca 8760
ttccggctga cgctgcgaac ctgttcaaag cagtgcgcga aactatggtt gacacatatg 8820
agtcttgtga tgtactggct gatttctacg accagttcgc tgaccagttg cacgagtctc 8880
aattggacaa aatgccagca cttccggcta aaggtaactt gaacctccgt gacatcttag 8940
agtcggactt cgcgttcgcg taacgccaaa tcaatacgac tccggatccc cttcgaagga 9000
aagacctgat gcttttcgtg cgcgcataaa ataccttgat actgtgccgg atgaaagcgg 9060
ttcgcgacga gtagatgcaa ttatggtttc tccgccaaga atctctttgc atttatcaag 9120
tgtttccttc attgatattc cgagagcatc aatatgcaat gctgttggga tggcaatttt 9180
tacgaagacg cttcagccaa aaaacttaag accgccggtc ttgtccacta ccttgcagta 9240
atgcggtgga caggatcggc ggttttcttt tctcttctca atgaccacgc agccacatac 9300
cgggagacca gaaacaaaaa aaggcccccc gttagggagg ccttcaataa ttggctagct 9360
gtcttctcta gaggtgagtc cttttgtgga gcgtgtccgt tgagcgatac cactcggggt 9420
tccggcgtta gcgacgggga gccaaagacc ttatcgtctg cccacccacc atgacaagat 9480
ggatacagtg atgaagtatt tgcgcatgtt atttgacaat ttcaccctgg ccttgctcgg 9540
tgtggtactc atcgccaccg tactgccttg ctcgggcgat ggcgcggtgt atttcggctg 9600
gctgaccaac ctggccattg gcctgttgtt cttcctgcat ggcgccaaac tgtcccgtga 9660
agccatcatt gccggtgccg ggcactggcg cctgcaccta ctggtgttct cctgtacttt 9720
cgtattgttc ccgctgctgg gcctggcgtt caaacctctg ttcgtaccgc tggtgggtaa 9780
cgagctttat ctgggcatcc tgtacctgtg tgccttgcct gcaaccgtgc agtcggccat 9840
tgcctttacc tcgctggccc gcggtaacgt gccagcggcc atctgcagcg cggcggcctc 9900
cagcctgctg ggtatcttcc tcaccccgtt gctggtgatg ctgctactgg gcgccggtgg 9960
tgatacaggt tccggcctgg atgcggtgtt gaagatcact ttgcagctgc tggtgccgtt 10020
cgttgccggg caggtcgcgc ggcgctggat cggcgcctgg gtcaagcgca atgcgcgctg 10080
gctcaaggtg gtggaccagg gttcgatcct gctggtggtg tacaccgcct tcagtgaggc 10140
cgtggttaca agcttggcac tggccgtcgt tttacaacgt cgtgactggg aaaaccctgg 10200
cgttacccaa cttaatcgcc ttgcagcaca tccccctttc gccagctggc gtaatagcga 10260
agaggcccgc accgatcgcc cttcccaaca gttgcgcagc ctgaatggcg aatggcgata 10320
agctagcttc acgctgccgc aagcactcag ggcgcaaggg ctgctaaagg aagcggaaca 10380
cgtagaaagc cagtccgcag aaacggtgct gacc 10414

<210> SEQ ID NO 97
<211> LENGTH: 10434
<212> TYPE: DNA
<213> ORGANISM: Artificial Sequence
<220> FEATURE:
<223> OTHER INFORMATION: Oligonucleotide

<400> SEQUENCE: 97
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480
gacgggcgtt ccttgcgcag ctgtgctcga cgttgtcact gaagcgggaa gggactggct 540
gctattgggc gaagtgccgg ggcaggatct cctgtcatct caccttgctc ctgccgagaa 600
agtatccatc atggctgatg caatgcggcg gctgcatacg cttgatccgg ctacctgccc 660
attcgaccac caagcgaaac atcgcatcga gcgagcacgt actcggatgg aagccggtct 720
tgtcgatcag gatgatctgg acgaagagca tcaggggctc gcgccagccg aactgttcgc 780
caggctcaag gcgcggatgc ccgacggcga ggatctcgtc gtgacccatg gcgatgcctg 840
cttgccgaat atcatggtgg aaaatggccg cttttctgga ttcatcgact gtggccggct 900
gggtgtggcg gaccgctatc aggacatagc gttggctacc cgtgatattg ctgaagagct 960
tggcggcgaa tgggctgacc gcttcctcgt gctttacggt atcgccgctc ccgattcgca 1020
gcgcatcgcc ttctatcgcc ttcttgacga gttcttctga gcgggactct ggggttcgct 1080
agaggatcga tcctttttaa cccatcacat atacctgccg ttcactatta tttagtgaaa 1140
tgagatatta tgatattttc tgaattgtga ttaaaaaggc aactttatgc ccatgcaaca 1200
gaaactataa aaaatacaga gaatgaaaag aaacagatag atttttttagt tctttaggcc 1260 cgtagtctgc aaatcctttt atgattttct atcaaacaaa agaggaaaat agaccagttg 1320
caatccaaac gagagtctaa tagaatgagg tcgaaaagta aatcgcgcgg gtttgttact 1380
gataaagcag gcaagaccta aaatgtgtaa agggcaaagt gtatactttg gcgtcacccc 1440
ttacatattt taggtctttt tttattgtgc gtaactaact tgccatcttc aaacaggagg 1500
gctggaagaa gcagaccgct aacacagtac ataaaaaagg agacatgaac gatgaacatc 1560
aaaaagtttg caaaacaagc aacagtatta acctttacta ccgcactgct ggcaggaggc 1620

-continued

```
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
```

-continued gttggaacct cttacgtgcc gatcaacgtc tcattttcgc caaaagttgg cccagggctt 4080
cccggtatca acagggacac caggatttat ttattctgcg aagtgatctt ccgtcacagg 4140
tatttattcg gcgcaaagtg cgtcgggtga tgctgccaac ttactgattt agtgtatgat 4200
ggtgtttttg aggtgctcca gtggcttctg tttctatcag ggctggatga tcctccagcg 4260
cggggatctc atgctggagt tcttcgccca ccccaaaagg atctaggtga agatcctttt 4320
tgataatctc atgaccaaaa tcccttaacg tgagttttcg ttccactgag cgtcagaccc 4380
cgtagaaaag atcaaaggat cttcttgaga tccttttttt ctgcgcgtaa tctgctgctt 4440
gcaaacaaaa aaaccaccgc taccagcggt ggtttgtttg ccggatcaag agctaccaac 4500
tctttttccg aaggtaactg gcttcagcag agcgcagata ccaaatactg ttcttctagt 4560
gtagccgtag ttaggccacc acttcaagaa ctctgtagca ccgcctacat acctcgctct 4620
gctaatcctg ttaccagtgg ctgctgccag tggcgataag tcgtgtctta ccgggttgga 4680
ctcaagacga tagttaccgg ataaggcgca gcggtcgggc tgaacggggg gttcgtgcac 4740
acagcccagc ttggagcgaa cgacctacac cgaactgaga tacctacagc gtgagctatg 4800
agaaagcgcc acgcttcccg aagggagaaa ggcggacagg tatccggtaa gcggcagggt 4860
cggaacagga gagcgcacga gggagcttcc agggggaaac gcctggtatc tttatagtcc 4920
tgtcgggttt cgccacctct gacttgagcg tcgatttttg tgatgctcgt caggggggcg 4980
gagcctatgg aaaaacgcca gcaacgcggc ctttttacgg ttcctggcct tttgctggcc 5040
ttttgctcac atgttctttc ctgcgttatc ccctgattct gtggataacc gtattaccgc 5100
ctttgagtga gctgataccg ctcgccgcag ccgaacgacc gagcgcagcg agtcagtgag 5160
cgaggaagcg gaagagcgcc caatacgcaa accgcctctc cccgcgcgtt ggccgattca 5220
ttaatgcagc tggcacgaca ggtttcccga ctggaaagcg ggcagtgagc gcaacgcaat 5280
taatgtgagt tagctcactc aggaaacagc tatgacatga ttacgaattc cttgcctctg 5340
ccggaaaccc gtctgcagcg gcgccaggca tgaaaaagcc cggcctatgc aggccgggct 5400
ctggtaaggg tgcgaaccct caattcagcg gttcgatcac cttgactgcc tgctgctcgc 5460
gggcagcggg ccattcttgt tgcagggtct gcagcacgcg gccaacgaat tcagtgtcgg 5520
cggcggcttt cttgccgacg taaccttggc cacggcggta gaccttgaag cgggcacgca 5580
tgctgggcag gtgctcttca aattcatctt cgacggtgtt cggtggcagg cggtcgaggc 5640
gcacttcacc ggtttggcta acccacagca aatggtcgtc aaggctgtcc ttgcgcacgg 5700
cgaacagctg ggccaattgg tcgatagtcg gattgttgtt caagttcatc ataaagcccc 5760
cattacccat tcataggtga ttttcacagt tggcgctatc acggtgtagc gcactaccaa 5820
ggctgctaca gcagcatcgc aacaggggct ttctcacgct gccttttgga cagtttccct 5880
ctccacggac ggcctgcgtt accgcgcagg ccgtctggaa caccccttgcc accgctcccg 5940 atcggggaga cggcttcatc atgcccaagc gcgatgaacg gcgtcaacca ttttgtagtg 6000
aatatttttg ctcactacat tctgtcgttt tgtccgacaa tcaacgcgag cgttaggatc 6060
cgctgcgcac cgaaattgtg catgtttccc gtgctggcga ctggccaatc ccgagcaaat 6120
cacataacgc gctgtttttc ggcgctttgt cggaactggc aaggtttctg caaagacctg 6180
tacgagccat gcactgaagc agttccttgt gaccaggcag tgcgcacgcg gagccggatg 6240
ccgacgacgc gttacaaagc caaccgctgc gcttagactt gagacgggtt tgttttcctg 6300
gggcaagtcc accaaatcgg gagagagttt catgaacacg attaacatcg ctaagaacga 6360

-continued

```
cttctctgac atcgaactgg ctgctatccc gttcaacact ctggctgacc attacggtga   6420
gcgtttagct cgcgaacagt tggcccttga gcatgagtct tacgagatgg gtgaagcacg   6480
cttccgcaag atgtttgagc gtcaacttaa agctggtgag gttgcggata acgctgccgc   6540
caagcctctc atcactaccc tactccctaa gatgattgca cgcatcaacg actggtttga   6600
ggaagtgaaa gctaagcgcg gcaagcgccc gacagccttc cagttcctgc aagaaatcaa   6660
gccggaagcc gtagcgtaca tcaccattaa gaccactctg gcttgcctaa ccagtgctga   6720
caatacaacc gttcaggctg tagcaagcgc aatcggtcgg gccattgagg acgaggctcg   6780
cttcggtcgt atccgtgacc ttgaagctaa gcacttcaag aaaaacgttg aggaacaact   6840
caacaagcgc gtagggcacg tctacaagaa agcatttatg caagttgtcg aggctgacat   6900
gctctctaag ggtctactcg gtggcgaggc gtggtcttcg tggcataagg aagactctat   6960
tcatgtagga gtacgctgca tcgagatgct cattgagtca accggaatgg ttagcttaca   7020
ccgccaaaat gctggcgtag taggtcaaga ctctgagact atcgaactcg cacctgaata   7080
cgctgaggct atcgcaaccc gtgcaggtgc gctggctggc atctctccga tgttccaacc   7140
ttgcgtagtt cctcctaagc cgtggactgg cattactggt ggtggctatt gggctaacgg   7200
tcgtcgtcct ctggcgctgg tgcgtactca cagtaagaaa gcactgatgc gctacgaaga   7260
cgtttacatg cctgaggtgt acaaagcgat taacattgcg caaaacaccg catggaaaat   7320
caacaagaaa gtcctagcgg tcgccaacgt aatcaccaag tggaagcatt gtccggtcga   7380
ggacatccct gcgattgagc gtgaagaact cccgatgaaa ccggaagaca tcgacatgaa   7440
tcctgaggct ctcaccgcgt ggaaacgtgc tgccgctgct gtgtaccgca aggacaaggc   7500
tcgcaagtct cgccgtatca gccttgagtt catgcttgag caagccaata agtttgctaa   7560
ccataaggcc atctggttcc cttacaacat ggactggcgc ggtcgtgttt acgctgtgtc   7620
aatgttcaac ccgcaaggta acgatatgac caaaggactg cttacgctgg cgaaaggtaa   7680
accaatcggt aaggaaggtt actactggct gaaaatccac ggtgcaaact gtgcgggtgt   7740
cgataaggtt ccgttccctg agcgcatcaa gttcattgag gaaaaccacg agaacatcat   7800
ggcttgcgct aagtctccac tggagaacac ttggtgggct gagcaagatt ctccgttctg   7860
cttccttgcg ttctgctttg agtacgctgg ggtacagcac cacggcctga gctataactg   7920
ctcccttccg ctggcgtttg acgggtcttg ctctggcatc cagcacttct ccgcgatgct   7980
ccgagatgag gtaggtggtc gcgcggttaa cttgcttcct agtgaaaccg ttcaggacat   8040
ctacgggatt gttgctaaga aagtcaacga gattctacaa gcagacgcaa tcaatgggac   8100
cgataacgaa gtagttaccg tgaccgatga gaacactggt gaaatctctg agaaagtcaa   8160
gctgggcact aaggcactgg ctggtcaatg gctggcttac ggtgttactc gcagtgtgac   8220
taagcgttca gtcatgacgc tggcttacgg gtccaaagag ttcggcttcc gtcaacaagt   8280
gctggaagat accattcagc cagctattga ttccggcaag ggtctgatgt tcactcagcc   8340
gaatcaggct gctggataca tggctaagct gatttgggaa tctgtgagcg tgacggtggt   8400
agctgcggtt gaagcaatga actggcttaa gtctgctgct aagctgctgg ctgctgaggt   8460
caaagataag aagactggag agattcttcg caagcgttgc gctgtgcatt gggtaactcc   8520
tgatggtttc cctgtgtggc aggaatacaa gaagcctatt cagacgcgct tgaacctgat   8580
gttcctcggt cagttccgct tacagcctac cattaacacc aacaaagata gcgagattga   8640
tgcacacaaa caggagtctg gtatcgctcc taactttgta cacagccaag acggtagcca   8700
ccttcgtaag actgtagtgt gggcacacga gaagtacgga atcgaatctt ttgcactgat   8760
```

tcacgactcc ttcggtacca ttccggctga cgctgcgaac ctgttcaaag cagtgcgcga 8820
aactatggtt gacacatatg agtcttgtga tgtactggct gatttctacg accagttcgc 8880
tgaccagttg cacgagtctc aattggacaa aatgccagca cttccggcta aaggtaactt 8940
gaacctccgt gacatcttag agtcggactt cgcgttcgcg taacgccaaa tcaatacgac 9000
tccggatccc cttcgaagga aagacctgat gcttttcgtg cgcgcataaa ataccttgat 9060
actgtgccgg atgaaagcgg ttcgcgacga gtagatgcaa ttatggtttc tccgccaaga 9120
atctctttgc atttatcaag tgtttccttc attgatattc cgagagcatc aatatgcaat 9180
gctgttggga tggcaatttt tacgaagacg cttcagccaa aaaacttaag accgccggtc 9240
ttgtccacta ccttgcagta atgcggtgga caggatcggc ggttttcttt tctcttctca 9300
atgaccacgc agccacatac cgggagacca gaaacaaaaa aaggcccccc gttagggagg 9360
ccttcaataa ttggctagct gtcttctcta gaggtgagtc cttttgtgga gcgtgtccgt 9420
tgagcgatac cactcggggt tccggcgtta gcgacgggga gccaaagacc ttatcgtctg 9480
cccacccacc atgacaagat ggatacagtg atgaagtatt tgcgcatgtt atttgacaat 9540
ttcaccctgg ccttgctcgg tgtggtactc atcgccaccg tactgccttg ctcgggcgat 9600
ggcgcggtgt atttcggctg gctgaccaac ctggccattg gcctgttgtt cttcctgcat 9660
ggcgccaaac tgtcccgtga agccatcatt gccggtgccg ggcactggcg cctgcaccta 9720
ctggtgttct cctgtacttt cgtattgttc ccgctgctgg gcctggcgtt caaacctctg 9780
ttcgtaccgc tggtgggtaa cgagctttat ctgggcatcc tgtacctgtg tgccttgcct 9840
gcaaccgtgc agtcggccat tgcctttacc tcgctggccc gcggtaacgt gccagcggcc 9900
atctgcagcg cggcggcctc cagcctgctg ggtatcttcc tcaccccgtt gctggtgatg 9960
ctgctactgg gcgccggtgg tgatacaggt tccggcctgg atgcggtgtt gaagatcact 10020
ttgcagctgc tggtgccgtt cgttgccggg caggtcgcgc ggcgctggat cggcgcctgg 10080
gtcaagcgca atgcgcgctg gctcaaggtg gtggaccagg gttcgatcct gctggtggtg 10140
tacaccgcct tcagtgaggc cgtggttaca agcttggcac tggccgtcgt tttacaacgt 10200
cgtgactggg aaaaccctgg cgttacccaa cttaatcgcc ttgcagcaca tccccctttc 10260
gccagctggc gtaatagcga agaggcccgc accgatcgcc cttcccaaca gttgcgcagc 10320
ctgaatggcg aatggcgata agctagcttc acgctgccgc aagcactcag ggcgcaaggg 10380
ctgctaaagg aagcggaaca cgtagaaagc cagtccgcag aaacggtgct gacc 10434

<210> SEQ ID NO 98
<211> LENGTH: 3311
<212> TYPE: DNA
<213> ORGANISM: Artificial Sequence
<220> FEATURE:
<223> OTHER INFORMATION: Oligonucleotide

<400> SEQUENCE: 98
aaaaggatct aggtgaagat cctttttgat aatctcatga ccaaaatccc ttaacgtgag 60
ttttcgttcc actgagcgtc agaccccgta gaaaagatca aaggatcttc ttgagatcct 120 tttttctgc gcgtaatctg ctgcttgcaa acaaaaaaac caccgctacc agcggtggtt 180
tgtttgccgg atcaagagct accaactctt tttccgaagg taactggctt cagcagagcg 240
cagataccaa atactgttct tctagtgtag ccgtagttag gccaccactt caagaactct 300
gtagcaccgc ctacatacct cgctctgcta atcctgttac cagtggctgc tgccagtggc 360

-continued

```
gataagtcgt gtcttaccgg gttggactca agacgatagt taccggataa ggcgcagcgg    420
tcgggctgaa cggggggttc gtgcacacag cccagcttgg agcgaacgac ctacaccgaa    480
ctgagatacc tacagcgtga gctatgagaa agcgccacgc ttcccgaagg gagaaaggcg    540
gacaggtatc cggtaagcgg cagggtcgga acaggagagc gcacgaggga gcttccaggg    600
ggaaacgcct ggtatcttta tagtcctgtc gggtttcgcc acctctgact tgagcgtcga    660
tttttgtgat gctcgtcagg ggggcggagc ctatggaaaa acgccagcaa cgcggccttt    720
ttacggttcc tggccttttg ctggcctttt gctcacatgt tctttcctgc gttatcccct    780
gattctgtgg ataaccgtat taccgccttt gagtgagctg ataccgctcg ccgcagccga    840
acgaccgagc gcagcgagtc agtgagcgag gaagcggaag agcgcccaat acgcaaaccg    900
cctctgggag accagaaaca aaaaaaggcc gcgttagcgg ccttcaataa ttggacctgg    960
ctcctaactg atttttaagg cgactgatga gtcgcctttt ttttgtctaa gaattcatca   1020
gaagaactcg tcaagaaggc gatagaaggc gatgcgctgc gaatcgggag cggcgatacc   1080
gtaaagcacg aggaagcggt cagcccattc gccgccaagc tcttcagcaa tatcacgggt   1140
agccaacgct atgtcctgat agcggtccgc cacacccagc cggccacagt cgatgaatcc   1200
agaaaagcgg ccattttcca ccatgatatt cggcaagcag gcatcgccat gggtcacgac   1260
gagatcctcg ccgtcgggca tccgcgcctt gagcctggcg aacagttcgg ctggcgcgag   1320
cccctgatgc tcttcgtcca gatcatcctg atcgacaaga ccggcttcca tccgagtacg   1380
tgctcgctcg atgcgatgtt tcgcttggtg gtcgaatggg caggtagccg gatcaagcgt   1440
atgcagccgc cgcattgcat cagccatgat ggatactttc tcggcaggag caaggtgaga   1500
tgacaggaga tcctgccccg gcacttcgcc caatagcagc cagtcccttc ccgcttcagt   1560
gacaacgtcg agcacagctg cgcaaggaac gcccgtcgtg gccagccacg atagccgcgc   1620
tgcctcgtct tggagttcat tcagggcacc ggacaggtcg gtcttgacaa aaagaaccgg   1680
gcgcccctgc gctgacagcc ggaacacggc ggcatcagag cagccgattg tctgttgtgc   1740
ccagtcatag ccgaatagcc tctccaccca agcggccgga gaacctgcgt gcaatccatc   1800
ttgttcaatc atgcgaaacg atcctcatcc tgtctcttga tcagatcttg atcccctgcg   1860
ccatcagatc cttggcggca agaaagccat ccagtttact ttgcagggct tcccaacctt   1920
accagagggc gccccagctg gcaattccgg ttcgcttgct gtccataaaa ccgcccagtc   1980
tagctatcgc catgtaagcc cactgcaagc tacctgcttt ctctttgcgc ttgcgttttc   2040
ccttgtccag atagcccagt agctgacatt catccgggac gtcgtgcccc aactggggta   2100
acctttgagt tctctcagtt gggggatcga tagtcaaaag cctccggtcg gaggcttttg   2160
actagcacct cggtaccaaa ttccagaaaa gaggcctccc gaaagggggg cctttttttcg  2220
ttttggtcca ctagtagtct taatacgact cactataggg agagacctgg aattgtgagc   2280
ggataacaat tcttaagatt aactcacaca ggagatatca tatggtgtcc aaaggggaag   2340
aggacaatat ggcatcgttg ccagctacgc atgaactgca catcttcggc tcgattaacg   2400
gtgtcgattt cgatatggtc ggccagggta cggggaatcc taacgacggt tatgaggagc   2460
tgaacctcaa atcgacgaag gggatctcc agtttagccc ctggattttg gtcccacata   2520
ttggttacgg ctttcatcag tacctcccgt atccggacgg tatgagccct tttcaagctg   2580
ctatggtgga cggtagcggt taccaagtcc accggaccat gcagtttgag gatggggcat   2640
cgctgacggt caactaccgt tatacctacg aaggtagcca tattaagggc gaagctcaag   2700
tgaagggtac cggctttccg gcggacggtc cggtgatgac gaactccctc accgccgccg   2760
```

attggtgtcg tagcaagaaa acctatccga atgacaaaac catcatctcg acgtttaagt 2820
ggagctatac gacgggtaat ggcaagcgct accgttcgac ggcacgtacc acctacacgt 2880
ttgcaaagcc tatggctgca aattacctca agaatcaacc tatgtatgtg ttccggaaaa 2940
cggaactcaa acatagcaaa acggaactga acttcaaaga gtggcagaaa gctttcacgg 3000
atgtcatggg tatggacgaa ctctataaat aatctagaga cgaacaataa ggcctcccta 3060
acggggggcc tttttattg ataacaaaaa tccacaagga aaaattaaag gggagataaa 3120
atcccccctt tttggttaac tgcggccgcg tcgtggtttg tctggtcaac caccgcggtc 3180
tcagtggtgt acggtacaaa ccccgacgct agcaacgcat gagaaagccc ccggaagatc 3240
accttccggg ggcttttta ttgcgctgcg ggtgccaggg cgtgcccttg ggctccccgg 3300
gcgcgtactc c 3311

<210> SEQ ID NO 99
<211> LENGTH: 13450
<212> TYPE: DNA
<213> ORGANISM: Artificial Sequence
<220> FEATURE:
<223> OTHER INFORMATION: Oligonucleotide

<400> SEQUENCE: 99
ccggatgaat gtcagctact gggctatctg gacaagggaa aacgcaagcg caaagagaaa 60
gcaggtagct tgcagtgggc ttacatggcg atagctagac tgggcggttt tatggacagc 120
aagcgaaccg gaattgccag ctggggcgcc ctctggtaag gttgggaagc cctgcaaagt 180
aaactggatg gctttcttgc cgccaaggat ctgatggcgc aggggatcaa gatctgatca 240
agagacagga tgaggatcgt ttcgcatgat tgaacaagat ggattgcacg caggttctcc 300
ggccgcttgg gtggagaggc tattcggcta tgactgggca caacagacaa tcggctgctc 360
tgatgccgcc gtgttccggc tgtcagcgca ggggcgcccg gttctttttg tcaagaccga 420
cctgtccggt gccctgaatg aactccaaga cgaggcagcg cggctatcgt ggctggccac 480
gacgggcgtt ccttgcgcag ctgtgctcga cgttgtcact gaagcgggaa gggactggct 540
gctattgggc gaagtgccgg ggcaggatct cctgtcatct caccttgctc ctgccgagaa 600
agtatccatc atggctgatg caatgcggcg gctgcatacg cttgatccgg ctacctgccc 660
attcgaccac caagcgaaac atcgcatcga gcgagcacgt actcggatgg aagccggtct 720
tgtcgatcag gatgatctgg acgaagagca tcaggggctc gcgccagccg aactgttcgc 780
caggctcaag gcgcggatgc ccgacggcga ggatctcgtc gtgacccatg gcgatgcctg 840
cttgccgaat atcatggtgg aaaatggccg cttttctgga ttcatcgact gtggccggct 900
gggtgtggcg gaccgctatc aggacatagc gttggctacc cgtgatattg ctgaagagct 960
tggcggcgaa tgggctgacc gcttcctcgt gctttacggt atcgccgctc ccgattcgca 1020
gcgcatcgcc ttctatcgcc ttcttgacga gttcttctga gcgggactct ggggttcgct 1080
agaggatcga tcctttttaa cccatcacat atacctgccg ttcactatta tttagtgaaa 1140
tgagatatta tgatattttc tgaattgtga ttaaaaaggc aactttatgc ccatgcaaca 1200
gaaactataa aaaatacaga gaatgaaaag aaacagatag atttttagt tctttaggcc 1260 cgtagtctgc aaatcctttt atgattttct atcaaacaaa agaggaaaat agaccagttg 1320
caatccaaac gagagtctaa tagaatgagg tcgaaaagta aatcgcgcgg gtttgttact 1380
gataaagcag gcaagaccta aaatgtgtaa agggcaaagt gtatactttg gcgtcacccc 1440

-continued

```
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
```

-continued

```
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
gttggaacct cttacgtgcc gatcaacgtc tcattttcgc caaaagttgg cccagggctt   4080
cccggtatca acagggacac caggatttat ttattctgcg aagtgatctt ccgtcacagg   4140
tatttattcg gcgcaaagtg cgtcgggtga tgctgccaac ttactgattt agtgtatgat   4200
ggtgtttttg aggtgctcca gtggcttctg tttctatcag ggctggatga tcctccagcg   4260
cggggatctc atgctggagt tcttcgccca ccccaaaagg atctaggtga agatcctttt   4320
tgataatctc atgaccaaaa tcccttaacg tgagttttcg ttccactgag cgtcagaccc   4380
cgtagaaaag atcaaaggat cttcttgaga tccttttttt ctgcgcgtaa tctgctgctt   4440
gcaaacaaaa aaaccaccgc taccagcggt ggtttgtttg ccggatcaag agctaccaac   4500
tctttttccg aaggtaactg gcttcagcag agcgcagata ccaaatactg ttcttctagt   4560
gtagccgtag ttaggccacc acttcaagaa ctctgtagca ccgcctacat acctcgctct   4620
gctaatcctg ttaccagtgg ctgctgccag tggcgataag tcgtgtctta ccgggttgga   4680
ctcaagacga tagttaccgg ataaggcgca gcggtcgggc tgaacggggg gttcgtgcac   4740
acagcccagc ttggagcgaa cgacctacac cgaactgaga tacctacagc gtgagctatg   4800
agaaagcgcc acgcttcccg aagggagaaa ggcggacagg tatccggtaa gcggcagggt   4860
cggaacagga gagcgcacga gggagcttcc agggggaaac gcctggtatc tttatagtcc   4920
tgtcgggttt cgccacctct gacttgagcg tcgatttttg tgatgctcgt caggggggcg   4980
gagcctatgg aaaaacgcca gcaacgcggc ctttttacgg ttcctggcct tttgctggcc   5040
ttttgctcac atgttctttc ctgcgttatc ccctgattct gtggataacc gtattaccgc   5100
ctttgagtga gctgataccg ctcgccgcag ccgaacgacc gagcgcagcg agtcagtgag   5160
cgaggaagcg gaagagcgcc caatacgcaa accgcctctc cccgcgcgtt ggccgattca   5220
ttaatgcagc tggcacgaca ggtttcccga ctggaaagcg ggcagtgagc gcaacgcaat   5280
taatgtgagt tagctcactc aggaaacagc tatgacatga ttacgaattc cttgcctctg   5340
ccggaaaccc gtctgcagcg gcgccaggca tgaaaaagcc cggcctatgc aggccgggct   5400
ctggtaaggg tgcgaaccct caattcagcg gttcgatcac cttgactgcc tgctgctcgc   5460
gggcagcggg ccattcttgt tgcagggtct gcagcacgcg gccaacgaat tcagtgtcgg   5520
cggcggcttt cttgccgacg taaccttggc cacggcggta gaccttgaag cgggcacgca   5580
tgctgggcag gtgctcttca aattcatctt cgacggtgtt cggtggcagg cggtcgaggc   5640
gcacttcacc ggtttggcta acccacagca aatggtcgtc aaggctgtcc ttgcgcacgg   5700
cgaacagctg ggccaattgg tcgatagtcg gattgttgtt caagttcatc ataaagcccc   5760
cattacccat tcataggtga ttttcacagt tggcgctatc acggtgtagc gcactaccaa   5820
ggctgctaca gcagcatcgc aacaggggct ttctcacgct gccttttgga cagtttccct   5880
ctccacggac ggcctgcgtt accgcgcagg ccgtctggaa cacccttgcc accgctcccg   5940
atcggggaga cggcttcatc atgcccaagc gcgatgaacg gcgtcaacca ttttgtagtg   6000
aatatttttg ctcactacat tctgtcgttt tgtccgacaa tcaacgcgag cgttaggatc   6060
catggcctcg gggctgttc ccacgaaggc acggtgtacg ccgtccgatg tgggagcgcc   6120
cttgtgtcgc gatgggccgc accgcggccc caatcctgtg cacacaaatc catcaggcac   6180
```

-continued caacctggat ccaaccaacg ccccaagacc tcgcacagcc cctctaaacc gtacctttcg 6240
ccactaggca cagcccttgc aacgccctcc ccgcttgccc aacaccataa aaaactcagc 6300
ggagagagca catgaacacg attaacatcg ctaagaacga cttctctgac atcgaactgg 6360
ctgctatccc gttcaacact ctggctgacc attacggtga gcgtttagct cgcgaacagt 6420
tggcccttga gcatgagtct tacgagatgg gtgaagcacg cttccgcaag atgtttgagc 6480
gtcaacttaa agctggtgag gttgcggata acgctgccgc caagcctctc atcactaccc 6540
tactccctaa gatgattgca cgcatcaacg actggtttga ggaagtgaaa gctaagcgcg 6600
gcaagcgccc gacagccttc cagttcctgc aagaaatcaa gccggaagcc gtagcgtaca 6660
tcaccattaa gaccactctg gcttgcctaa ccagtgctga caatacaacc gttcaggctg 6720
tagcaagcgc aatcggtcgg gccattgagg acgaggctcg cttcggtcgt atccgtgacc 6780
ttgaagctaa gcacttcaag aaaaacgttg aggaacaact caacaagcgc gtagggcacg 6840
tctacaagaa agcatttatg caagttgtcg aggctgacat gctctctaag ggtctactcg 6900
gtggcgaggc gtggtcttcg tggcataagg aagactctat tcatgtagga gtacgctgca 6960
tcgagatgct cattgagtca accggaatgg ttagcttaca ccgccaaaat gctggcgtag 7020
taggtcaaga ctctgagact atcgaactcg cacctgaata cgctgaggct atcgcaaccc 7080
gtgcaggtgc gctggctggc atctctccga tgttccaacc ttgcgtagtt cctcctaagc 7140
cgtggactgg cattactggt ggtggctatt gggctaacgg tcgtcgtcct ctggcgctgg 7200
tgcgtactca cagtaagaaa gcactgatgc gctacgaaga cgtttacatg cctgaggtgt 7260
acaaagcgat taacattgcg caaaacaccg catggaaaat caacaagaaa gtcctagcgg 7320
tcgccaacgt aatcaccaag tggaagcatt gtccggtcga ggacatccct gcgattgagc 7380
gtgaagaact cccgatgaaa ccggaagaca tcgacatgaa tcctgaggct ctcaccgcgt 7440
ggaaacgtgc tgccgctgct gtgtaccgca aggacaaggc tcgcaagtct cgccgtatca 7500
gccttgagtt catgcttgag caagccaata agtttgctaa ccataaggcc atctggttcc 7560
cttacaacat ggactggcgc ggtcgtgttt acgctgtgtc aatgttcaac ccgcaaggta 7620
acgatatgac caaaggactg cttacgctgg cgaaaggtaa accaatcggt aaggaaggtt 7680
actactggct gaaaatccac ggtgcaaact gtgcgggtgt cgataaggtt ccgttccctg 7740
agcgcatcaa gttcattgag gaaaaccacg agaacatcat ggcttgcgct aagtctccac 7800
tggagaacac ttggtgggct gagcaagatt ctccgttctg cttccttgcg ttctgctttg 7860
agtacgctgg ggtacagcac cacggcctga gctataactg ctcccttccg ctggcgtttg 7920
acgggtcttg ctctggcatc cagcacttct ccgcgatgct ccgagatgag gtaggtggtc 7980
gcgcggttaa cttgcttcct agtgaaaccg ttcaggacat ctacgggatt gttgctaaga 8040
aagtcaacga gattctacaa gcagacgcaa tcaatgggac cgataacgaa gtagttaccg 8100
tgaccgatga gaacactggt gaaatctctg agaaagtcaa gctgggcact aaggcactgg 8160
ctggtcaatg gctggcttac ggtgttactc gcagtgtgac taagcgttca gtcatgacgc 8220
tggcttacgg gtccaaagag ttcggcttcc gtcaacaagt gctggaagat accattcagc 8280
cagctattga ttccggcaag ggtctgatgt tcactcagcc gaatcaggct gctggataca 8340
tggctaagct gatttgggaa tctgtgagcg tgacggtggt agctgcggtt gaagcaatga 8400
actggcttaa gtctgctgct aagctgctgg ctgctgaggt caaagataag aagactggag 8460
agattcttcg caagcgttgc gctgtgcatt gggtaactcc tgatggtttc cctgtgtggc 8520
aggaatacaa gaagcctatt cagacgcgct tgaacctgat gttcctcggt cagttccgct 8580

-continued

```
tacagcctac cattaacacc aacaaagata gcgagattga tgcacacaaa caggagtctg   8640
gtatcgctcc taactttgta cacagccaag acggtagcca ccttcgtaag actgtagtgt   8700
gggcacacga gaagtacgga atcgaatctt ttgcactgat tcacgactcc ttcggtacca   8760
ttccggctga cgctgcgaac ctgttcaaag cagtgcgcga aactatggtt gacacatatg   8820
agtcttgtga tgtactggct gatttctacg accagttcgc tgaccagttg cacgagtctc   8880
aattggacaa aatgccagca cttccggcta aaggtaactt gaacctccgt gacatcttag   8940
agtcggactt cgcgttcgcg taacgccaaa tcaatacgac tccggatccc cttcgaagga   9000
aagacctgat gcttttcgtg cgcgcataaa ataccttgat actgtgccgg atgaaagcgg   9060
ttcgcgacga gtagatgcaa ttatggtttc tccgccaaga atctctttgc atttatcaag   9120
tgtttccttc attgatattc cgagagcatc aatatgcaat gctgttggga tggcaatttt   9180
tacgaagacg cttcagccaa aaaacttaag accgccggtc ttgtccacta ccttgcagta   9240
atgcggtgga caggatcggc ggttttcttt tctcttctca atgaccacgc agccacatac   9300
cgggagacca gaaacaaaaa aaggcccccc gttagggagg ccttcaataa ttggctagct   9360
gtcttctcta gtcctgttga taccgggaag ccctgggcca acttttggcg aaaatgagac   9420
gttgatcggc acgtaagagg ttccaacttt caccataatg aaataagatc actaccgggc   9480
gtattttttg agttatcgag attttcagga gctaaggaag ctaaaatgga gaaaaaaatc   9540
actggatata ccaccgttga tatatcccaa tggcatcgta aagaacattt tgaggcattt   9600
cagtcagttg ctcaatgtac ctataaccag accgttcagc tggatattac ggccttttta   9660
aagaccgtaa agaaaaataa gcacaagttt tatccggcct ttattcacat tcttgcccgc   9720
ctgatgaatg ctcatccgga attccgtatg gcaatgaaag acggtgagct ggtgatatgg   9780
gatagtgttc acccttgtta caccgttttc catgagcaaa ctgaaacgtt ttcatcgctc   9840
tggagtgaat accacgacga tttccggcag tttctacaca tatattcgca agatgtggcg   9900
tgttacggtg aaaacctggc ctatttccct aaagggttta ttgagaatat gtttttcgtc   9960
tcagccaatc cctgggtgag tttcaccagt tttgatttaa acgtggccaa tatggacaac  10020
ttcttcgccc ccgttttcac catgggcaaa tattatacgc aaggcgacaa ggtgctgatg  10080
ccgctggcga ttcaggttca tcatgccgtt tgtgatggct tccatgtcgg cagaatgctt  10140
aatgaattac aacagtactg cgatgagtgg cagggcgggg cgtaattttt ttaaggcagt  10200
tattggtgcc cttaaacgcc tggttgctac gcctgaataa gtgataataa gcggatgaat  10260
ggcagaaatt cgaaagcaaa ttcgacccgg tcgtcggttc agggcagggt cgttaaatag  10320
ccgcttatgt ctattgctgg tttaccggtt tattgactac cggaagcagt gtgaccgtgt  10380
gcttctcaaa tgcctgaggc cagtttgctc aggctctccc cgtggaggta ataattgacg  10440
atatgatcat ttattctgcc tcccagagcc tgataaaaac ggttagcgct tcgttaatac  10500
agatgtaggt gttccacagg gtagccagca gcatcctgcg atgcagatcc ggaacataat  10560
ggtgcagggc gcttgtttcg gcgtgggtat ggtggcaggc cccgtggccg gggactgtt   10620
gggcgctgcc ggcacctgtc ctacgagttg catgataaag aagacagtca taagtgcggc  10680
gacgatagtc atgccccgcg cccaccggaa ggagctaccg gacagcggtg cggactgttg  10740
taactcagaa taagaaatga ggccgctcat ggcgttgact ctcagtcata gtatcgtggt  10800
atcaccggtt ggttccactc tctgttgcgg gcaacttcag cagcacgtag gggacttccg  10860
cgtttccaga ctttacgaaa cacggaaacc gaagaccatt catgttgttg ctcaggtcgc  10920
```

-continued agacgttttg cagcagcagt cgcttcacgt tcgctcgcgt atcggtgatt cattctgcta 10980
accagtaagg caaccccgcc agcctagccg ggtcctcaac gacaggagca cgatcatgcg 11040
cacccgtggc caggacccaa cgctgcccga gatgcgccgc gtgcggctgc tggagatggc 11100
ggacgcgatg gatatgttct gccaagggtt ggtttgcgca ttcacagttc tccgcaagaa 11160
ttgattggct ccaattcttg gagtggtgaa tccgttagcg aggtgccgcc ggcttccatt 11220
caggtcgagg tggcccggct ccatgcaccg cgacgcaacg cggggaggca gacaaggtat 11280
agggcggcgc ctacaatcca tgccaacccg ttccatgtgc tcgccgaggc ggcataaatc 11340
gccgtgacga tcagcggtcc aatgatcgaa gttaggctgg taagagccgc gagcgatcct 11400
tgaagctgtc cctgatggtc gtcatctacc tgcctggaca gcatggcctg caacgcgggc 11460
atcccgatgc cgccggaagc gagaagaatc ataatgggga aggccatcca gcctcgcgtc 11520
gcgaacgcca gcaagacgta gcccagcgcg tcggccgcca tgccggcgat aatggcctgc 11580
ttctcgccga aacaagcgct catgagcccg aagtggcgag cccgatcttc cccatcggtg 11640
atgtcggcga tataggcgcc agcaaccgca cctgtggcgc cggtgatgcc ggccacgatg 11700
cgtccggcgt agaggatccg ggtccccttt gatagattaa aaaggaaagg aggaaagaaa 11760
taatggctcg tgtacagttt aaacaacgtg aatctactga cgcaatcttt gttcactgct 11820
cggctaccaa gccaagtcag aatgttggtg tccgtgagat tcgccagtgg cacaaagagc 11880
agggttggct cgatgtggga taccacttta tcatcaagcg agacggtact gtggaggcag 11940
gacgagatga gatggctgta ggctctcacg ctaagggtta caaccacaac tctatcggcg 12000
tctgccttgt tggtggtatc gacgataaag gtaagttcga cgctaacttt acgccagccc 12060
aaatgcaatc ccttcgctca ctgcttgtca cactgctggc taagtacgaa ggcgctgtgc 12120
ttcgcgccca tcatgaggtg gcgccgtacg cttgcccttc gttcgacctt aagcgttggt 12180
gggagaagaa cgaactggtc acttctgacc gtggataatt aattgaactc actaaaggga 12240
gaccacagcg gtttcccttt gttcgcattg gaggtcaaat aatgcgcaag tcttataaac 12300
aattctataa ggctccgagg aggcatatcc aagtgtggga ggcagccaat gggccggatc 12360
cacaggacgg gtgtggtcgc catgatcgcg tagtcgatag tgactagagg tgagtccttt 12420
tgtggagcgt gtccgttgag cgataccact cggggttccg gcgttagcga cggggagcca 12480
aagaccttat cgtctgccca cccaccatga caagatggat acagtgatga agtatttgcg 12540
catgttattt gacaatttca ccctggcctt gctcggtgtg gtactcatcg ccaccgtact 12600
gccttgctcg ggcgatggcg cggtgtattt cggctggctg accaacctgg ccattggcct 12660
gttgttcttc ctgcatggcg ccaaactgtc ccgtgaagcc atcattgccg gtgccgggca 12720
ctggcgcctg cacctactgg tgttctcctg tactttcgta ttgttcccgc tgctgggcct 12780
ggcgttcaaa cctctgttcg taccgctggt gggtaacgag ctttatctgg gcatcctgta 12840
cctgtgtgcc ttgcctgcaa ccgtgcagtc ggccattgcc tttacctcgc tggcccgcgg 12900
taacgtgcca gcggccatct gcagcgcggc ggcctccagc ctgctgggta tcttcctcac 12960
cccgttgctg gtgatgctgc tactgggcgc cggtggtgat acaggttccg gcctggatgc 13020
ggtgttgaag atcactttgc agctgctggt gccgttcgtt gccgggcagg tcgcgcggcg 13080
ctggatcggc gcctgggtca agcgcaatgc gcgctggctc aaggtggtgg accagggttc 13140
gatcctgctg gtggtgtaca ccgccttcag tgaggccgtg gttacaagct tggcactggc 13200
cgtcgtttta caacgtcgtg actgggaaaa ccctggcgtt acccaactta atcgccttgc 13260
agcacatccc cctttcgcca gctggcgtaa tagcgaagag gcccgcaccg atcgcccttc 13320
ccaacagttg cgcagcctga atggcgaatg gcgataagct agcttcacgc tgccgcaagc 13380
actcagggcg caagggctgc taaaggaagc ggaacacgta gaaagccagt ccgcagaaac 13440
ggtgctgacc 13450

<210> SEQ ID NO 100
<211> LENGTH: 4073
<212> TYPE: DNA
<213> ORGANISM: Artificial Sequence
<220> FEATURE:
<223> OTHER INFORMATION: Oligonucleotide

<400> SEQUENCE: 100
aaaaggatct aggtgaagat cctttttgat aatctcatga ccaaaatccc ttaacgtgag 60
ttttcgttcc actgagcgtc agaccccgta gaaaagatca aaggatcttc ttgagatcct 120 tttttctgc gcgtaatctg ctgcttgcaa acaaaaaaac caccgctacc agcggtggtt 180
tgtttgccgg atcaagagct accaactctt tttccgaagg taactggctt cagcagagcg 240
cagataccaa atactgttct tctagtgtag ccgtagttag gccaccactt caagaactct 300
gtagcaccgc ctacatacct cgctctgcta atcctgttac cagtggctgc tgccagtggc 360
gataagtcgt gtcttaccgg gttggactca agacgatagt taccggataa ggcgcagcgg 420
tcgggctgaa cggggggttc gtgcacacag cccagcttgg agcgaacgac ctacaccgaa 480
ctgagatacc tacagcgtga gctatgagaa agcgccacgc ttcccgaagg gagaaaggcg 540
gacaggtatc cggtaagcgg cagggtcgga acaggagagc gcacgaggga gcttccaggg 600
ggaaacgcct ggtatcttta tagtcctgtc gggtttcgcc acctctgact tgagcgtcga 660
tttttgtgat gctcgtcagg ggggcggagc ctatggaaaa acgccagcaa cgcggccttt 720
ttacggttcc tggccttttg ctggcctttt gctcacatgt tctttcctgc gttatcccct 780
gattctgtgg ataaccgtat taccgccttt gagtgagctg ataccgctcg ccgcagccga 840
acgaccgagc gcagcgagtc agtgagcgag gaagcggaag agcgcccaat acgcaaaccg 900
cctctgggag accagaaaca aaaaaaggcc gcgttagcgg ccttcaataa ttggacctgg 960
ctcctaactg atttttaagg cgactgatga gtcgcctttt ttttgtctaa gaattcatca 1020
gaagaactcg tcaagaaggc gatagaaggc gatgcgctgc gaatcgggag cggcgatacc 1080
gtaaagcacg aggaagcggt cagcccattc gccgccaagc tcttcagcaa tatcacgggt 1140
agccaacgct atgtcctgat agcggtccgc cacacccagc cggccacagt cgatgaatcc 1200
agaaaagcgg ccattttcca ccatgatatt cggcaagcag gcatcgccat gggtcacgac 1260
gagatcctcg ccgtcgggca tccgcgcctt gagcctggcg aacagttcgg ctggcgcgag 1320
cccctgatgc tcttcgtcca gatcatcctg atcgacaaga ccggcttcca tccgagtacg 1380
tgctcgctcg atgcgatgtt tcgcttggtg gtcgaatggg caggtagccg gatcaagcgt 1440
atgcagccgc cgcattgcat cagccatgat ggatactttc tcggcaggag caaggtgaga 1500
tgacaggaga tcctgccccg gcacttcgcc caatagcagc cagtcccttc ccgcttcagt 1560
gacaacgtcg agcacagctg cgcaaggaac gcccgtcgtg gccagccacg atagccgcgc 1620
tgcctcgtct tggagttcat tcagggcacc ggacaggtcg gtcttgacaa aaagaaccgg 1680
gcgcccctgc gctgacagcc ggaacacggc ggcatcagag cagccgattg tctgttgtgc 1740
ccagtcatag ccgaatagcc tctccaccca agcggccgga gaacctgcgt gcaatccatc 1800
ttgttcaatc atgcgaaacg atcctcatcc tgtctcttga tcagatcttg atcccctgcg 1860

```
ccatcagatc cttggcggca agaaagccat ccagtttact ttgcagggct tcccaacctt   1920

accagagggc gccccagctg gcaattccgg ttcgcttgct gtccataaaa ccgcccagtc   1980

tagctatcgc catgtaagcc cactgcaagc tacctgcttt ctctttgcgc ttgcgttttc   2040

ccttgtccag atagcccagt agctgacatt catccgggac gtcgtgcccc aactggggta   2100

acctttgagt tctctcagtt gggggatcga tagtcaaaag cctccggtcg gaggcttttg   2160

actagcacct cggtaccaaa ttccagaaaa gaggcctccc gaaagggggg cctttttttcg   2220

ttttggtcca ctagtagtct taatacgact cactataggg agagacctgg aattgtgagc   2280

ggataacaat tcttaagatt aactcacaca ggagatatca tatgaccaaa cagagcgcag   2340

atagcaatgc gaaaagcggt gtgaccagcg aaatttgcca ctgggcctcc aatctcgcga   2400

cggatgacat cccatcggac gtcctggagc gtgctaagta cctgatcctc gatgggatcg   2460

cgtgtgcatg ggtgggggca cgggtccctt ggagcgagaa atatgtccaa gcaacgatgt   2520

cctttgaacc ccctggtgcg tgccgggtga tcggctatgg tcaaaaattg ggccctgtcg   2580

ctgcagcgat gacgaactcg gcattcatcc aagcgaccga attggatgat taccattccg   2640

aggcaccgct gcatagcgca agcattgtgt tgccagcagt cttcgcggcg tcggaggtcc   2700

tcgctgaaca ggggaaaacg atttccggca ttgacgtgat cttggccgcg atcgtggggt   2760

ttgaatccgg ccctcggatt ggtaaagcca tctacgggag cgatttgctc aataacgggt   2820

ggcattgcgg ggccgtgtac ggtgccccctg ctggtgccct cgctaccggc aaattgctcg   2880

gcttgacgcc agattccatg gaggacgcct tggggattgc atgcacgcag gcctgtggtc   2940

tcatgagcgc tcagtatggc gggatggtga agcgggtgca acatgggttt gctgctcgta   3000

acgggctgct gggtggcttg ttggcgcacg gcggctatga agccatgaag gggtgctgg   3060

aacgcagcta tgggggtttt ctgaaaatgt ttaccaaggg taacggccgc gagccaccct   3120

acaaggaaga agaggtcgtg gcgggtctgg gttccttttg gcatacgttt accatccgga   3180

tcaagctcta tgcgtgttgt ggcttggtcc acggccccgt cgaagccatt gagaatctcc   3240

agggtcggta tcccgaactc ttgaatcgtg cgaacctctc gaatattcgt cacgtccatg   3300

tgcaactctc gacggcctcg aatagccatt gcggctggat cccagaggaa cgtccgatct   3360

cctcgatcgc tggtcagatg tccgtggctt atattttggc tgtccaattg gtggatcagc   3420

aatgcttgct gagccagttt tccgagtttg acgacaattt ggaacggccc gaagtgtggg   3480

atttggcacg caaagtcacg tccagccaat cggaagagtt cgatcaagac ggcaactgtt   3540

tgagcgcggg gcgtgtccgt atcgagttca atgatgggtc gtcgatcacg gagtccgtgg   3600

agaaaccact gggtgtcaaa gagcccatgc ctaatgaacg tattctgcat aaatatcgga   3660

ccttggcagg gtccgtcacc gacgaatccc gcgtcaagga gattgaggat ctggtcctcg   3720

ggctggaccg tttgacggac atcagcccct tgctcgaact gctcaattgc cctgtcaaat   3780

ccccccttggt ctaatctaga gacgaacaat aaggcctccc taacgggggg cctttttttat   3840

tgataacaaa aatccacaag gaaaaattaa aggggagata aaatcccccc tttttggtta   3900

actgcggccg cgtcgtggtt tgtctggtca accaccgcgg tctcagtggt gtacggtaca   3960

aaccccgacg ctagcaacgc atgagaaagc ccccggaaga tcaccttccg gggcttttt   4020

tattgcgctg cgggtgccag ggcgtgccct tgggctcccc gggcgcgtac tcc          4073
```

<210> SEQ ID NO 101
<211> LENGTH: 5501
<212> TYPE: DNA
<213> ORGANISM: Artificial Sequence
<220> FEATURE:
<223> OTHER INFORMATION: Oligonucleotide

<400> SEQUENCE: 101

```
aaaaggatct aggtgaagat cctttttgat aatctcatga ccaaaatccc ttaacgtgag     60
ttttcgttcc actgagcgtc agaccccgta gaaaagatca aaggatcttc ttgagatcct    120
tttttctgc gcgtaatctg ctgcttgcaa acaaaaaaac caccgctacc agcggtggtt    180
tgtttgccgg atcaagagct accaactctt tttccgaagg taactggctt cagcagagcg    240
cagataccaa atactgttct tctagtgtag ccgtagttag gccaccactt caagaactct    300
gtagcaccgc ctacatacct cgctctgcta atcctgttac cagtggctgc tgccagtggc    360
gataagtcgt gtcttaccgg gttggactca agacgatagt taccggataa ggcgcagcgg    420
tcgggctgaa cggggggttc gtgcacacag cccagcttgg agcgaacgac ctacaccgaa    480
ctgagatacc tacagcgtga gctatgagaa agcgccacgc ttcccgaagg gagaaaggcg    540
gacaggtatc cggtaagcgg cagggtcgga acaggagagc gcacgaggga gcttccaggg    600
ggaaacgcct ggtatcttta tagtcctgtc gggtttcgcc acctctgact tgagcgtcga    660
tttttgtgat gctcgtcagg ggggcggagc ctatggaaaa acgccagcaa cgcggccttt    720
ttacggttcc tggccttttg ctggcctttt gctcacatgt tctttcctgc gttatcccct    780
gattctgtgg ataaccgtat taccgccttt gagtgagctg ataccgctcg ccgcagccga    840
acgaccgagc gcagcgagtc agtgagcgag gaagcggaag agcgcccaat acgcaaaccg    900
cctctgggag accagaaaca aaaaaaggcc gcgttagcgg ccttcaataa ttggacctgg    960
ctcctaactg atttttaagg cgactgatga gtcgcctttt ttttgtctaa gaattcatca   1020
gaagaactcg tcaagaaggc gatagaaggc gatgcgctgc gaatcgggag cggcgatacc   1080
gtaaagcacg aggaagcggt cagcccattc gccgccaagc tcttcagcaa tatcacgggt   1140
agccaacgct atgtcctgat agcggtccgc cacacccagc cggccacagt cgatgaatcc   1200
agaaaagcgg ccattttcca ccatgatatt cggcaagcag gcatcgccat gggtcacgac   1260
gagatcctcg ccgtcgggca tccgcgcctt gagcctggcg aacagttcgg ctggcgcgag   1320
cccctgatgc tcttcgtcca gatcatcctg atcgacaaga ccggcttcca tccgagtacg   1380
tgctcgctcg atgcgatgtt tcgcttggtg gtcgaatggg caggtagccg gatcaagcgt   1440
atgcagccgc cgcattgcat cagccatgat ggatactttc tcggcaggag caaggtgaga   1500
tgacaggaga tcctgccccg gcacttcgcc caatagcagc cagtcccttc ccgcttcagt   1560
gacaacgtcg agcacagctg cgcaaggaac gcccgtcgtg gccagccacg atagccgcgc   1620
tgcctcgtct tggagttcat tcagggcacc ggacaggtcg gtcttgacaa aaagaaccgg   1680
gcgcccctgc gctgacagcc ggaacacggc ggcatcagag cagccgattg tctgttgtgc   1740
ccagtcatag ccgaatagcc tctccaccca agcggccgga gaacctgcgt gcaatccatc   1800
ttgttcaatc atgcgaaacg atcctcatcc tgtctcttga tcagatcttg atcccctgcg   1860
ccatcagatc cttggcggca agaaagccat ccagtttact ttgcagggct tcccaacctt   1920
accagagggc gccccagctg gcaattccgg ttcgcttgct gtccataaaa ccgcccagtc   1980
tagctatcgc catgtaagcc cactgcaagc tacctgcttt ctctttgcgc ttgcgttttc   2040
ccttgtccag atagcccagt agctgacatt catccgggac gtcgtgcccc aactggggta   2100
acctttgagt tctctcagtt gggggatcga tagtcaaaag cctccggtcg gaggcttttg   2160
actagcacct cggtaccaaa ttccagaaaa gaggcctccc gaaagggggg ccttttttcg   2220
```

-continued

```
ttttggtcca ctagtagtct taatacgact cactataggg agagacctgg aattgtgagc   2280
ggataacaat tcttaaggta gataagagcg ggtcatcgaa aggttatacc caaaacacgt   2340
aaggaggaac aacatggccc cggcactcaa tgccaatcca accacgaagc gcgacgaatt   2400
gtccgcacca tccgcgtccc acaagctggg gatgtcgtcc atggcgagcc gtgccgcagg   2460
cggcggcctg aaattgaccg gcctcccaga tttgtcggat agcgccggca ccttgtccga   2520
cattttcggt accccctcaaa tgcgcgaaat ttggagcgat cagaaccggg tggcatgcta   2580
cctcgaaatc gaggcggcct tggcaatcgt gcaggctgac ttgggtatca tcccgaagaa   2640
tgccgctcat gagattgtgg agcactgtcg tgtccaggaa atcgactggg cactgtataa   2700
acagaaaacc gaactgatcg gttaccctgt gctgggtatt gtccagcaac tggtggcaaa   2760
ttgcaaggat gggctcgggg agtattgcca ctggggcgcc acgacgcaag atatcacgga   2820
tacggctacg gtcatgcaga ttcgccagtc gctgaccttg gtgaagcaac ggttggatag   2880
catcgtcagc tcgttggagc acctcgccga acaacatcgg aacgtgccca tggccgcacg   2940
gagcaatttg aaacaggcgg tcccgatcac gtttggtttc aaaatggctc ggttcctcgc   3000
cacgtttcgc cgtcatcagc agcgtctggt cgagttggaa aagcgcgtgt acacgctgga   3060
gttcggcggg gccgctggta acctgtcgag cttgggtgac caagggatcg caacccatga   3120
cgctctggcc aagatgctgg atttggcgcc cgctgagatc gcttggcata ccgaacatga   3180
ccggttcgct gaggtgggga ccttcctggg cttgctgacg ggcaccctgg ccaaattggc   3240
aacggatatt aagctgatgt cgcagacgga ggtcggggaa gtcggcgaac cctttatttc   3300
caaccgtggc agctcgtcca cgatgccaca aaaaaataac cctatttcct gtgtctatat   3360
ccacgcttgc gccgccaatg tgcggcaagg tgctgccgca ctcttggacg caatgcaatc   3420
ggatcatgaa cgcggtaccg gtccatggga gatcatttgg gtccaactgc cgctcatgat   3480
gaactggacc tccgcagcgc tcaataacgc agactttgtc ttgcgtgggc tccaggtctt   3540
tcccgatgca atgcagcaca atctcgattt gtccaaaggt ctcatcgtct cggaagcagt   3600
gatgatgggt ttggggaaca cgctcggtcg ccagtacgcc cacgacgctg tgtatgaatg   3660
ttgccggacg gcttttgtcc aggatcgccc actgctcgat gtcttgttgg agaaccatga   3720
gatcgcctcg aaactcgatc gtaccgaact ggagaaattg tgtgatcccg cgaattattt   3780
ggggcaatgt tcccaatgga tcgatcgtgt gttgagccgt ccatcgtcgg cgtgaatacc   3840
ctatcagtac agcagtgcct agaattctca ggtacttaag gaggtctaat atgttgcatc   3900
cgattgacac cacgatctat cgcgcgggta cctcgcgtgg gctctatttt ttggcatcgg   3960
atttgcctgc tgaaccatcc gaacgtgacg cggccttgat cagcatcatg ggctccggcc   4020
atcccctgca aattgatggg atgggtgggg ggaacagcct cacctcgaaa gtggcaatcg   4080
tgtccgcaag cacccagcgc agcgaattcg acgtcgatta cctcttctgt caggtgggga   4140
ttacggagcg tttcgtggac acggccccaa attgtggtaa tctgatgtcc ggcgtggcgg   4200
cattcgctat cgagcgcggt ctcgtgcaac cgcatccgtc cgatacgacg tgtctcgtgc   4260
gcattttcaa tttgaacagc cgccaggcat cggaactcgt catccccgtc tataacggcc   4320
gtgtgcacta cgatgacatt gatgatatgc acatgcagcg cccgagcgcg cgggtcggcc   4380
tgcgtttttt ggataccgtc ggctcgtgca cgggcaaact cctcccgacc ggcaacgcgt   4440
cggactggat tgatggtctg aaagtcagca ttattgactc cgctgtcccc gtcgtgttca   4500
ttcgtcagca tgatgtgggc attaccgggt ccgaggcacc cgcaaccctg aacgctaaca   4560
ccgcattgtt ggaccgcctg gaacgggtgc ggttggaagc cgggcgccgg atggggttgg   4620
```

```
gtgatgtctc cggttccgtg gtccccaaac tcagcctcat tgggcctggc acggagacca   4680

ccacctttac cgcccgttat ttcacgccaa aggcgtgcca taatgcgcat gcagtgacgg   4740

gcgcgatttg taccgcaggt gccgcctata ttgacggttc ggtggtgtgt gaaattctga   4800

gctcgcgcgc ttccgcgtgt agcgcttcgc aacgtcggat ttcgattgaa cacccatcgg   4860

gggtcctgga agtcggcctc gtcccgcccg agaacgctgc ccagtcgctg gtcgatgtgg   4920

ctgtggtgga acggtcggtg gccctgattg cacatgctcg tgtgtactac accaccccag   4980

atcgccgccg gagctatgat tccccgctca cgtccccgtc gacgccagca gacacgcaca   5040

atctctttga tgcagcatac cgtccagtga tccaaccaag cgatacggac gtggaagccc   5100

ctcacatgct ggccctcgaa aacaaagaac aatgtgtgag ccggtgtgat accgccttgc   5160

accacatcgt ggcttcgtac ggggcctccg acgcccatgc aagcgaccgg agcttgtcct   5220

gatctagaga cgaacaataa ggcctcccta acggggggcc ttttttattg ataacaaaaa   5280

tccacaagga aaaattaaag gggagataaa atcccccctt tttggttaac tgcggccgcg   5340

tcgtggtttg tctggtcaac caccgcggtc tcagtggtgt acggtacaaa ccccgacgct   5400

agcaacgcat gagaaagccc ccggaagatc accttccggg ggcttttttta ttgcgctgcg  5460

ggtgccaggg cgtgcccttg ggctccccgg gcgcgtactc c                       5501
```

<210> SEQ ID NO 102
<211> LENGTH: 7601
<212> TYPE: DNA
<213> ORGANISM: Artificial Sequence
<220> FEATURE:
<223> OTHER INFORMATION: Oligonucleotide

<400> SEQUENCE: 102

```
ccggatgaat gtcagctact gggctatctg gacaagggaa aacgcaagcg caaagagaaa     60

gcaggtagct tgcagtgggc ttacatggcg atagctagac tgggcggttt tatggacagc    120

aagcgaaccg gaattgccag ctggggcgcc ctctggtaag gttgggaagc cctgcaaagt    180

aaactggatg gctttcttgc cgccaaggat ctgatggcgc aggggatcaa gatctgatca    240

agagacagga tgaggatcgt ttcgcatgat tgaacaagat ggattgcacg caggttctcc    300

ggccgcttgg gtggagaggc tattcggcta tgactgggca caacagacaa tcggctgctc    360

tgatgccgcc gtgttccggc tgtcagcgca ggggcgcccg gttctttttg tcaagaccga    420

cctgtccggt gccctgaatg aactccaaga cgaggcagcg cggctatcgt ggctggccac    480

gacgggcgtt ccttgcgcag ctgtgctcga cgttgtcact gaagcgggaa gggactggct    540

gctattgggc gaagtgccgg ggcaggatct cctgtcatct caccttgctc ctgccgagaa    600

agtatccatc atggctgatg caatgcggcg gctgcatacg cttgatccgg ctacctgccc    660

attcgaccac caagcgaaac atcgcatcga gcgagcacgt actcggatgg aagccggtct    720

tgtcgatcag gatgatctgg acgaagagca tcaggggctc gcgccagccg aactgttcgc    780

caggctcaag gcgcggatgc ccgacggcga ggatctcgtc gtgacccatg gcgatgcctg    840

cttgccgaat atcatggtgg aaaatggccg cttttctgga ttcatcgact gtggccggct    900

gggtgtggcg gaccgctatc aggacatagc gttggctacc cgtgatattg ctgaagagct    960

tggcggcgaa tgggctgacc gcttcctcgt gctttacggt atcgccgctc ccgattcgca   1020

gcgcatcgcc ttctatcgcc ttcttgacga gttcttctga gcgggactct ggggttcgct   1080

agaggatcga tcctttttaa cccatcacat atacctgccg ttcactatta tttagtgaaa   1140
```

```
tgagatatta tgatattttc tgaattgtga ttaaaaaggc aactttatgc ccatgcaaca   1200
gaaactataa aaaatacaga gaatgaaaag aaacagatag attttttagt tctttaggcc   1260
cgtagtctgc aaatcctttt atgattttct atcaaacaaa agaggaaaat agaccagttg   1320
caatccaaac gagagtctaa tagaatgagg tcgaaaagta aatcgcgcgg gtttgttact   1380
gataaagcag gcaagaccta aaatgtgtaa agggcaaagt gtatactttg gcgtcacccc   1440
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
```

-continued

```
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
gttggaacct cttacgtgcc gatcaacgtc tcattttcgc caaaagttgg cccagggctt   4080
cccggtatca acagggacac caggatttat ttattctgcg aagtgatctt ccgtcacagg   4140
tatttattcg gcgcaaagtg cgtcgggtga tgctgccaac ttactgattt agtgtatgat   4200
ggtgtttttg aggtgctcca gtggcttctg tttctatcag ggctggatga tcctccagcg   4260
cggggatctc atgctggagt tcttcgccca ccccaaaagg atctaggtga agatcctttt   4320
tgataatctc atgaccaaaa tcccttaacg tgagttttcg ttccactgag cgtcagaccc   4380
cgtagaaaag atcaaaggat cttcttgaga tccttttttt ctgcgcgtaa tctgctgctt   4440
gcaaacaaaa aaaccaccgc taccagcggt ggtttgtttg ccggatcaag agctaccaac   4500
tctttttccg aaggtaactg gcttcagcag agcgcagata ccaaatactg ttcttctagt   4560
gtagccgtag ttaggccacc acttcaagaa ctctgtagca ccgcctacat acctcgctct   4620
gctaatcctg ttaccagtgg ctgctgccag tggcgataag tcgtgtctta ccgggttgga   4680
ctcaagacga tagttaccgg ataaggcgca gcggtcgggc tgaacggggg gttcgtgcac   4740
acagcccagc ttggagcgaa cgacctacac cgaactgaga tacctacagc gtgagctatg   4800
agaaagcgcc acgcttcccg aagggagaaa ggcggacagg tatccggtaa gcggcagggt   4860
cggaacagga gagcgcacga gggagcttcc agggggaaac gcctggtatc tttatagtcc   4920
tgtcgggttt cgccacctct gacttgagcg tcgatttttg tgatgctcgt caggggggcg   4980
gagcctatgg aaaaacgcca gcaacgcggc ctttttacgg ttcctggcct tttgctggcc   5040
ttttgctcac atgttctttc ctgcgttatc ccctgattct gtggataacc gtattaccgc   5100
ctttgagtga gctgataccg ctcgccgcag ccgaacgacc gagcgcagcg agtcagtgag   5160
cgaggaagcg gaagagcgcc caatacgcaa accgcctctc cccgcgcgtt ggccgattca   5220
ttaatgcagc tggcacgaca ggtttcccga ctggaaagcg ggcagtgagc gcaacgcaat   5280
taatgtgagt tagctcactc aggaaacagc tatgacatga ttacgaattc gccgccatca   5340
agcagttcag cgccgaactc gtcacgcgcc acctcgtacc cccagtcctt gaaggcaccc   5400
tcggtgaact tcatgatgtt gcccttgtgc accagggtca gtgattcgcg gtcgttatcc   5460
accacgtatt gcagggcctt gcgcaccaga cgcttggtac cctccttcga caccggcttg   5520
acgccgatac cgcagtcctg gtcgaagcgg atcttggtga cccccatttc ctccttgaga   5580
aacttgatca ccttgttcgc ctcgggcgac ccggccttcc actcgatgcc ggcatagatg   5640
tcttcggagt tctcgcggaa gatcaccatg tcgacgtcgc ccggcttttt caccgggctt   5700
ggcacaccct ggaaccacag caccggccgc aggcatacat acaggtccag ttgctggcgc   5760
agggccacgt tgagggagcg gatgccgcca ccgacgggcg tggtcagcgg gcccttgatc   5820
gataccacat aatcacgcac ggcatcgagg gtttcctgcg gtagccaggt atcctggtca   5880
```

```
tacacctggg tggctttctc gccagcgtac acctccatcc aggcaatctt gcgcttgccg   5940

ccgtaggcct tctgcacggc ggcatcgacc accttgatca ttaccggcga aacatcgacg   6000

ccgatcccgt cgccttcgat gtaaggaatg atcggatggt caggcacgtt aagcgaatgg   6060

tctgcattga cggtaatttt ggtgccgtcg gtcggaacct tgattttctg gtatcccacc   6120

gaagcactac tccgctgtcg ggtgtggttt ggacatcgtg cgatccactg agcctaaacc   6180

acatctgccg acctgcaagg catgcgacaa cccgccgcat tgctgcttag tctttggtct   6240

tataaatggg ccgatatcac ttggccttgc tgattagccc aaatggtttg gtatactccg   6300

ccgcgaccga agggtcatcg gggcgaatcc caggaaaatg cggaccgccc taggccatga   6360

atggccataa agcctgggtt gttaccgcag ctcagcactt gacgctcgac tgatgcatcc   6420

accatcaccg ctcgcagcct ctcgactttc cgctcatggc gctgccaggg cgatgcgcct   6480

accctgcgca ccacgagact cgagcacgct cagcacacag agagttaaca aacgtgccca   6540

cccgttccaa gatcatctat accttcaccg acgaagcccc cgccctcgcc acttactcgc   6600

tgctgccgat catcgaagcg ttcaccgctt cggctgacat cgctgtcgaa actcgcgaca   6660

tttccctggc tggccgtatc cttgccgcct tcccggagca actgggcgca gagaagcaag   6720

taggcgatca cctggcggaa ctgggccagc tggctaccac ccctgaagcc aacatcatca   6780

agctgccgaa catcagcgcc tcggtaccgc agctcaaagc cgcgatcaag gaactgcaag   6840

gcaagggctt caacatccct gactacgccg acgagccggc caccgcggaa gaaaaagaat   6900

cccgcgcccg ctacgaccgc atcaagggct ccgccgtgaa cccggtgctg cgcgaaggca   6960

actccgaccg ccgcgcgccg ctgtcggtca agaactacgc ccgcaagcac ccacacaaga   7020

tgggcgcctg ggccgctgac tccaagtcgc acgttgccca catgacccag ggcgacttct   7080

acggcagcga aaaagccgca ctgatcgaag ctgacgacag cctgcgcatc gagctggtcg   7140

gcaaagacgg cagcaccacc gtgctgaaag aaaagaccgc cgtcaaagcc gccgaagtca   7200

tcgactgcgc caccatgagc cgcaaggccc tgaaagcctt catcgccgag cagatcgccg   7260

atgccaaggc cgctggcgtg ctgctgtcgg tgcacctgaa agccaccatg atgaaggtct   7320

ccgacccgat catgttaagc ttggcactgg ccgtcgtttt acaacgtcgt gactgggaaa   7380

accctggcgt tacccaactt aatcgccttg cagcacatcc ccctttcgcc agctggcgta   7440

atagcgaaga ggcccgcacc gatcgccctt cccaacagtt gcgcagcctg aatggcgaat   7500

ggcgataagc tagcttcacg ctgccgcaag cactcagggc gcaagggctg ctaaaggaag   7560

cggaacacgt agaaagccag tccgcagaaa cggtgctgac c                        7601
```

<210> SEQ ID NO 103
<211> LENGTH: 7601
<212> TYPE: DNA
<213> ORGANISM: Artificial Sequence
<220> FEATURE:
<223> OTHER INFORMATION: Oligonucleotide

<400> SEQUENCE: 103

```
ccggatgaat gtcagctact gggctatctg gacaagggaa aacgcaagcg caaagagaaa     60

gcaggtagct tgcagtgggc ttacatggcg atagctagac tgggcggttt tatggacagc    120

aagcgaaccg gaattgccag ctggggcgcc ctctggtaag gttgggaagc cctgcaaagt    180

aaactggatg gctttcttgc cgccaaggat ctgatggcgc aggggatcaa gatctgatca    240

agagacagga tgaggatcgt ttcgcatgat tgaacaagat ggattgcacg caggttctcc    300

ggccgcttgg gtggagaggc tattcggcta tgactgggca caacagacaa tcggctgctc    360
```

```
tgatgccgcc gtgttccggc tgtcagcgca ggggcgcccg gttctttttg tcaagaccga    420
cctgtccggt gccctgaatg aactccaaga cgaggcagcg cggctatcgt ggctggccac    480
gacgggcgtt ccttgcgcag ctgtgctcga cgttgtcact gaagcgggaa gggactggct    540
gctattgggc gaagtgccgg ggcaggatct cctgtcatct caccttgctc ctgccgagaa    600
agtatccatc atggctgatg caatgcggcg gctgcatacg cttgatccgg ctacctgccc    660
attcgaccac caagcgaaac atcgcatcga gcgagcacgt actcggatgg aagccggtct    720
tgtcgatcag gatgatctgg acgaagagca tcaggggctc gcgccagccg aactgttcgc    780
caggctcaag gcgcggatgc ccgacggcga ggatctcgtc gtgacccatg gcgatgcctg    840
cttgccgaat atcatggtgg aaaatggccg cttttctgga ttcatcgact gtggccggct    900
gggtgtggcg gaccgctatc aggacatagc gttggctacc cgtgatattg ctgaagagct    960
tggcggcgaa tgggctgacc gcttcctcgt gctttacggt atcgccgctc ccgattcgca   1020
gcgcatcgcc ttctatcgcc ttcttgacga gttcttctga gcgggactct ggggttcgct   1080
agaggatcga tcctttttaa cccatcacat atacctgccg ttcactatta tttagtgaaa   1140
tgagatatta tgatattttc tgaattgtga ttaaaaaggc aactttatgc ccatgcaaca   1200
gaaactataa aaaatacaga gaatgaaaag aaacagatag atttttagt tctttaggcc   1260
cgtagtctgc aaatcctttt atgattttct atcaaacaaa agaggaaaat agaccagttg   1320
caatccaaac gagagtctaa tagaatgagg tcgaaaagta aatcgcgcgg gtttgttact   1380
gataaagcag gcaagaccta aaatgtgtaa agggcaaagt gtatactttg gcgtcacccc   1440
ttacatattt taggtctttt tttattgtgc gtaactaact tgccatcttc aaacaggagg   1500
gctggaagaa gcagaccgct aacacagtac ataaaaaagg agacatgaac gatgaacatc   1560
aaaaagtttg caaaacaagc aacagtatta acctttacta ccgcactgct ggcaggaggc   1620
gcaactcaag cgtttgcgaa agaaacgaac caaaagccat ataaggaaac atacggcatt   1680
tcccatatta cacgccatga tatgctgcaa atccctgaac agcaaaaaaa tgaaaaatat   1740
caagtttctg aatttgattc gtccacaatt aaaaatatct cttctgcaaa aggcctggac   1800
gtttgggaca gctggccatt acaaaacgct gacggcactg tcgcaaacta tcacggctac   1860
cacatcgtct ttgcattagc cggagatcct aaaaatgcgg atgacacatc gatttacatg   1920
ttctatcaaa aagtcggcga aacttctatt gacagctgga aaaacgctgg ccgcgtcttt   1980
aaagacagcg acaaattcga tgcaaatgat tctatcctaa aagaccaaac acaagaatgg   2040
tcaggttcag ccacatttac atctgacgga aaaatccgtt tattctacac tgatttctcc   2100
ggtaaacatt acggcaaaca aacactgaca actgcacaag ttaacgtatc agcatcagac   2160
agctctttga acatcaacgg tgtagaggat tataaatcaa tctttgacgg tgacggaaaa   2220
acgtatcaaa atgtacagca gttcatcgat gaaggcaact acagctcagg cgacaaccat   2280
acgctgagag atcctcacta cgtagaagat aaaggccaca aatacttagt atttgaagca   2340
aacactggaa ctgaagatgg ctaccaaggc gaagaatctt tatttaacaa agcatactat   2400
ggcaaaagca catcattctt ccgtcaagaa agtcaaaaac ttctgcaaag cgataaaaaa   2460
cgcacggctg agttagcaaa cggcgctctc ggtatgattg agctaaacga tgattacaca   2520
ctgaaaaaag tgatgaaacc gctgattgca tctaacacag taacagatga aattgaacgc   2580
gcgaacgtct ttaaaatgaa cggcaaatgg tacctgttca ctgactcccg cggatcaaaa   2640
atgacgattg acggcattac gtctaacgat atttacatgc ttggttatgt ttctaattct   2700
```

```
ttaactggcc catacaagcc gctgaacaaa actggccttg tgttaaaaat ggatcttgat   2760
cctaacgatg taacctttac ttactcacac ttcgctgtac ctcaagcgaa aggaaacaat   2820
gtcgtgatta caagctatat gacaaacaga ggattctacg cagacaaaca atcaacgttt   2880
gcgccgagct tcctgctgaa catcaaaggc aagaaaacat ctgttgtcaa agacagcatc   2940
cttgaacaag gacaattaac agttaacaaa taaaaacgca aaagaaaatg ccgatgggta   3000
ccgagcgaaa tgaccgacca agcgacgccc aacctgccat cacgagattt cgattccacc   3060
gccgccttct atgaaaggtt gggcttcgga atcgttttcc gggacgccct cgcggacgtg   3120
ctcatagtcc acgacgcccg tgattttgta gccctggccg acggccagca ggtaggccga   3180
caggctcatg ccggccgccg ccgccttttc ctcaatcgct cttcgttcgt ctggaaggca   3240
gtacaccttg ataggtgggc tgcccttcct ggttggcttg gtttcatcag ccatccgctt   3300
gccctcatct gttacgccgg cggtagccgg ccagcctcgc agagcaggat tcccgttgag   3360
caccgccagg tgcgaataag ggacagtgaa gaaggaacac ccgctcgcgg gtgggcctac   3420
ttcacctatc ctgcccggct gacgccgttg gatacaccaa ggaaagtcta cacgaaccct   3480
ttggcaaaat cctgtatatc gtgcgaaaaa ggatggatat accgaaaaaa tcgctataat   3540
gaccccgaag cagggttatg cagcggaaaa gcgctgcttc cctgctgttt tgtggaatat   3600
ctaccgactg gaaacaggca aatgcaggaa attactgaac tgaggggaca ggcgagagac   3660
gatgccaaag agctcctgaa aatctcgata actcaaaaaa tacgcccggt agtgatctta   3720
tttcattatg gtgaaagttg gaacctctta cgtgccgatc aacgtctcat tttcgccaaa   3780
agttggccca gggcttcccg gtatcaacag ggacaccagg atttatttat tctgcgaagt   3840
gatcttccgt cacaggtatt tattcggcgc aaagtgcgtc gggtgatgct gccaacttac   3900
tgatttagtg tatgatggtg tttttgaggt gctccagtgg cttctgtttc tatcagctcc   3960
tgaaaatctc gataactcaa aaaatacgcc cggtagtgat cttatttcat tatggtgaaa   4020
gttggaacct cttacgtgcc gatcaacgtc tcattttcgc caaaagttgg cccagggctt   4080
cccggtatca acagggacac caggatttat ttattctgcg aagtgatctt ccgtcacagg   4140
tatttattcg gcgcaaagtg cgtcgggtga tgctgccaac ttactgattt agtgtatgat   4200
ggtgtttttg aggtgctcca gtggcttctg tttctatcag ggctggatga tcctccagcg   4260
cggggatctc atgctggagt tcttcgccca ccccaaaagg atctaggtga agatcctttt   4320
tgataatctc atgaccaaaa tcccttaacg tgagttttcg ttccactgag cgtcagaccc   4380
cgtagaaaag atcaaaggat cttcttgaga tccttttttt ctgcgcgtaa tctgctgctt   4440
gcaaacaaaa aaaccaccgc taccagcggt ggtttgtttg ccggatcaag agctaccaac   4500
tctttttccg aaggtaactg gcttcagcag agcgcagata ccaaatactg ttcttctagt   4560
gtagccgtag ttaggccacc acttcaagaa ctctgtagca ccgcctacat acctcgctct   4620
gctaatcctg ttaccagtgg ctgctgccag tggcgataag tcgtgtctta ccgggttgga   4680
ctcaagacga tagttaccgg ataaggcgca gcggtcgggc tgaacggggg gttcgtgcac   4740
acagcccagc ttggagcgaa cgacctacac cgaactgaga tacctacagc gtgagctatg   4800
agaaagcgcc acgcttcccg aagggagaaa ggcggacagg tatccggtaa gcggcagggt   4860
cggaacagga gagcgcacga gggagcttcc agggggaaac gcctggtatc tttatagtcc   4920
tgtcgggttt cgccacctct gacttgagcg tcgatttttg tgatgctcgt caggggggcg   4980
gagcctatgg aaaaacgcca gcaacgcggc ctttttacgg ttcctggcct tttgctggcc   5040
ttttgctcac atgttctttc ctgcgttatc ccctgattct gtggataacc gtattaccgc   5100
```

ctttgagtga gctgataccg ctcgccgcag ccgaacgacc gagcgcagcg agtcagtgag 5160
cgaggaagcg gaagagcgcc caatacgcaa accgcctctc cccgcgcgtt ggccgattca 5220
ttaatgcagc tggcacgaca ggtttcccga ctggaaagcg ggcagtgagc gcaacgcaat 5280
taatgtgagt tagctcactc aggaaacagc tatgacatga ttacgaattc gccgccatca 5340
agcagttcag cgccgaactc gtcacgcgcc acctcgtacc cccagtcctt gaaggcaccc 5400
tcggtgaact tcatgatgtt gcccttgtgc accagggtca gtgattcgcg gtcgttatcc 5460
accacgtatt gcagggcctt gcgcaccaga cgcttggtac cctccttcga caccggcttg 5520
acgccgatac cgcagtcctg gtcgaagcgg atcttggtga cccccatttc ctccttgaga 5580
aacttgatca ccttgttcgc ctcgggcgac ccggccttcc actcgatgcc ggcatagatg 5640
tcttcggagt tctcgcggaa gatcaccatg tcgacgtcgc ccggcttttt caccgggctt 5700
ggcacaccct ggaaccacag caccggccgc aggcatacat acaggtccag ttgctggcgc 5760
agggccacgt tgagggagcg gatgccgcca ccgacgggcg tggtcagcgg gcccttgatc 5820
gataccacat aatcacgcac ggcatcgagg gtttcctgcg gtagccaggt atcctggtca 5880
tacacctggg tggctttctc gccagcgtac acctccatcc aggcaatctt gcgcttgccg 5940
ccgtaggcct tctgcacggc ggcatcgacc accttgatca ttaccggcga aacatcgacg 6000
ccgatcccgt cgccttcgat gtaaggaatg atcggatggt caggcacgtt aagcgaatgg 6060
tctgcattga cggtaatttt ggtgccgtcg gtcggaacct tgattttctg gtatcccaac 6120
gaagcactac tccgctgtcg ggtgtggttt ggacatcgtg cgatccactg agcctaaacc 6180
acatctgccg acctgcaagg catgcgacaa cccgccgcat tgctgcttag tctttggtct 6240
tataaatggg ccgatatcac ttggccttgc tgattagccc aaatggtttg gtatactccg 6300
ccgcgaccga agggtcatcg ggcgaatcc caggaaaatg cggaccgccc taggccatga 6360
atggccataa agcctgggtt gttaccgcag ctcagcactt gacgctcgac tgatgcatcc 6420
accatcaccg ctcgcagcct ctcgactttc cgctcatggc gctgccaggg cgatgcgcct 6480
accctgcgca ccacgagact cgagcacgct cagcacacag agagttaaca aacttgccca 6540
cccgttccaa gatcatctat accttcaccg acgaagcccc cgccctcgcc acttactcgc 6600
tgctgccgat catcgaagcg ttcaccgctt cggctgacat cgctgtcgaa actcgcgaca 6660
tttccctggc tggccgtatc cttgccgcct tcccggagca actgggcgca gagaagcaag 6720
taggcgatca cctggcggaa ctgggccagc tggctaccac ccctgaagcc aacatcatca 6780
agctgccgaa catcagcgcc tcggtaccgc agctcaaagc cgcgatcaag gaactgcaag 6840
gcaagggctt caacatccct gactacgccg acgagccggc caccgcggaa gaaaaagaat 6900
cccgcgcccg ctacgaccgc atcaagggct ccgccgtgaa cccggtgctg cgcgaaggca 6960
actccgaccg ccgcgcgccg ctgtcggtca agaactacgc ccgcaagcac ccacacaaga 7020
tgggcgcctg ggccgctgac tccaagtcgc acgttgccca catgacccag ggcgacttct 7080
acggcagcga aaaagccgca ctgatcgaag ctgacgacag cctgcgcatc gagctggtcg 7140
gcaaagacgg cagcaccacc gtgctgaaag aaaagaccgc cgtcaaagcc gccgaagtca 7200
tcgactgcgc caccatgagc cgcaaggccc tgaaagcctt catcgccgag cagatcgccg 7260
atgccaaggc cgctggcgtg ctgctgtcgg tgcacctgaa agccaccatg atgaaggtct 7320
ccgacccgat catgttaagc ttggcactgg ccgtcgtttt acaacgtcgt gactgggaaa 7380
accctggcgt tacccaactt aatcgccttg cagcacatcc ccctttcgcc agctggcgta 7440

```
atagcgaaga ggcccgcacc gatcgccctt cccaacagtt gcgcagcctg aatggcgaat   7500

ggcgataagc tagcttcacg ctgccgcaag cactcagggc gcaagggctg ctaaaggaag   7560

cggaacacgt agaaagccag tccgcagaaa cggtgctgac c                       7601
```

<210> SEQ ID NO 104
<211> LENGTH: 3963
<212> TYPE: DNA
<213> ORGANISM: Artificial Sequence
<220> FEATURE:
<223> OTHER INFORMATION: Oligonucleotide

<400> SEQUENCE: 104

```
aaaaggatct aggtgaagat cctttttgat aatctcatga ccaaaatccc ttaacgtgag     60

ttttcgttcc actgagcgtc agaccccgta gaaaagatca aaggatcttc ttgagatcct    120

tttttctgc gcgtaatctg ctgcttgcaa acaaaaaaac caccgctacc agcggtggtt    180

tgtttgccgg atcaagagct accaactctt tttccgaagg taactggctt cagcagagcg    240

cagataccaa atactgttct tctagtgtag ccgtagttag gccaccactt caagaactct    300

gtagcaccgc ctacatacct cgctctgcta atcctgttac cagtggctgc tgccagtggc    360

gataagtcgt gtcttaccgg gttggactca agacgatagt taccggataa ggcgcagcgg    420

tcgggctgaa cggggggttc gtgcacacag cccagcttgg agcgaacgac ctacaccgaa    480

ctgagatacc tacagcgtga gctatgagaa agcgccacgc ttcccgaagg gagaaaggcg    540

gacaggtatc cggtaagcgg cagggtcgga acaggagagc gcacgaggga gcttccaggg    600

ggaaacgcct ggtatcttta tagtcctgtc gggtttcgcc acctctgact tgagcgtcga    660

tttttgtgat gctcgtcagg ggggcggagc ctatggaaaa acgccagcaa cgcggccttt    720

ttacggttcc tggccttttg ctggcctttt gctcacatgt tctttcctgc gttatcccct    780

gattctgtgg ataaccgtat taccgccttt gagtgagctg ataccgctcg ccgcagccga    840

acgaccgagc gcagcgagtc agtgagcgag gaagcggaag agcgcccaat acgcaaaccg    900

cctctgggag accagaaaca aaaaaaggcc gcgttagcgg ccttcaataa ttggacctgg    960

ctcctaactg atttttaagg cgactgatga gtcgcctttt ttttgtctaa gaattcatca   1020

gaagaactcg tcaagaaggc gatagaaggc gatgcgctgc gaatcgggag cggcgatacc   1080

gtaaagcacg aggaagcggt cagcccattc gccgccaagc tcttcagcaa tatcacgggt   1140

agccaacgct atgtcctgat agcggtccgc cacacccagc cggccacagt cgatgaatcc   1200

agaaaagcgg ccattttcca ccatgatatt cggcaagcag gcatcgccat gggtcacgac   1260

gagatcctcg ccgtcgggca tccgcgcctt gagcctggcg aacagttcgg ctggcgcgag   1320

cccctgatgc tcttcgtcca gatcatcctg atcgacaaga ccggcttcca tccgagtacg   1380

tgctcgctcg atgcgatgtt tcgcttggtg gtcgaatggg caggtagccg gatcaagcgt   1440

atgcagccgc cgcattgcat cagccatgat ggatactttc tcggcaggag caaggtgaga   1500

tgacaggaga tcctgccccg gcacttcgcc caatagcagc cagtcccttc ccgcttcagt   1560

gacaacgtcg agcacagctg cgcaaggaac gcccgtcgtg gccagccacg atagccgcgc   1620

tgcctcgtct tggagttcat tcagggcacc ggacaggtcg gtcttgacaa aaagaaccgg   1680

gcgcccctgc gctgacagcc ggaacacggc ggcatcagag cagccgattg tctgttgtgc   1740

ccagtcatag ccgaatagcc tctccaccca agcggccgga gaacctgcgt gcaatccatc   1800

ttgttcaatc atgcgaaacg atcctcatcc tgtctcttga tcagatcttg atcccctgcg   1860

ccatcagatc cttggcggca agaaagccat ccagtttact ttgcagggct tcccaacctt   1920
```

```
accagagggc gccccagctg gcaattccgg ttcgcttgct gtccataaaa ccgcccagtc   1980
tagctatcgc catgtaagcc cactgcaagc tacctgcttt ctctttgcgc ttgcgttttc   2040
ccttgtccag atagcccagt agctgacatt catccgggac gtcgtgcccc aactggggta   2100
acctttgagt tctctcagtt gggggatcga tagtcaaaag cctccggtcg gaggcttttg   2160
actagcacct cggtaccaaa ttccagaaaa gaggcctccc gaaagggggg cctttttttcg  2220
ttttggtcca ctagtagtct taatacgact cactataggg agagacctgg aattgtgagc   2280
ggataacaat tcttaagata ccctatcagt acagcagtgc ctagaattct caggtactta   2340
aggaggtcta atatgttgca tccgattgac accacgatct atcgcgcggg tacctcgcgt   2400
gggctctatt ttttggcatc ggatttgcct gctgaaccat ccgaacgtga cgcggccttg   2460
atcagcatca tgggctccgg ccatcccctg caaattgatg ggatgggtgg ggggaacagc   2520
ctcacctcga aagtggcaat cgtgtccgca agcacccagc gcagcgaatt cgacgtcgat   2580
tacctcttct gtcaggtggg gattacggag cgtttcgtgg acacggcccc aaattgtggt   2640
aatctgatgt ccggcgtggc ggcattcgct atcgagcgcg gtctcgtgca accgcatccg   2700
tccgatacga cgtgtctcgt gcgcattttc aatttgaaca gccgccaggc atcggaactc   2760
gtcatccccg tctataacgg ccgtgtgcac tacgatgaca ttgatgatat gcacatgcag   2820
cgcccgagcg cgcgggtcgg cctgcgtttt ttggataccg tcggctcgtg cacgggcaaa   2880
ctcctcccga ccggcaacgc gtcggactgg attgatggtc tgaaagtcag cattattgac   2940
tccgctgtcc ccgtcgtgtt cattcgtcag catgatgtgg gcattaccgg gtccgaggca   3000
cccgcaaccc tgaacgctaa caccgcattg ttggaccgcc tggaacgggt gcggttggaa   3060
gccgggcgcc ggatggggtt gggtgatgtc tccggttccg tggtccccaa actcagcctc   3120
attgggcctg gcacggagac caccaccttt accgcccgtt atttcacgcc aaaggcgtgc   3180
cataatgcgc atgcagtgac gggcgcgatt tgtaccgcag gtgccgccta tattgacggt   3240
tcggtggtgt gtgaaattct gagctcgcgc gcttccgcgt gtagcgcttc gcaacgtcgg   3300
atttcgattg aacacccatc gggggtcctg gaagtcggcc tcgtcccgcc cgagaacgct   3360
gcccagtcgc tggtcgatgt ggctgtggtg gaacggtcgg tggccctgat tgcacatgct   3420
cgtgtgtact acaccacccc agatcgccgc cggagctatg attccccgct cacgtccccg   3480
tcgacgccag cagacacgca caatctcttt gatgcagcat accgtccagt gatccaacca   3540
agcgatacgg acgtggaagc ccctcacatg ctggccctcg aaaacaaaga acaatgtgtg   3600
agccggtgtg ataccgcctt gcaccacatc gtggcttcgt acggggcctc cgacgcccat   3660
gcaagcgacc ggagcttgtc ctgatctaga gacgaacaat aaggcctccc taacgggggg   3720
cctttttttat tgataacaaa aatccacaag gaaaaattaa aggggagata aaatcccccc  3780
tttttggtta actgcggccg cgtcgtggtt tgtctggtca accaccgcgg tctcagtggt   3840
gtacggtaca aaccccgacg ctagcaacgc atgagaaagc ccccggaaga tcaccttccg   3900
ggggcttttt tattgcgctg cgggtgccag ggcgtgccct tgggctcccc gggcgcgtac   3960
tcc                                                                 3963
```

<210> SEQ ID NO 105
<211> LENGTH: 1473
<212> TYPE: DNA
<213> ORGANISM: Artificial Sequence
<220> FEATURE:
<223> OTHER INFORMATION: Oligonucleotide

<400> SEQUENCE: 105
atgaccaaac agagcgcaga tagcaatgcg aaaagcggtg tgaccagcga aatttgccac 60
tgggcctcca atctcgcgac ggatgacatc ccatcggacg tcctggagcg tgctaagtac 120
ctgatcctcg atgggatcgc gtgtgcatgg gtgggggcac gggtcccttg gagcgagaaa 180
tatgtccaag caacgatgtc ctttgaaccc cctggtgcgt gccgggtgat cggctatggt 240
caaaaattgg gccctgtcgc tgcagcgatg acgaactcgg cattcatcca agcgaccgaa 300
ttggatgatt accattccga ggcaccgctg catagcgcaa gcattgtgtt gccagcagtc 360
ttcgcggcgt cggaggtcct cgctgaacag ggaaaaacga tttccggcat tgacgtgatc 420
ttggccgcga tcgtggggtt tgaatccggc cctcggattg gtaaagccat ctacgggagc 480
gatttgctca ataacgggtg gcattgcggg gccgtgtacg gtgcccctgc tggtgccctc 540
gctaccggca aattgctcgg cttgacgcca gattccatgg aggacgcctt ggggattgca 600
tgcacgcagg cctgtggtct catgagcgct cagtatggcg ggatggtgaa gcgggtgcaa 660
catgggtttg ctgctcgtaa cggctgctg ggtggcttgt tggcgcacgg cggctatgaa 720
gccatgaagg gggtgctgga acgcagctat gggggttttc tgaaaatgtt taccaagggt 780
aacggccgcg agccacccta caaggaagaa gaggtcgtgg cgggtctggg ttcctttgg 840
catacgttta ccatccggat caagctctat gcgtgttgtg gcttggtcca cggccccgtc 900
gaagccattg agaatctcca gggtcggtat cccgaactct tgaatcgtgc gaacctctcg 960
aatattcgtc acgtccatgt gcaactctcg acggcctcga atagccattg cggctggatc 1020
ccagaggaac gtccgatctc ctcgatcgct ggtcagatgt ccgtggctta tattttggct 1080
gtccaattgg tggatcagca atgcttgctg agccagtttt ccgagtttga cgacaatttg 1140
gaacggcccg aagtgtggga tttggcacgc aaagtcacgt ccagccaatc ggaagagttc 1200
gatcaagacg gcaactgttt gagcgcgggg cgtgtccgta tcgagttcaa tgatgggtcg 1260
tcgatcacgg agtccgtgga gaaaccactg ggtgtcaaag agcccatgcc taatgaacgt 1320
attctgcata aatatcggac cttggcaggg tccgtcaccg acgaatcccg cgtcaaggag 1380
attgaggatc tggtcctcgg gctggaccgt ttgacggaca tcagcccctt gctcgaactg 1440
ctcaattgcc ctgtcaaatc cccettggtc taa 1473

<210> SEQ ID NO 106
<211> LENGTH: 1482
<212> TYPE: DNA
<213> ORGANISM: Artificial Sequence
<220> FEATURE:
<223> OTHER INFORMATION: Oligonucleotide

<400> SEQUENCE: 106
atggccccgg cactcaatgc caatccaacc acgaagcgcg acgaattgtc cgcaccatcc 60
gcgtcccaca agctggggat gtcgtccatg gcgagccgtg ccgcaggcgg cggcctgaaa 120
ttgaccggcc tcccagattt gtcggatagc gccggcacct tgtccgacat tttcggtacc 180
cctcaaatgc gcgaaatttg gagcgatcag aaccgggtgg catgctacct cgaaatcgag 240
gcggccttgg caatcgtgca ggctgacttg ggtatcatcc cgaagaatgc cgctcatgag 300
attgtggagc actgtcgtgt ccaggaaatc gactgggcac tgtataaaca gaaaaccgaa 360
ctgatcggtt accctgtgct gggtattgtc cagcaactgg tggcaaattg caaggatggg 420
ctcggggagt attgccactg gggcgccacg acgcaagata tcacggatac ggctacggtc 480
atgcagattc gccagtcgct gaccttggtg aagcaacggt tggatagcat cgtcagctcg 540

```
ttggagcacc tcgccgaaca acatcggaac gtgcccatgg ccgcacggag caatttgaaa    600
caggcggtcc cgatcacgtt tggtttcaaa atggctcggt tcctcgccac gtttcgccgt    660
catcagcagc gtctggtcga gttggaaaag cgcgtgtaca cgctggagtt cggcggggcc    720
gctggtaacc tgtcgagctt gggtgaccaa gggatcgcaa cccatgacgc tctggccaag    780
atgctggatt tggcgcccgc tgagatcgct tggcataccg aacatgaccg gttcgctgag    840
gtggggacct tcctgggctt gctgacgggc accctggcca aattggcaac ggatattaag    900
ctgatgtcgc agacggaggt cggggaagtc ggcgaaccct ttatttccaa ccgtggcagc    960
tcgtccacga tgccacaaaa aaataaccct atttcctgtg tctatatcca cgcttgcgcc   1020
gccaatgtgc ggcaaggtgc tgccgcactc ttggacgcaa tgcaatcgga tcatgaacgc   1080
ggtaccggtc catgggagat catttgggtc caactgccgc tcatgatgaa ctggacctcc   1140
gcagcgctca ataacgcaga ctttgtcttg cgtgggctcc aggtctttcc cgatgcaatg   1200
cagcacaatc tcgatttgtc caaaggtctc atcgtctcgg aagcagtgat gatgggtttg   1260
gggaacacgc tcggtcgcca gtacgcccac gacgctgtgt atgaatgttg ccggacggct   1320
tttgtccagg atcgcccact gctcgatgtc ttgttggaga accatgagat cgcctcgaaa   1380
ctcgatcgta ccgaactgga gaaattgtgt gatcccgcga attatttggg gcaatgttcc   1440
caatggatcg atcgtgtgtt gagccgtcca tcgtcggcgt ga                      1482
```

<210> SEQ ID NO 107
<211> LENGTH: 1332
<212> TYPE: DNA
<213> ORGANISM: Artificial Sequence
<220> FEATURE:
<223> OTHER INFORMATION: Oligonucleotide

<400> SEQUENCE: 107

```
atgttgcatc cgattgacac cacgatctat cgcgcgggta cctcgcgtgg gctctatttt     60
ttggcatcgg atttgcctgc tgaaccatcc gaacgtgacg cggccttgat cagcatcatg    120
ggctccggcc atcccctgca aattgatggg atgggtgggg ggaacagcct cacctcgaaa    180
gtggcaatcg tgtccgcaag cacccagcgc agcgaattcg acgtcgatta cctcttctgt    240
caggtgggga ttacggagcg tttcgtggac acggccccaa attgtggtaa tctgatgtcc    300
ggcgtggcgg cattcgctat cgagcgcggt ctcgtgcaac cgcatccgtc cgatacgacg    360
tgtctcgtgc gcattttcaa tttgaacagc cgccaggcat cggaactcgt catccccgtc    420
tataacggcc gtgtgcacta cgatgacatt gatgatatgc acatgcagcg cccgagcgcg    480
cgggtcggcc tgcgtttttt ggataccgtc ggctcgtgca cgggcaaact cctcccgacc    540
ggcaacgcgt cggactggat tgatggtctg aaagtcagca ttattgactc cgctgtcccc    600
gtcgtgttca ttcgtcagca tgatgtgggc attaccgggt ccgaggcacc cgcaaccctg    660
aacgctaaca ccgcattgtt ggaccgcctg gaacgggtgc ggttggaagc cgggcgccgg    720
atggggttgg gtgatgtctc cggttccgtg gtccccaaac tcagcctcat tgggcctggc    780
acggagacca ccacctttac cgcccgttat ttcacgccaa aggcgtgcca taatgcgcat    840
gcagtgacgg gcgcgatttg taccgcaggt gccgcctata ttgacggttc ggtggtgtgt    900
gaaattctga gctcgcgcgc ttccgcgtgt agcgcttcgc aacgtcggat ttcgattgaa    960
cacccatcgg gggtcctgga agtcggcctc gtcccgcccg agaacgctgc ccagtcgctg   1020
gtcgatgtgg ctgtggtgga acggtcggtg gccctgattg cacatgctcg tgtgtactac   1080
```

```
accaccccag atcgccgccg gagctatgat tccccgctca cgtccccgtc gacgccagca   1140

gacacgcaca atctctttga tgcagcatac cgtccagtga tccaaccaag cgatacggac   1200

gtggaagccc ctcacatgct ggccctcgaa aacaaagaac aatgtgtgag ccggtgtgat   1260

accgccttgc accacatcgt ggcttcgtac ggggcctccg acgcccatgc aagcgaccgg   1320

agcttgtcct ga                                                         1332


<210> SEQ ID NO 108
<211> LENGTH: 490
<212> TYPE: PRT
<213> ORGANISM: Aspergillus terreus

<400> SEQUENCE: 108

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
```

```
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ser Gln Phe Ser Glu Phe Asp Asp Asn Leu Glu Arg Pro Glu
    370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490


<210> SEQ ID NO 109
<211> LENGTH: 493
<212> TYPE: PRT
<213> ORGANISM: Ustilago maydis

<400> SEQUENCE: 109

Met Ala Pro Ala Leu Asn Ala Asn Pro Thr Thr Lys Arg Asp Glu Leu
1               5                   10                  15

Ser Ala Pro Ser Ala Ser His Lys Leu Gly Met Ser Ser Met Ala Ser
            20                  25                  30

Arg Ala Ala Gly Gly Gly Leu Lys Leu Thr Gly Leu Pro Asp Leu Ser
        35                  40                  45

Asp Ser Ala Gly Thr Leu Ser Asp Ile Phe Gly Thr Pro Gln Met Arg
    50                  55                  60

Glu Ile Trp Ser Asp Gln Asn Arg Val Ala Cys Tyr Leu Glu Ile Glu
65                  70                  75                  80

Ala Ala Leu Ala Ile Val Gln Ala Asp Leu Gly Ile Ile Pro Lys Asn
                85                  90                  95

Ala Ala His Glu Ile Val Glu His Cys Arg Val Gln Glu Ile Asp Trp
            100                 105                 110

Ala Leu Tyr Lys Gln Lys Thr Glu Leu Ile Gly Tyr Pro Val Leu Gly
        115                 120                 125

Ile Val Gln Gln Leu Val Ala Asn Cys Lys Asp Gly Leu Gly Glu Tyr
    130                 135                 140

Cys His Trp Gly Ala Thr Thr Gln Asp Ile Thr Asp Thr Ala Thr Val
145                 150                 155                 160

Met Gln Ile Arg Gln Ser Leu Thr Leu Val Lys Gln Arg Leu Asp Ser
                165                 170                 175

Ile Val Ser Ser Leu Glu His Leu Ala Glu Gln His Arg Asn Val Pro
            180                 185                 190

Met Ala Ala Arg Ser Asn Leu Lys Gln Ala Val Pro Ile Thr Phe Gly
        195                 200                 205
```

```
Phe Lys Met Ala Arg Phe Leu Ala Thr Phe Arg Arg His Gln Gln Arg
    210                 215                 220

Leu Val Glu Leu Glu Lys Arg Val Tyr Thr Leu Glu Phe Gly Gly Ala
225                 230                 235                 240

Ala Gly Asn Leu Ser Ser Leu Gly Asp Gln Gly Ile Ala Thr His Asp
                245                 250                 255

Ala Leu Ala Lys Met Leu Asp Leu Ala Pro Ala Glu Ile Ala Trp His
            260                 265                 270

Thr Glu His Asp Arg Phe Ala Glu Val Gly Thr Phe Leu Gly Leu Leu
        275                 280                 285

Thr Gly Thr Leu Ala Lys Leu Ala Thr Asp Ile Lys Leu Met Ser Gln
    290                 295                 300

Thr Glu Val Gly Glu Val Gly Glu Pro Phe Ile Ser Asn Arg Gly Ser
305                 310                 315                 320

Ser Ser Thr Met Pro Gln Lys Asn Asn Pro Ile Ser Cys Val Tyr Ile
                325                 330                 335

His Ala Cys Ala Ala Asn Val Arg Gln Gly Ala Ala Ala Leu Leu Asp
            340                 345                 350

Ala Met Gln Ser Asp His Glu Arg Gly Thr Gly Pro Trp Glu Ile Ile
        355                 360                 365

Trp Val Gln Leu Pro Leu Met Met Asn Trp Thr Ser Ala Ala Leu Asn
    370                 375                 380

Asn Ala Asp Phe Val Leu Arg Gly Leu Gln Val Phe Pro Asp Ala Met
385                 390                 395                 400

Gln His Asn Leu Asp Leu Ser Lys Gly Leu Ile Val Ser Glu Ala Val
                405                 410                 415

Met Met Gly Leu Gly Asn Thr Leu Gly Arg Gln Tyr Ala His Asp Ala
            420                 425                 430

Val Tyr Glu Cys Cys Arg Thr Ala Phe Val Gln Asp Arg Pro Leu Leu
        435                 440                 445

Asp Val Leu Leu Glu Asn His Glu Ile Ala Ser Lys Leu Asp Arg Thr
    450                 455                 460

Glu Leu Glu Lys Leu Cys Asp Pro Ala Asn Tyr Leu Gly Gln Cys Ser
465                 470                 475                 480

Gln Trp Ile Asp Arg Val Leu Ser Arg Pro Ser Ser Ala
                485                 490


<210> SEQ ID NO 110
<211> LENGTH: 443
<212> TYPE: PRT
<213> ORGANISM: Ustilago maydis

<400> SEQUENCE: 110

Met Leu His Pro Ile Asp Thr Thr Ile Tyr Arg Ala Gly Thr Ser Arg
1               5                   10                  15

Gly Leu Tyr Phe Leu Ala Ser Asp Leu Pro Ala Glu Pro Ser Glu Arg
            20                  25                  30

Asp Ala Ala Leu Ile Ser Ile Met Gly Ser Gly His Pro Leu Gln Ile
        35                  40                  45

Asp Gly Met Gly Gly Gly Asn Ser Leu Thr Ser Lys Val Ala Ile Val
    50                  55                  60

Ser Ala Ser Thr Gln Arg Ser Glu Phe Asp Val Asp Tyr Leu Phe Cys
65                  70                  75                  80

Gln Val Gly Ile Thr Glu Arg Phe Val Asp Thr Ala Pro Asn Cys Gly
                85                  90                  95
```

```
Asn Leu Met Ser Gly Val Ala Ala Phe Ala Ile Glu Arg Gly Leu Val
            100                 105                 110

Gln Pro His Pro Ser Asp Thr Thr Cys Leu Val Arg Ile Phe Asn Leu
        115                 120                 125

Asn Ser Arg Gln Ala Ser Glu Leu Val Ile Pro Val Tyr Asn Gly Arg
    130                 135                 140

Val His Tyr Asp Asp Ile Asp Asp Met His Met Gln Arg Pro Ser Ala
145                 150                 155                 160

Arg Val Gly Leu Arg Phe Leu Asp Thr Val Gly Ser Cys Thr Gly Lys
                165                 170                 175

Leu Leu Pro Thr Gly Asn Ala Ser Asp Trp Ile Asp Gly Leu Lys Val
            180                 185                 190

Ser Ile Ile Asp Ser Ala Val Pro Val Val Phe Ile Arg Gln His Asp
        195                 200                 205

Val Gly Ile Thr Gly Ser Glu Ala Pro Ala Thr Leu Asn Ala Asn Thr
    210                 215                 220

Ala Leu Leu Asp Arg Leu Glu Arg Val Arg Leu Glu Ala Gly Arg Arg
225                 230                 235                 240

Met Gly Leu Gly Asp Val Ser Gly Ser Val Val Pro Lys Leu Ser Leu
                245                 250                 255

Ile Gly Pro Gly Thr Glu Thr Thr Thr Phe Thr Ala Arg Tyr Phe Thr
            260                 265                 270

Pro Lys Ala Cys His Asn Ala His Ala Val Thr Gly Ala Ile Cys Thr
        275                 280                 285

Ala Gly Ala Ala Tyr Ile Asp Gly Ser Val Val Cys Glu Ile Leu Ser
    290                 295                 300

Ser Arg Ala Ser Ala Cys Ser Ala Ser Gln Arg Arg Ile Ser Ile Glu
305                 310                 315                 320

His Pro Ser Gly Val Leu Glu Val Gly Leu Val Pro Pro Glu Asn Ala
                325                 330                 335

Ala Gln Ser Leu Val Asp Val Ala Val Val Glu Arg Ser Val Ala Leu
            340                 345                 350

Ile Ala His Ala Arg Val Tyr Tyr Thr Thr Pro Asp Arg Arg Arg Ser
        355                 360                 365

Tyr Asp Ser Pro Leu Thr Ser Pro Ser Thr Pro Ala Asp Thr His Asn
    370                 375                 380

Leu Phe Asp Ala Ala Tyr Arg Pro Val Ile Gln Pro Ser Asp Thr Asp
385                 390                 395                 400

Val Glu Ala Pro His Met Leu Ala Leu Glu Asn Lys Glu Gln Cys Val
                405                 410                 415

Ser Arg Cys Asp Thr Ala Leu His His Ile Val Ala Ser Tyr Gly Ala
            420                 425                 430

Ser Asp Ala His Ala Ser Asp Arg Ser Leu Ser
        435                 440


<210> SEQ ID NO 111
<211> LENGTH: 491
<212> TYPE: PRT
<213> ORGANISM: Ustilago maydis

<400> SEQUENCE: 111

Met Asp Gln Ala Asp His Ser Gly Val Pro Asp Asp Ala Ala Leu Glu
1               5                   10                  15

Glu Ala Pro Asn Thr Val Pro Ile Gln Glu Lys Ser Ala Gln Pro His
```

-continued

```
            20                  25                  30

Asp Thr Gln Pro Tyr Cys Ala Phe Thr Lys Arg Ser Lys Leu Phe Ile
        35                  40                  45

Val Leu Thr Val Ser Leu Ala Gly Phe Phe Ser Pro Phe Ala Ile Asn
    50                  55                  60

Ile Tyr Ile Pro Ala Leu Pro Gln Ile Ala Gly Met Leu His Thr Ser
65                  70                  75                  80

Glu Ala Ala Thr Asn Val Thr Val Thr Val Tyr Met Ile Ala Gln Gly
                85                  90                  95

Leu Ser Pro Val Ile Trp Ala Pro Leu Ser Asp Val Phe Gly Arg Arg
            100                 105                 110

Pro Ile Tyr Ile Leu Thr Phe Phe Ile Phe Phe Ile Ala Asn Leu Gly
        115                 120                 125

Leu Ser Phe Thr Asn Val Tyr Trp Leu Leu Val Val Leu Arg Met Val
    130                 135                 140

Gln Ala Ala Gly Ala Cys Ser Ala Ile Ala Ile Gly Ala Gly Thr Ile
145                 150                 155                 160

Gly Asp Val Thr Glu Arg Lys Glu Arg Gly Ser Tyr Met Gly Tyr Tyr
                165                 170                 175

Ala Leu Ala Gln Tyr Thr Gly Pro Ala Ile Gly Pro Val Val Gly Gly
            180                 185                 190

Ala Leu Ser Gln Arg Trp Asp Tyr His Ala Thr Phe Phe Phe Leu Thr
        195                 200                 205

Ala Ile Ser Gly Pro Phe Leu Leu Phe Met Leu Leu Phe Leu Val Glu
    210                 215                 220

Thr Leu Arg Val Ile Val Gly Asn Gly Ser Ala Lys Thr Ser Gly Ile
225                 230                 235                 240

Tyr Arg Pro Leu Val Glu Pro Lys Leu Gln Arg Ser Ile Ala Asn Ala
                245                 250                 255

Pro Arg Pro Gly Ile Lys Asn Pro Leu His Gly Thr Leu Asp Phe Gly
            260                 265                 270

Phe His Arg Pro Phe Leu Val Phe Ala Arg Pro Glu Thr Ser Leu Ala
        275                 280                 285

Ile Leu Ala Phe Ser Met Val Tyr Ala Ser Tyr Tyr Leu Ser Ser Gly
    290                 295                 300

Ser Leu Pro Tyr Leu Phe Lys Gln Val Tyr Gly Leu Asp Glu Leu Leu
305                 310                 315                 320

Ile Gly Val Cys Phe Val Pro Ser Gly Val Gly Cys Ala Val Gly Thr
                325                 330                 335

Val Leu Ala Gly Lys Ile Leu Asp Trp Asp Tyr Arg Arg Ala Leu Asp
            340                 345                 350

Lys Ser Lys Leu Gly Val Lys Val Thr Arg Ala Arg Leu Gln Ser Ala
        355                 360                 365

Trp Ile Tyr Leu Pro Cys Tyr Cys Ala Ser Leu Leu Ala Tyr Gly Trp
    370                 375                 380

Cys Val Arg Ala His Thr His Ile Ala Ala Pro Ile Val Phe Gln Phe
385                 390                 395                 400

Thr Leu Gly Met Phe Ser Thr Met Tyr Phe Thr Asn Val Asn Thr Leu
                405                 410                 415

Ile Val Asp Leu Tyr Pro Gly Lys Ala Ala Ser Ala Thr Ala Ala Val
            420                 425                 430

Asn Val Gly Arg Cys Leu Leu Gly Ala Val Ala Val Ala Val Val Gln
        435                 440                 445
```

```
Pro Met Ile Asp Ala Met Gly Ala Gly Trp Thr Phe Thr Leu Gly Ala
    450                 455                 460

Leu Leu Thr Leu Ile Val Gly Leu Ile Cys Gln Val Leu Ile Tyr Leu
465                 470                 475                 480

Tyr Gly Glu Met Trp Ala Ala Arg Lys His Ser
                485                 490


<210> SEQ ID NO 112
<211> LENGTH: 303
<212> TYPE: PRT
<213> ORGANISM: Bacillus thuringiensus CT-43

<400> SEQUENCE: 112

Met Asp Asn Leu Lys Lys Ala Thr Phe Phe Met Val Leu Ser Gly Ile
1               5                   10                  15

Ser Phe Ser Leu Ser Gly Phe Phe Ala Glu His Ala Ile Ile Ser Gly
            20                  25                  30

Asp Phe Phe Val Thr Leu Thr Ala Arg Phe Phe Ile Pro Phe Leu Phe
        35                  40                  45

Leu Val Pro Phe Ile Ile Lys Arg Met Gly Lys Ile Ser Phe Trp Ser
    50                  55                  60

Asn Ser Tyr Lys Gln Leu Pro Arg Ala Phe Ser Ile Thr Phe Ser Gln
65                  70                  75                  80

Ala Leu Phe Phe Leu Cys Ala Ala Lys Thr Ser Leu Phe Ile Ala Met
                85                  90                  95

Val Leu Tyr Asn Thr Gly Pro Ile Phe Ile Cys Leu Ile Thr Leu Phe
            100                 105                 110

Ser Lys Thr Arg Arg Ala Thr Arg Ala Glu Ile Leu Ala Ala Phe Val
        115                 120                 125

Gly Phe Phe Gly Val Phe Leu Val Leu Lys Thr Gly Gly Ile Asp Tyr
    130                 135                 140

Glu Ser Phe Leu Tyr Leu Gly Val Gly Leu Leu Ser Gly Leu Ser Leu
145                 150                 155                 160

Ala Phe Ser Gln Phe Phe Leu His Arg Ser Ala Gln Thr Asp Asp Asn
                165                 170                 175

Leu Ser Ile Met Ala Tyr Thr Tyr Leu Tyr Gly Thr Ile Ile Ser Gly
            180                 185                 190

Val Leu Ser Ala Cys Phe Ser Lys Gly Asn Tyr Ile Gly Val Phe Thr
        195                 200                 205

Asn Ser Thr Met Val Leu Val Phe Leu Phe Leu Met Ala Met Gly Ser
    210                 215                 220

Leu Gly Asn Gln Trp Phe Arg Gly Arg Ala Tyr Lys Leu Thr Thr Arg
225                 230                 235                 240

Ile Ser Asn Leu Ser Ala Leu Leu Tyr Leu Asn Ile Leu Phe Ser Leu
                245                 250                 255

Leu Leu Asp Ile Leu Phe Asn Asn Ser Ile Pro Ser Val Ile Gln Ile
            260                 265                 270

Thr Gly Ala Ile Phe Val Met Gly Ser Ala Ala Ile Pro Ile Ile Val
        275                 280                 285

Arg Val Asn Lys Gln Gln Thr Glu Gln Arg Arg Ala Ala Ser Ser
    290                 295                 300
```